(12) United States Patent
Kim et al.

(10) Patent No.: US 9,809,839 B2
(45) Date of Patent: Nov. 7, 2017

(54) METHOD FOR CONCENTRATING CELLS THAT ARE GENETICALLY ALTERED BY NUCLEASES

(75) Inventors: Jin Soo Kim, Seoul (KR); Seok Joong Kim, Seoul (KR); Yong Sub Kim, Busanjin-gu (KR)

(73) Assignee: TOOLGEN INC., Seoul (KR)

( * ) Notice: Subject to any disclaimer, the term of this patent is extended or adjusted under 35 U.S.C. 154(b) by 0 days.

(21) Appl. No.: 14/000,920

(22) PCT Filed: Feb. 22, 2012

(86) PCT No.: PCT/KR2012/001367
§ 371 (c)(1),
(2), (4) Date: Oct. 22, 2013

(87) PCT Pub. No.: WO2012/115454
PCT Pub. Date: Aug. 30, 2012

(65) Prior Publication Data
US 2014/0045176 A1    Feb. 13, 2014

Related U.S. Application Data

(60) Provisional application No. 61/445,346, filed on Feb. 22, 2011.

(30) Foreign Application Priority Data

Sep. 16, 2011  (KR) .................. 10-2011-0093704

(51) Int. Cl.
| | | |
|---|---|---|
| C12Q 1/68 | (2006.01) | |
| G01N 33/50 | (2006.01) | |
| C12N 15/64 | (2006.01) | |
| C12Q 1/44 | (2006.01) | |
| C12Q 1/02 | (2006.01) | |
| C12Q 1/66 | (2006.01) | |
| C12N 15/63 | (2006.01) | |

(52) U.S. Cl.
CPC .............. C12Q 1/44 (2013.01); C12N 15/64 (2013.01); G01N 33/50 (2013.01)

(58) Field of Classification Search
None
See application file for complete search history.

(56) References Cited

U.S. PATENT DOCUMENTS

| 2005/0064474 A1 | 3/2005 | Urnov et al. |
| 2009/0111119 A1 | 4/2009 | Doyon et al. |
| 2011/0014616 A1 | 1/2011 | Holmes et al. |

FOREIGN PATENT DOCUMENTS

| FR | 2 839 726 A1 * | 11/2003 | ............. C12N 15/63 |
| KR | 10-2010-0087286 | 8/2010 | |
| WO | WO 2009/042163 | 4/2009 | |

OTHER PUBLICATIONS

Kim et al., "Targeted genome engineering via zinc finger nucleases" 5 Plant Biotechnology Reports 9-17 (Dec. 28, 2010).*
Lee et al., "Targeted chromosomal deletions in human cells using zinc finger nucleases" 20 Genome Research 81-89 (Jan. 2010).*
Doyon et al., "Heritable targeted gene disruption in zebrafish using designed zinc-finger nucleases" 26(6) Nature Biotechnology 702-708 (2008).*
Mao et al., "DNA repair by nonhomologous end joining and homologous recombination during cell cycle in human cells" 7(18) Cell Cycle 2902-2906 (2008).*
FR 2 839 726 Translation (EPO Patent Translate) (Nov. 21, 2003).*
Seluanov et al., "DNA end joining becomes less efficient and more error-prone during cellular senescence" 101(20) Proceedings of the National Academy of Sciences USA 7624-7629 (2004).*
International Search Report and the Written Opinion Dated Sep. 27, 2012 From the Intellectual Searching Authority Re. Application PCT/KR2012/001367.

* cited by examiner

*Primary Examiner* — Nancy J Leith
(74) *Attorney, Agent, or Firm* — Jones Day

(57) ABSTRACT

The present invention relates to a reporter construct and method for identifying or enriching the cells, wherein a specific endogenous nucleotide sequence is cleaved by a specific nuclease or modified by such cleavage; a host cell comprising the reporter construct; and a system for monitoring a nuclease activity. The reporter system of the present invention is simple and non-invasive, and allows for an efficient enrichment of the gene-modified cells. Therefore, the present invention will promote the application of a nuclease in the field of gene therapy and genetic engineering as well as basic research.

17 Claims, 37 Drawing Sheets

[Figure 1a]

TP53-L (sharkey RR FokI domain)
atggtgtaccctacgacgtgcccgactacgccgaattgcctccaaaaaagaagagaaaggtagggatccgaatt
cccggggaaaaaccgtaccactgtgactgggacggctgtggatggaaattcgcccgctcagatgaactgaccagg
cactaccgtaaacacaccggggaaaaaccgtacaggtgtaagtactgcgaccgctccttcagcgactcttcgaac
ctccagcggcacgtccggaacatccacaccggggaaaaaccgtaccactgtgactgggacggctgtggatggaaa
ttcgcccgctcagatgaactgaccaggcactaccgtaaacacaccggggaaaaaccgtacaaatgcccagaatgt
ggaaagagttttagcgatcctggacatcttgtgagacaccagagaacacataccggtgaaaaacaactagtcaaa
agtgaactggaggagaagaaatctgaacttcgtcataaattgaaatatgtgcctcatgaatatattgaattaatt
gaaattgccagaaatcccactcaggatagaattcttgaaatgaaggtaatggaatttttatgaaagtttatgga
tatagaggtgagcatttgggtggatcaaggaaaccggacggagcaatttatactgtcggatctcctattgattac
ggtgtgatcgtggatactaaagcttatagcggaggttataatctgccaattggccaagcacgagaaatgcaacga
tatgtcgaagaaaatcaaacacgaaacaaacatatcaaccctaatgaatggtggaaagtctatccatcttctgta
acggaatttaagttttatttgtgagtggtcactttaaaggaaactacaaagctcagcttacacgattaaatcat
atcactaattgtaatggagctgttcttagtgtagaagagcttttaattggtggagaaatgattaaagccggcaca
ttaaccttagaggaagtgagacggaaatttaataacggcgagataaactttctcgattag (SEQ ID NO: 1)

MVYPYDVPDYAELPPKKKRKVGIRIPGEKPYHCDWDGCGWKFARSDELTRHYRKHTGEKPYRCKYCDRSFSDSSN
LQRHVRNIHTGEKPYHCDWDGCGWKFARSDELTRHYRKHTGEKPYKCPECGKSFSDPGHLVRHQRTHTGEKQLVK
SELEEKKSELRHKLKYVPHEYIELIEIARNPTQDRILEMKVMEFFMKVYGYRGEHLGGSRKPDGAIYTVGSPIDY
GVIVDTKAYSGGYNLPIGQAREMQRYVEENQTRNKHINPNEWWKVYPSSVTEFKFLVSGHFKGNYKAQLTRLNH
ITNCNGAVLSVEELLIGGEMIKAGTLTLEEVRRKFNGEINFLD (SEQ ID NO: 2)

[Figure 1b]

TP53-R (sharkey DAS FokI domain)

atggtgtaccctacgacgtgcccgactacgccgaattgcctccaaaaaagaagagaaaggtagggatccgaatt
cccggggaaaaaccgtataagtgccctgattgtgggaagagttttagtcagagttccagcctcattcgccaccag
cggacacacaccggggaaaaaccgtacaaatgtgacgaatgtggaaaaaactttaccagtcctccaaccttatt
gtacataagagaattcataccggggaaaaacgtacaagtgccccgagtgcggcaagagcttcagccagaacagc
accctgaccgagcaccagcggacccacaccggggaaaaaccgtatgaatgcgatcactgtgggaaagccttcagc
gtcagctccaacctgaacgtgcacagaagaatccacaccggtgaaaaacaactagtcaaaagtgaactggaggag
aagaaatctgaacttcgtcataaattgaaatatgtgcctcatgaatatattgaattaattgaaattgccagaaat
cccactcaggatagaattcttgaaatgaaggtaatggaattttttatgaaagtttatggatatagaggtgagcat
ttgggtggatcaaggaaaccggacggagcaatttatactgtcggatctcctattgattacggtgtgatcgtggat
actaaagcttatagcggaggttataatctgccaattggccaagcagatgccatgcaaagctatgtcgaagaaaat
caaacacgaaacaaacatatcaaccctaatgatggtggaaagtctatccatcttctgtaacggaatttaagttt
ttatttgtgagtggtcactttaaaggaaactacaaagctcagcttacacgattaaatcatatcactaattgtaat
ggagctgttcttagtgtagaagagcttttaattggtggagaaatgattaaagccggcacattaaccttagaggaa
gtgagacggaaatttaataacggcgagataaactttctcgattag (SEQ ID NO: 3)

MVYPYDVPDYAELPPKKKRKVGIRIPGEKPYKCPDCGKSFSQSSSLIRHQRTHTGEKPYKCDECGKNFTQSSNLI
VHKRIHTGEKPYKCPECGKSFSQNSTLTEHQRTHTGEKPYECDHCGKAFSVSSNLNVHRRIHTGEKQLVKSELEE
KKSELRHKLKYVPHEYIELIEIARNPTQDRILEMKVMEFFMKVYGYRGEHLGGSRKPDGAIYTVGSPIDYGVIVD
TKAYSGGYNLPIGQADAMQSYVEENQTRNKHINPNEWWKVYPSSVTEFKFLFVSGHFKGNYKAQLTRLNHITNCN
GAVLSVEELLIGGEMIKAGTLTLEEVRRKFNNGEINFLD (SEQ ID NO: 4)

[Figure 2]

atggcctcctccgaggacgtcatcaaggagttcatgcgcttcaaggtgcgcatggagggctccgtgaacggccac
gagttcgagatcgagggcgagggcgagggccgcccctacgagggcacccagaccgccaagctgaaggtgaccaag
ggcggccccctgcccttcgcctgggacatcctgtcccctcagttccagtacggctccaaggcctacgtgaagcac
cccgccgacatccccgactacttgaagctgtccttccccgagggcttcaagtgggagcgcgtgatgaacttcgag
gacggcggcgtggtgaccgtgacccaggactcctccctgcaggacggcgagttcatctacaaggtgaagctgcgc
ggcaccaacttccccctccgacggccccgtaatgcagaagaagaccatgggctgggaggcctccaccgagcggatg
taccccgaggacggcgccctgaagggcgagatcaagatgaggctgaagctgaaggacggcggccactacgacgcc
gaggtcaagaccacctacatggccaagaagcccgtgcagctgcccggcgcctacaagaccgacatcaagctggac
atcacctccacaacgaggactacaccatcgtggaacagtacgagcgcgccgagggccgccactccaccggcgcc
gaatt<u>ggcgtccggccatggccatctacaagcag</u>tcacagcaggatccagtgagcaagggcgaggagctgttca
ccggggtggtgcccatcctggtcgagctggacggcgacgtaaacggccacaagttcagcgtgtccggcgagggcg
agggcgatgccacctacggcaagctgaccctgaagttcatctgcaccaccggcaagctgcccgtgccctggccca
ccctcgtgaccaccctgacctacggcgtgcagtgcttcagccgctaccccgaccacatgaagcagcacgacttct
tcaagtccgccatgcccgaaggctacgtccaggagcgcaccatcttcttcaaggacgacggcaactacaagaccc
gcgccgaggtgaagttcgagggcgacaccctggtgaaccgcatcgagctgaagggcatcgacttcaaggaggacg
gcaacatcctggggcacaagctggagtacaactacaacagccacaacgtctatatcatggccgacaagcagaaga
acggcatcaaggtgaacttcaagatccgccacaacatcgaggacggcagcgtgcagctcgccgaccactaccagc
agaacacccccatcggcgacggccccgtgctgctgcccgacaaccactacctgagcacccagtccgccctgagca
aagaccccaacgagaagcgcgatcacatggtcctgctggagttcgtgaccgccgccgggatcactctcggcatgg
acgagctgtacaagtaa (SEQ ID NO: 29)

[Figure 3a]
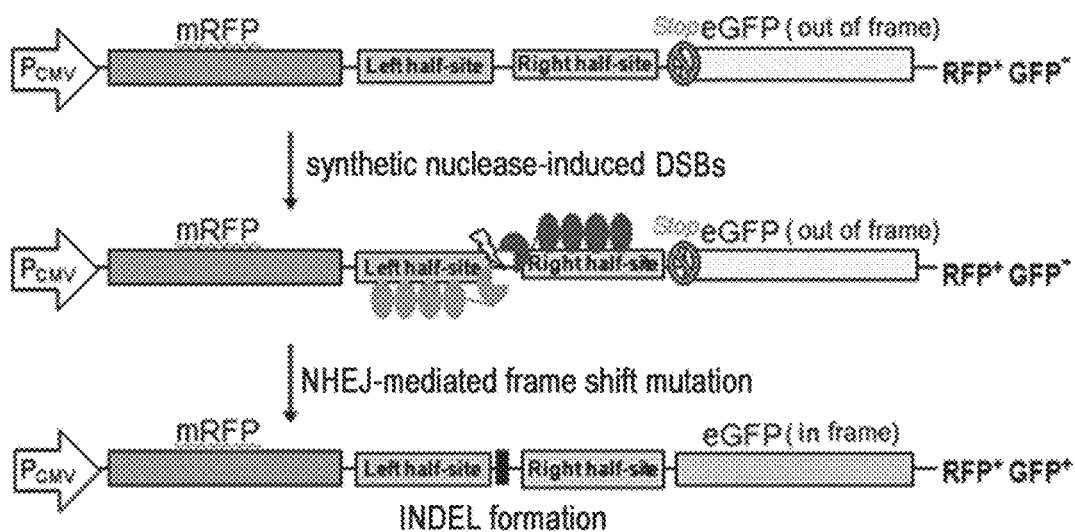

[Figure 3b]
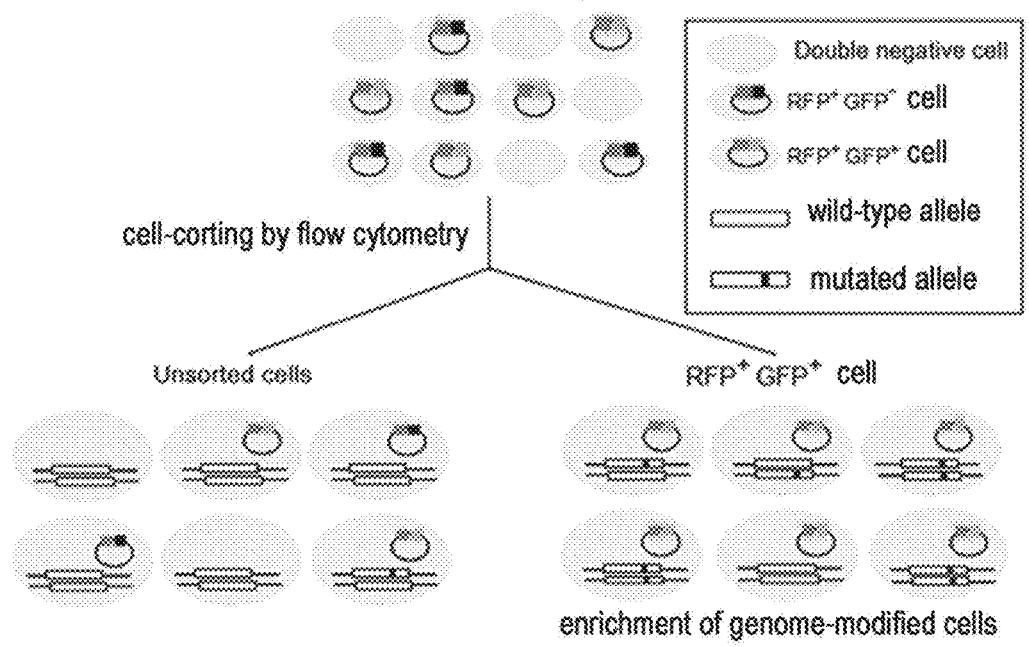

[Figure 5]
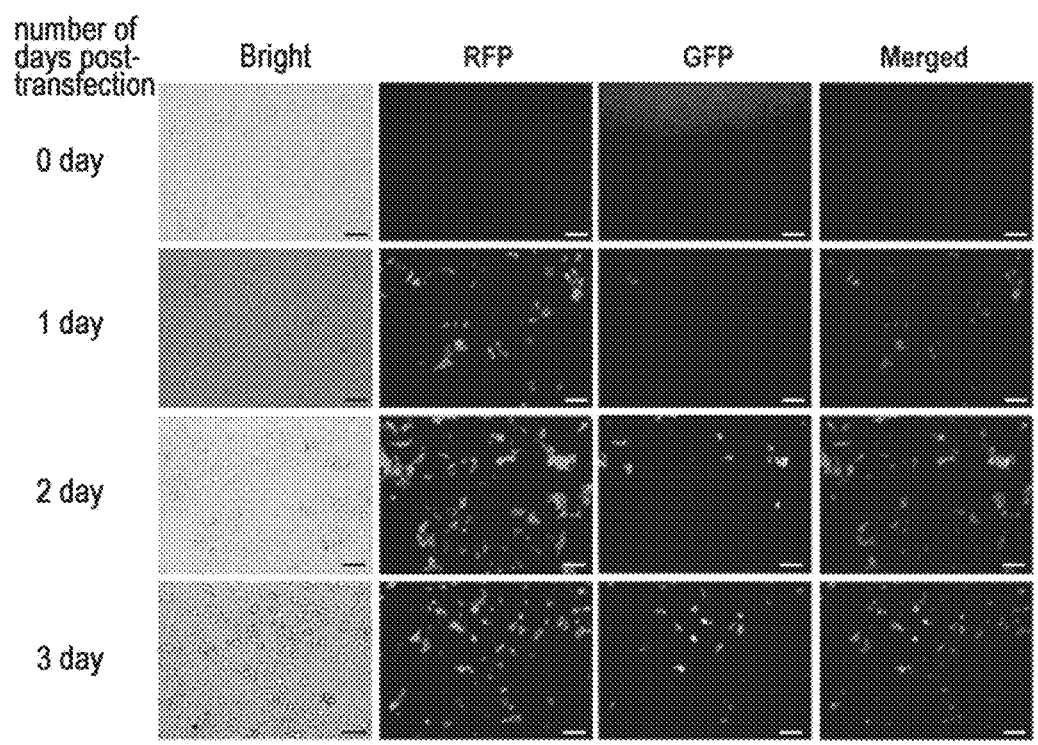

[Figure 6a]
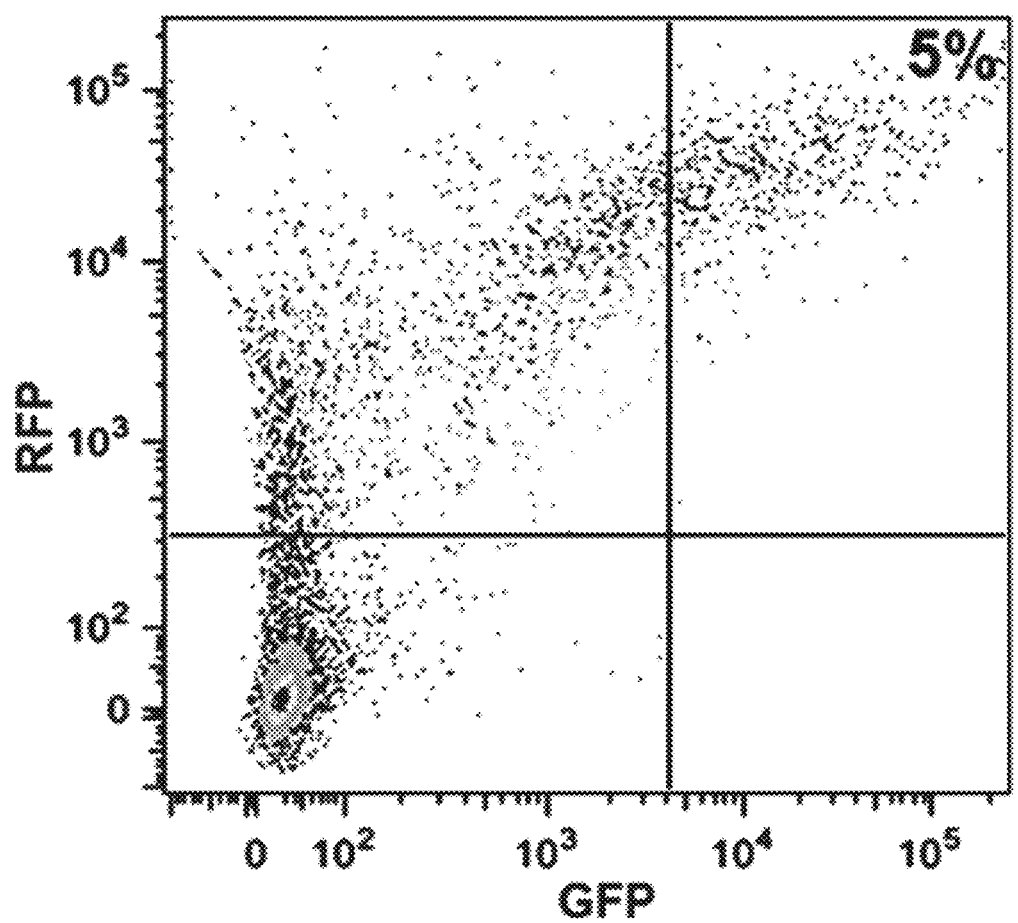

[Figure 6b]
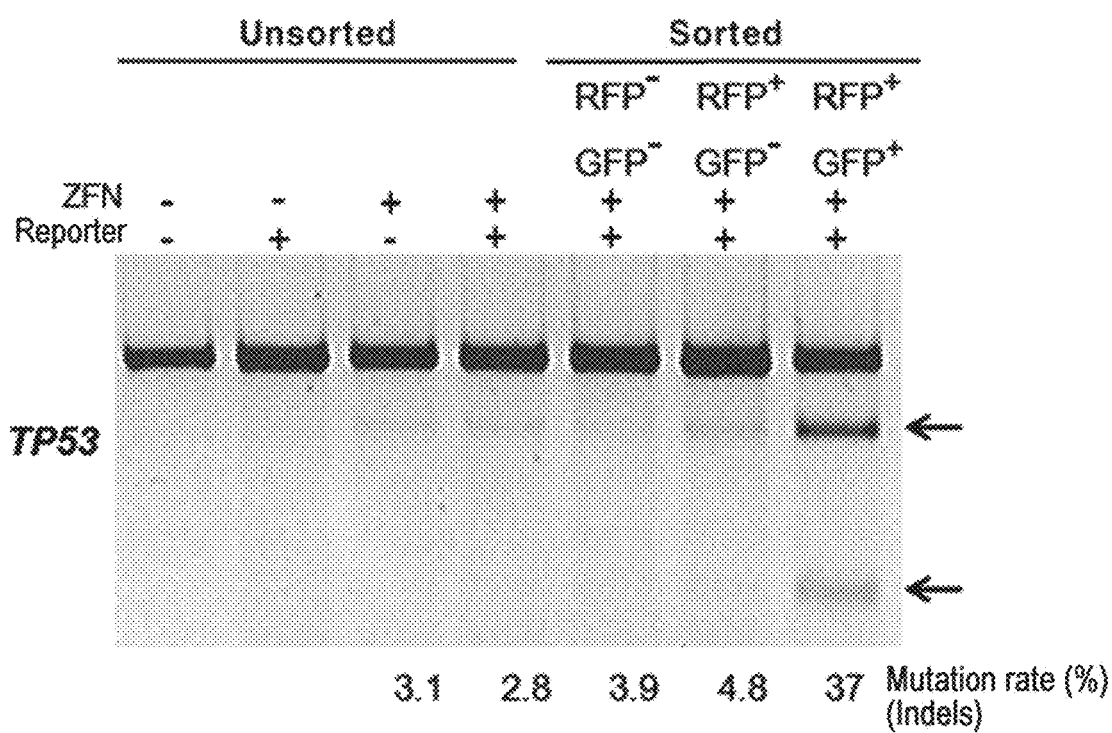

[Figure 6c]
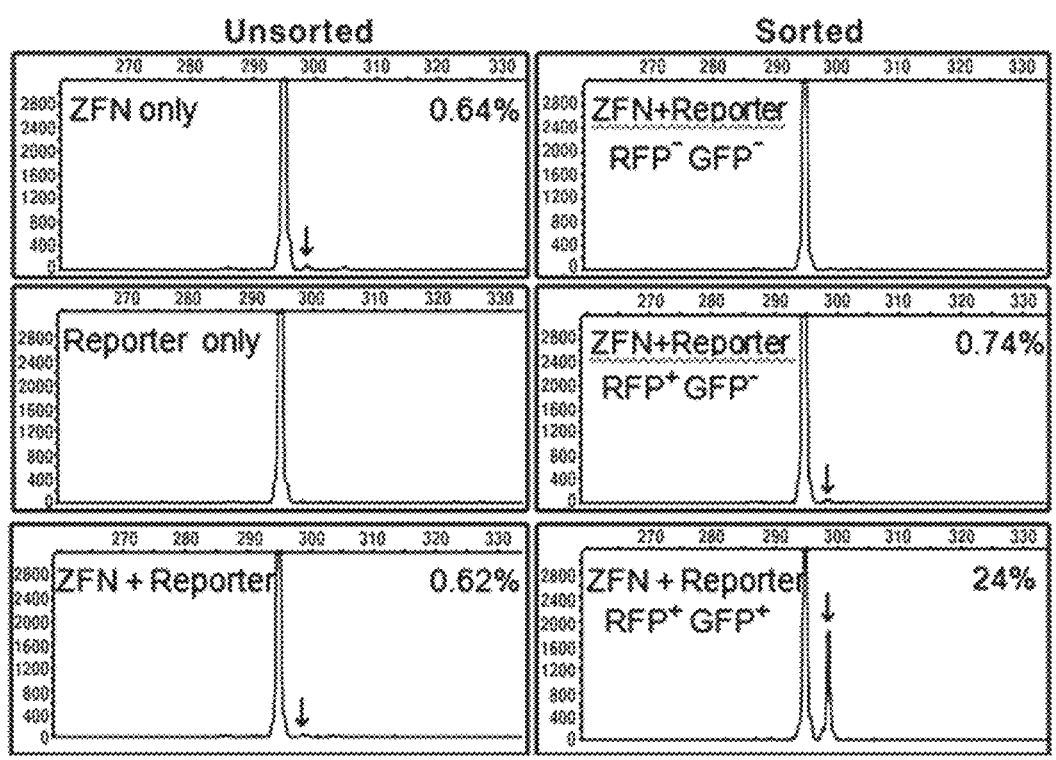

[Figure 6d]

Unsorted, 1.0%(=3/288) mutated

```
GGCACCCGCGTCCGCGCC-----ATGGCCATCTACAAGCAGTCAC  (WT)(SEQ ID NO: 56)
GGCACCCGCGTCCGCGCCatggtATGGCCATCTACAAGCAGTCAC  (X1)(SEQ ID NO: 57)
GGCACCCGCGTCCGCGCCatgg-ATGGCCATCTACAAGCAGTCAC  (X1)(SEQ ID NO: 58)
GGCACCCGCGTCCGCGCCat---ATGGCCATCTACAAGCAGTCAC  (X1)(SEQ ID NO: 59)
```

Sorted (RFP⁺GFP⁺), 20%(=8/40) mutated

```
GGCACCCGCGTCCGCGCC-----ATGGCCATCTACAAGCAGTCAC  (WT)(SEQ ID NO: 56)
GGCACCCGCGTCCGCGCCcatggATGGCCATCTACAAGCAGTCAC  (X1)(SEQ ID NO: 60)
GGCACCCGCGTCCGCGCC-atggATGGCCATCTACAAGCAGTCAC  (X5)(SEQ ID NO: 61)
GGCACCCGCGTCCGCGCC-at--ATGGCCATCTACAAGCAGTCAC  (X1)(SEQ ID NO: 62)
GGCACCCGCGTCCGCGCCc----ATGGCCATCTACAAGCAGTCAC  (X1)(SEQ ID NO: 63)
```

[Figure 7a]
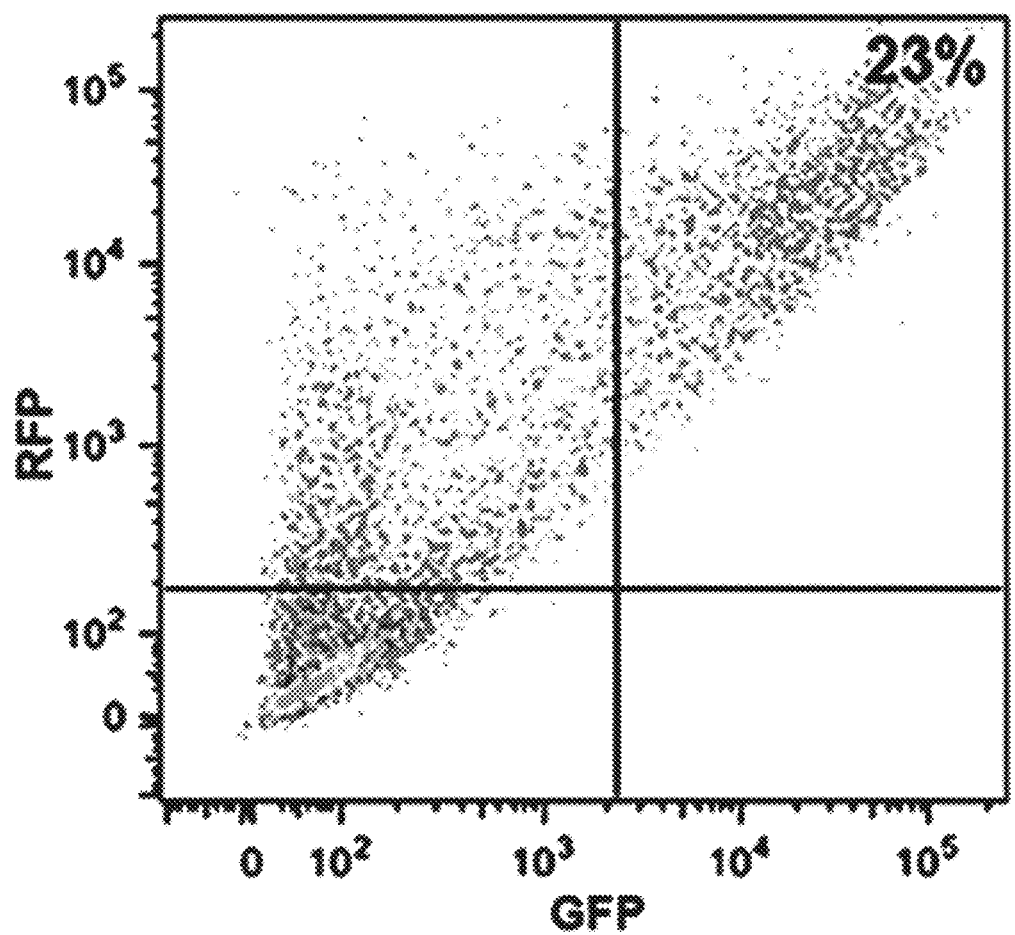

[Figure 7b]
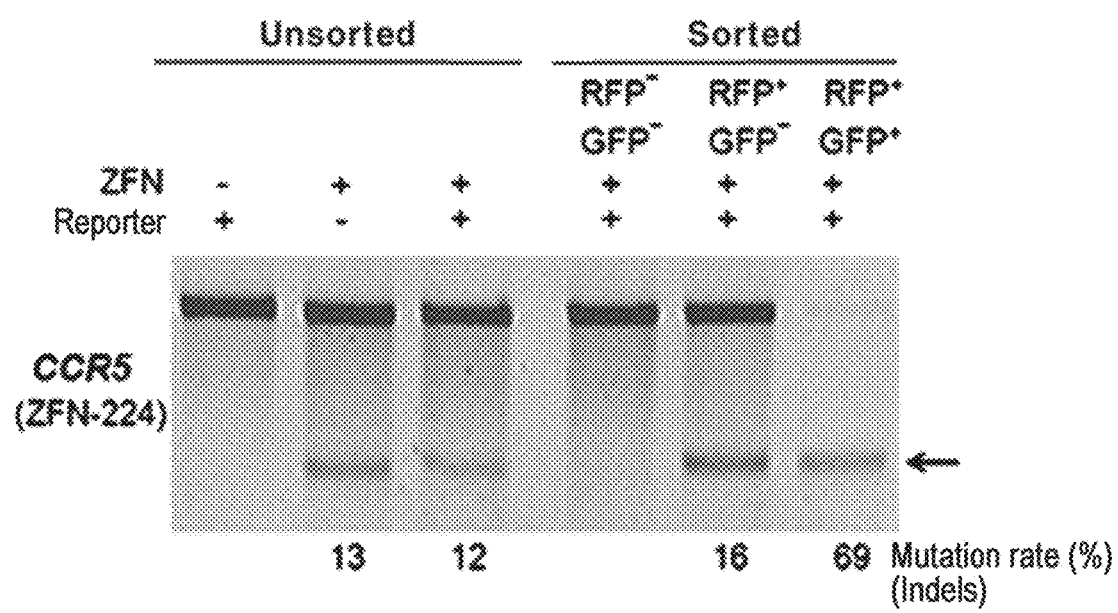

[Figure 7c]
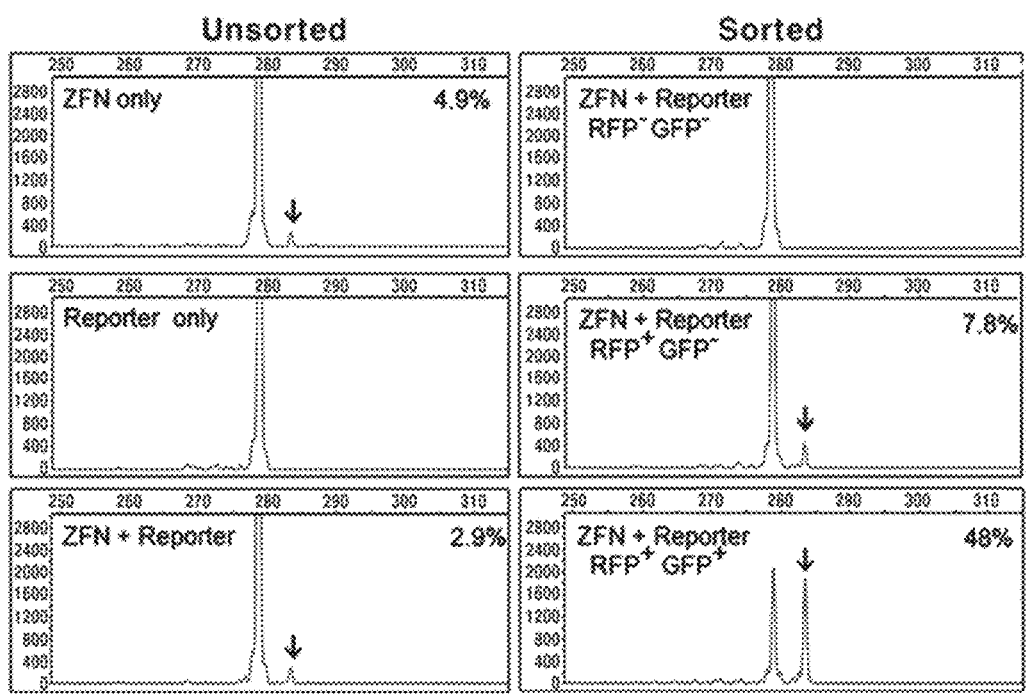

[Figure 8a]
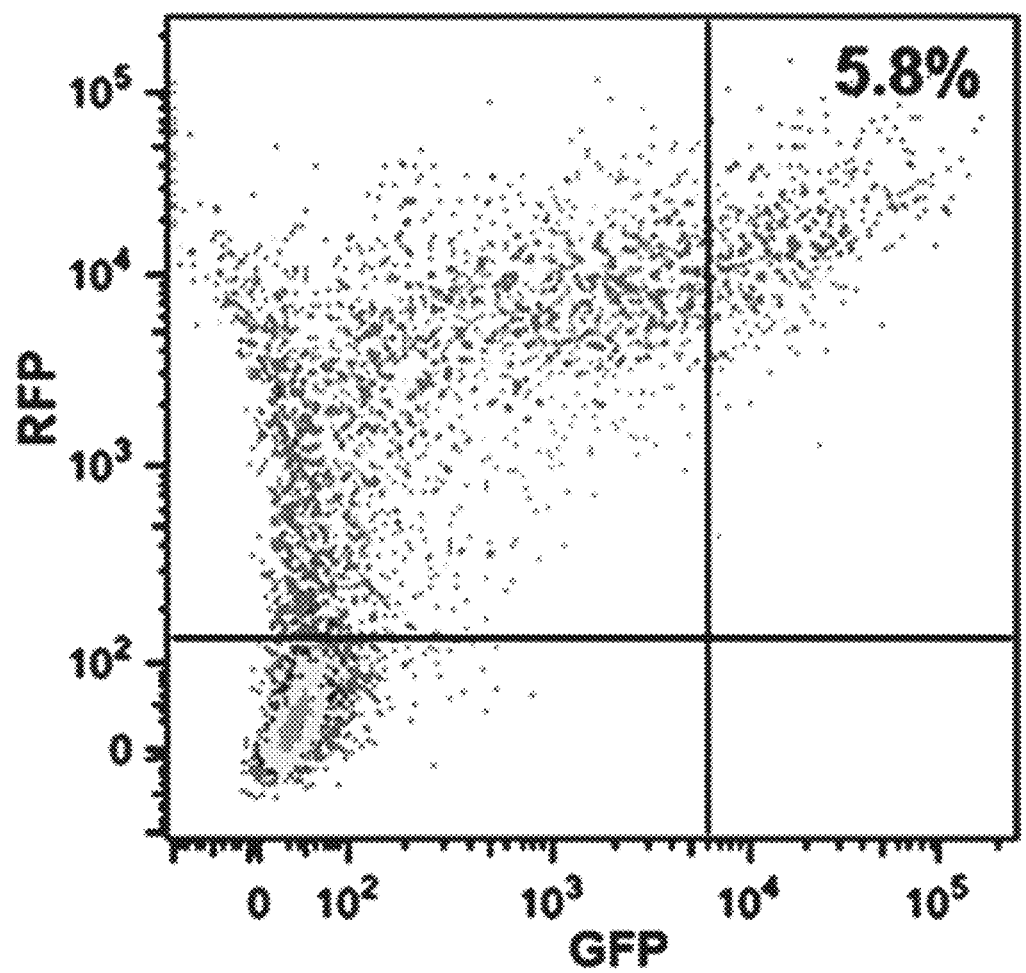

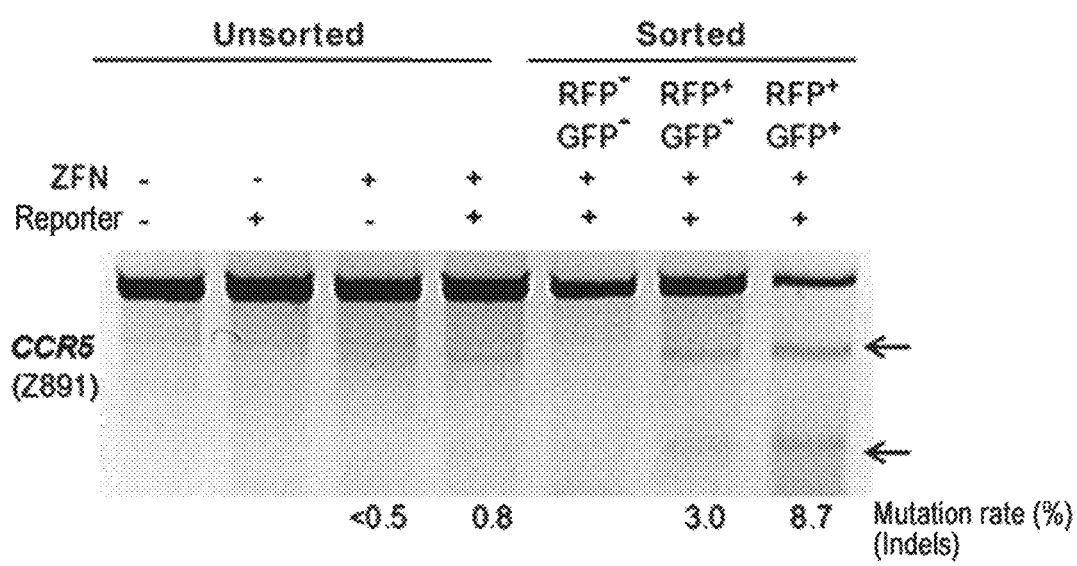
[Figure 8b]

[Figure 8c]
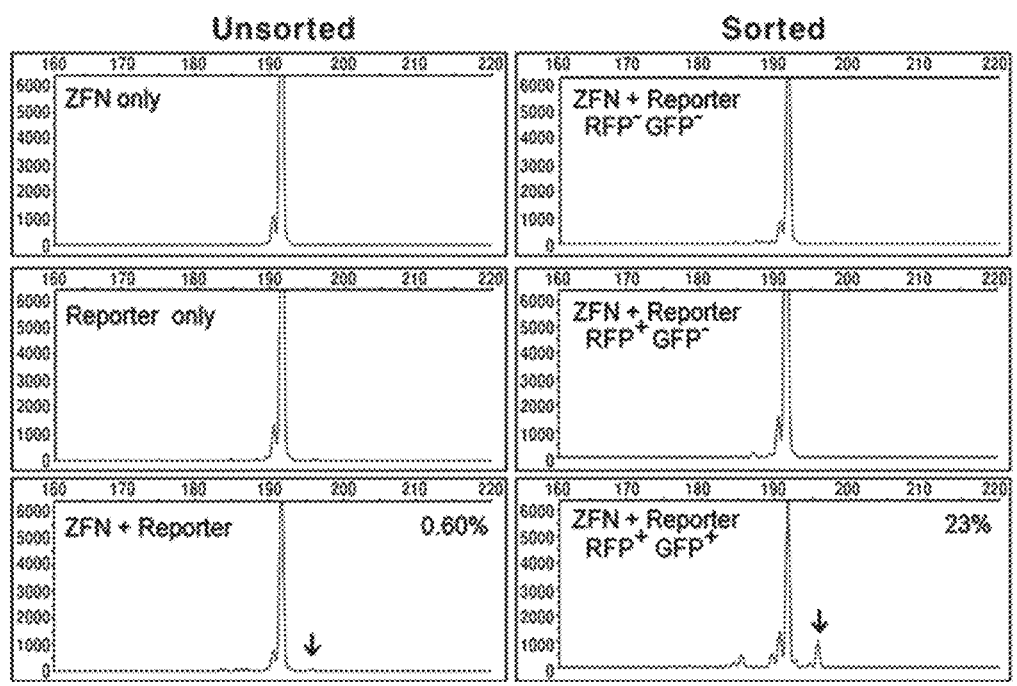

[Figure 9a]
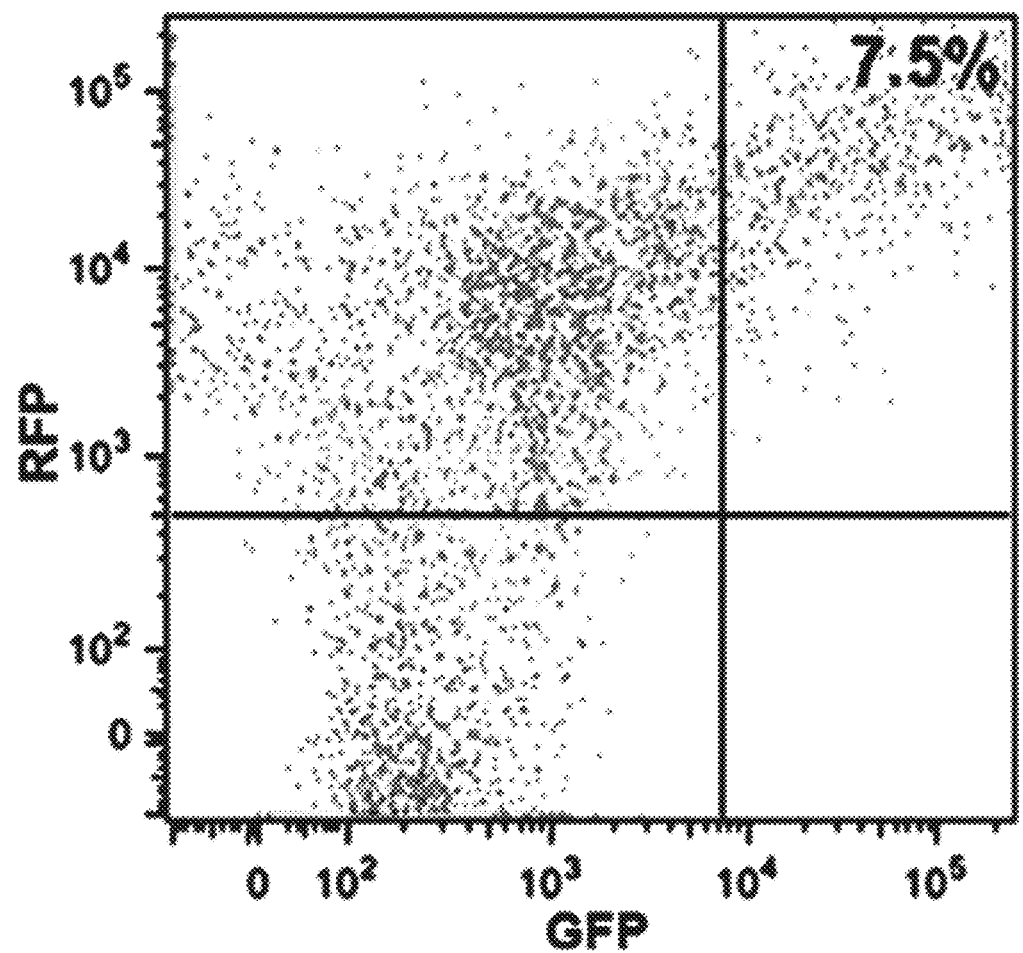

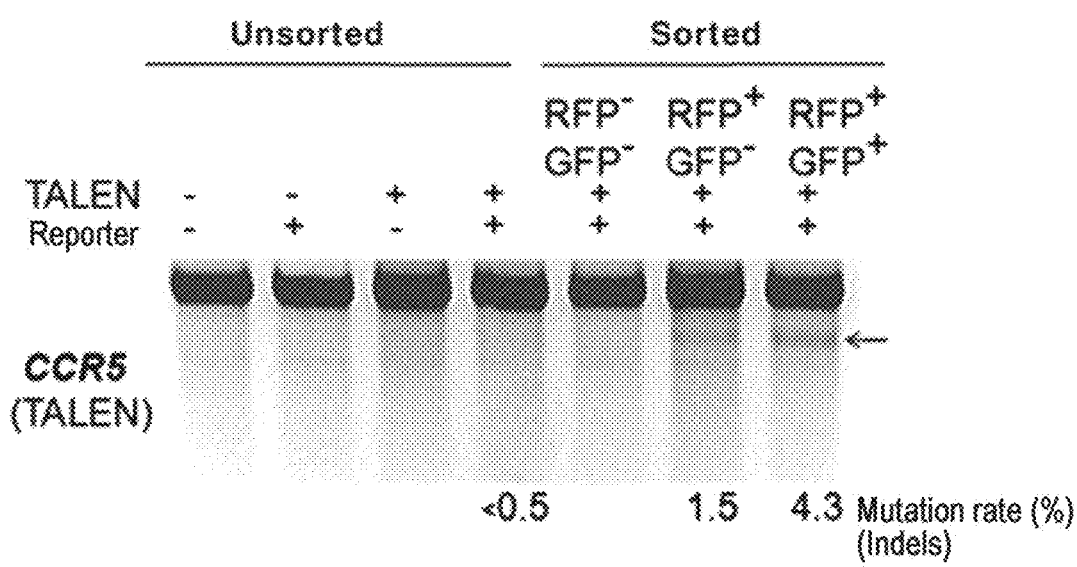
[Figure 9b]

[Figure 10a]
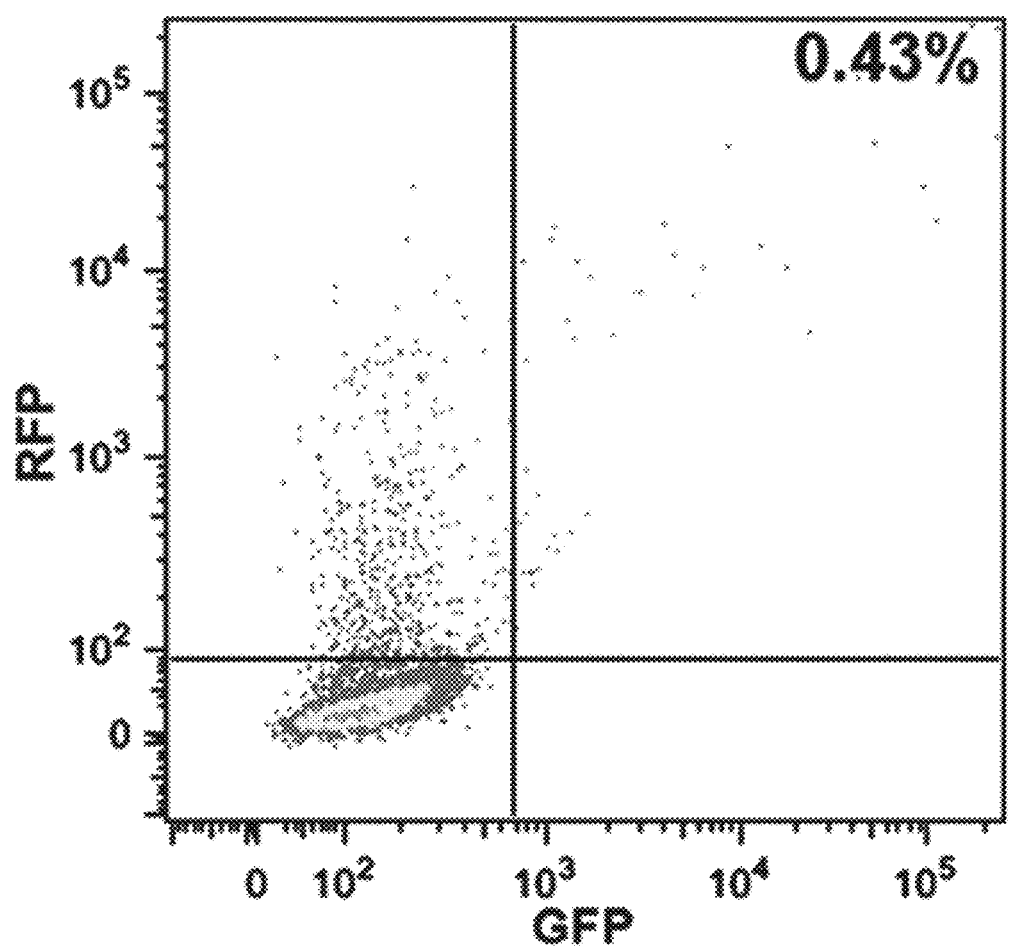

[Figure 10b]
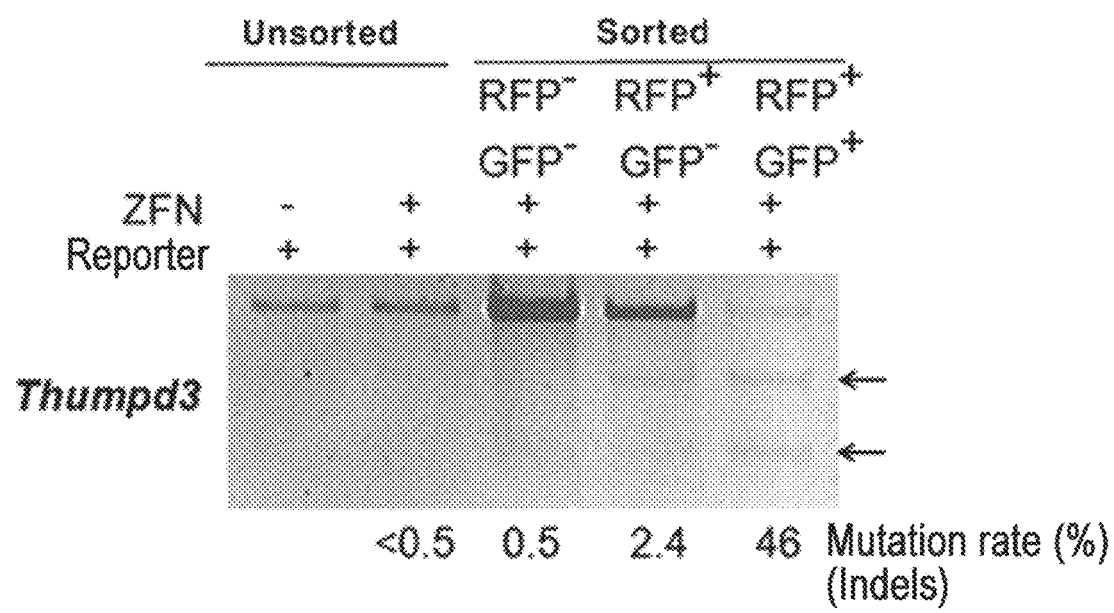

[Figure 1a]

Unsorted, 0%(=0/21)

sorted (RFP+GFP+), 90%(=9/10) mutated, 40%(=4/10) bi-alleleic mutation

| | | |
|---|---|---|
| wt | ...TCGGCTTCCGGGGGTGCTGCGGTCGGAGACCGGAAGGGTCTGTGCT... | (SEQ ID NO:64) |
| clone 1a | ...TCGGCTTCCGGGGGTGCTGCGG-----AGACCGGAAGGGTCTGTGCT... (5-bp deletion) | (SEQ ID NO:65) |
| clone 1b | ...TCGGCTTCCGGGGGTGCTGCG------AGACCGGAAGGGTCTGTGCT... (6-bp deletion) | (SEQ ID NO:66) |
| clone 4a | ...TCGGCTTCCGGGGGTGCTGCG-----GAGACCGGAAGGGTCTGTGCT... (5-bp deletion) | (SEQ ID NO:67) |
| clone 4b | ...TCGGCTTCCGGGGGTGCTG--------------GAAGGGTCTGTGCT... (14-bp deletion) | (SEQ ID NO:68) |
| clone 6a | ...TCGGCTTCCGGGGGTGCTGCGT--GGAGACCGGAAGGGTCTGTGCT... (2-bp deletion) | (SEQ ID NO:69) |
| clone 6b | ...TCGGCTTCCGGGGGTGC---------GGAGACCGGAAGGGTCTGTGCT... (9-bp deletion) | (SEQ ID NO:70) |
| clone 7a | ...TCGGCTTCCGGGGGTGCTG---TCGGAGACCGGAAGGGTCTGTGCT... (3-bp deletion) | (SEQ ID NO:71) |
| clone 7b | ...TCGGCTTCCGGGGGTGCTG-----CGGAGACCGGAAGGGTCTGTGCT... (5-bp deletion) | (SEQ ID NO:72) |
| clone 3 | ...TCGGCTTCCGGGGGTGCTGCG---CGGAGACCGGAAGGGTCTGTGCT... (3-bp deletion) | (SEQ ID NO:73) |
| clone 2 | 322-bp deletion | |

[Figure 1b]

Unsorted, 0%(=0/41)

Sorted(RFP⁺GFP⁺), 33% (= 2/6) mutated wt      ...TCGGCTTCCGGCGGCGTGCTCGCGGTGCGGAGACCGGAAGGGTCTGTGCT...          (SEQ ID NO: 64)

clone 1 ...TCGGCTTCCGGCGGCGTGCTCGC--TGCGGAGACCGGAAGGGTCTGTGCT...(2-bp deletion) (SEQ ID NO: 74)

clone 2                205-bp deletion

[Figure 12a]
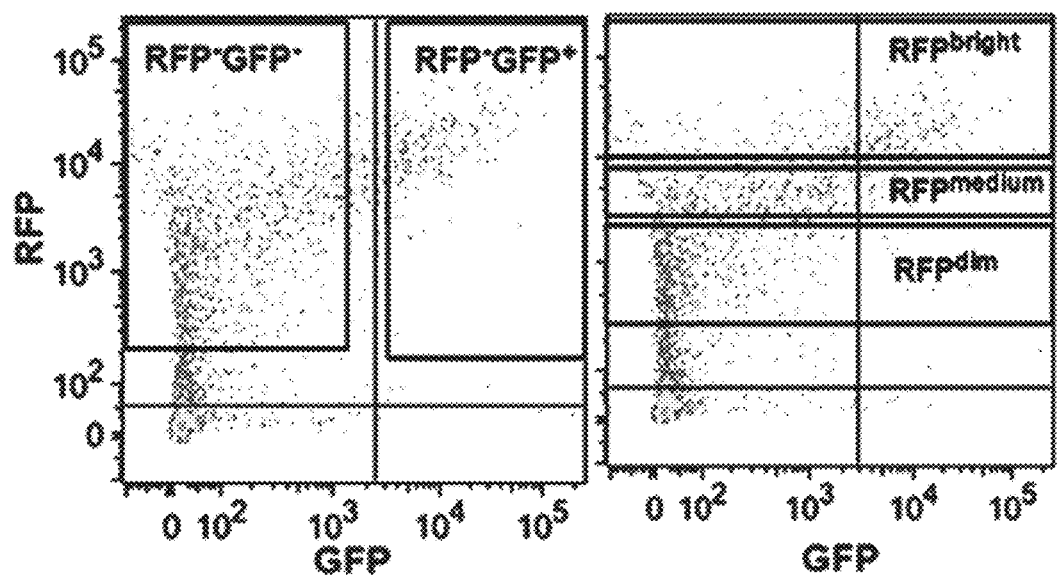
[Figure 12b]
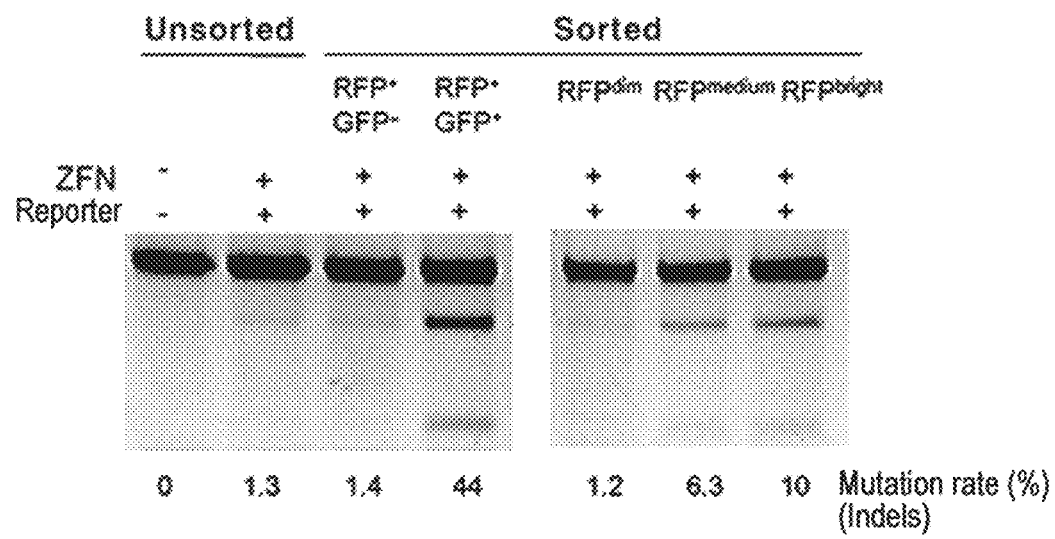

[Figure 12c]
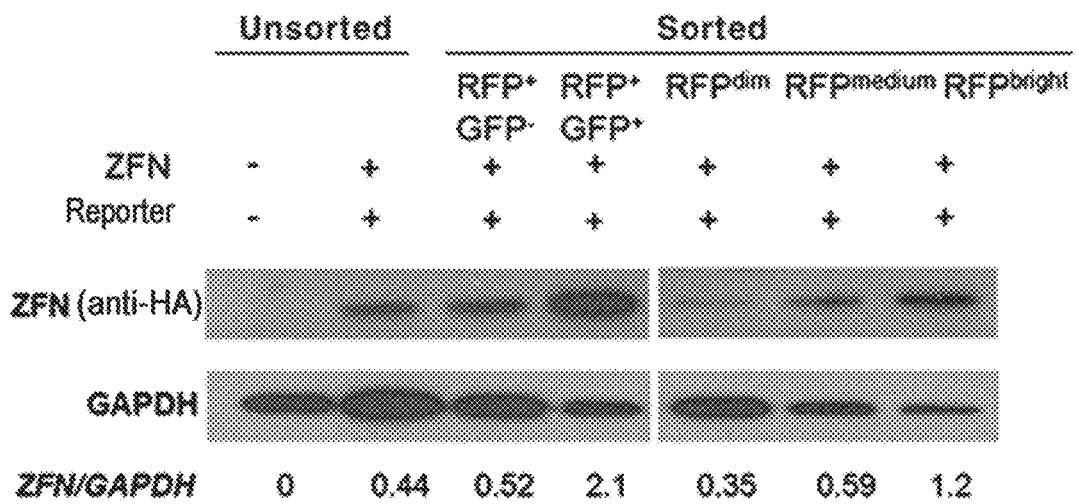
[Figure 13]
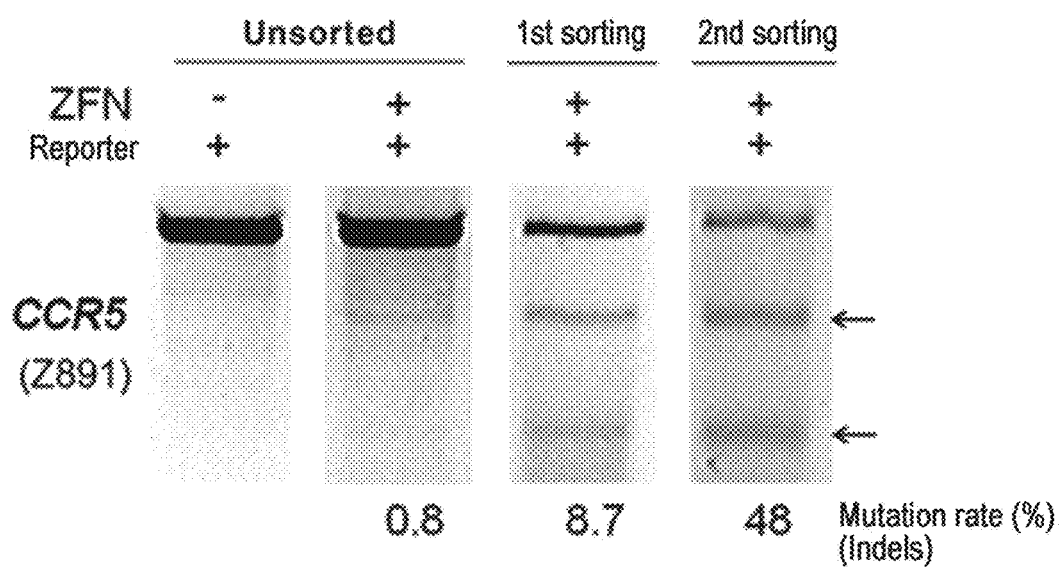

[Figure 14a]
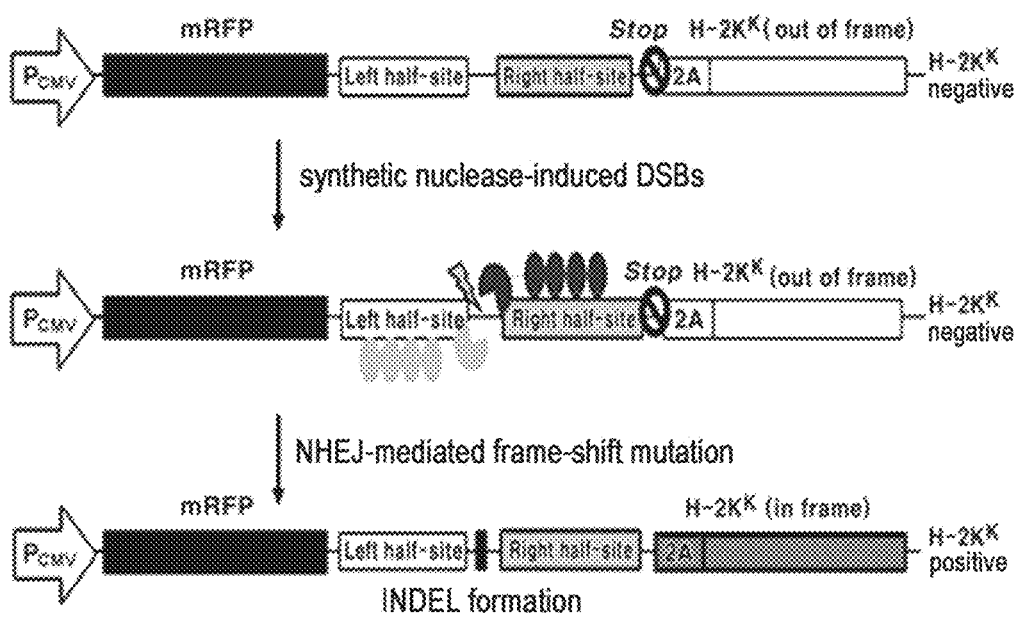

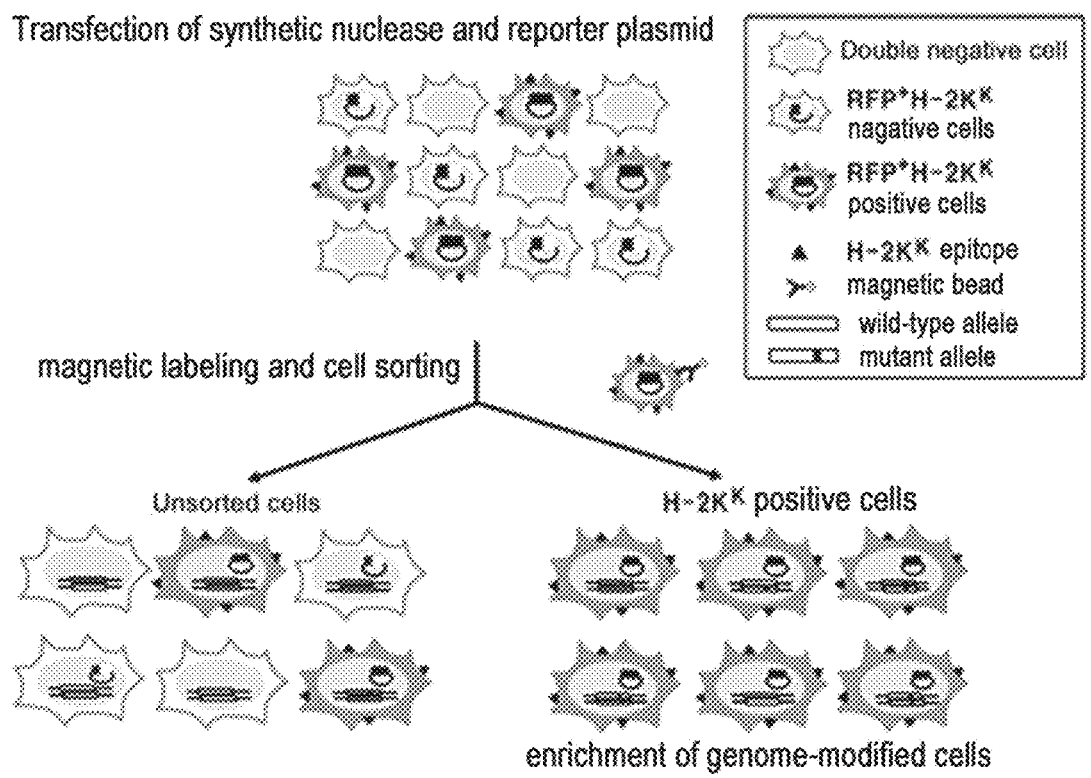
[Figure 14b]

[Figure 15]
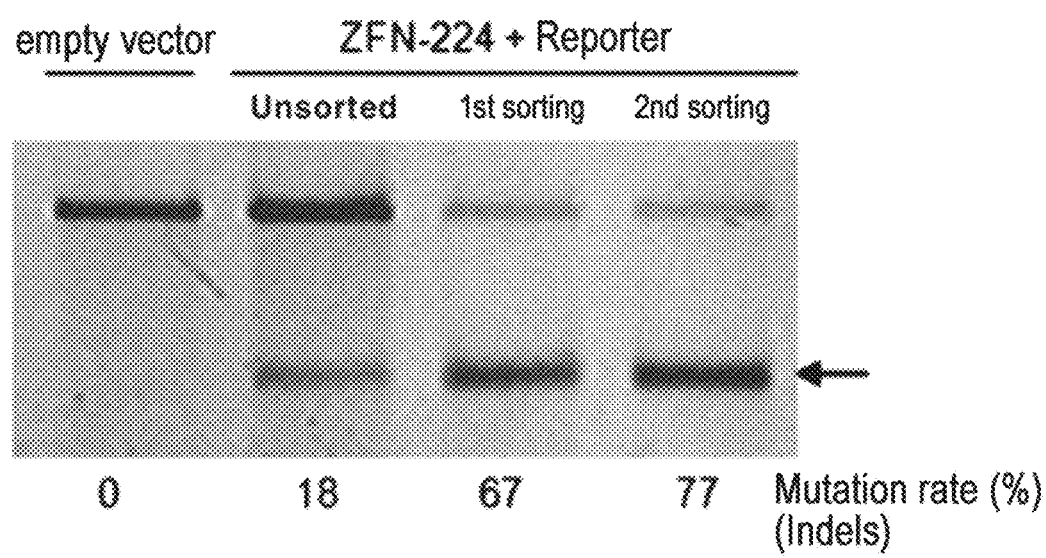

[Figure 16]

A TALEN double frame reporter DNA sequence:

atggcctcctccgaggacgtcatcaaggagttcatgcgcttcaaggtgcgcatggagggctccgtgaacggccacgagttc
gagatcgagggcgagggcgagggccgcccctacgagggcacccagaccgccaagctgaaggtgaccaagggcggccc
cctgccctcgcctgggacatcctgtcccctcagttccagtacggcccaaggcctacgtgaagcacccccgccgacatcccc
gactacttgaagctgtccttccccgagggcttcaagtgggagcgcgtgatgaacttcgaggacggcggcgtggtgaccgtg
acccaggacctccctgcaggacggcgagttcatctacaaggtgaagctgcgcggcaccaactccctccgacggcccc
gtaatgcagaagaagaccatgggctgggaggcctccaccgagcggatgtaccccgaggacggcgcctgaagggcgag
atcaagatgaggctgaagctgaaggacggcggccactacgacgccgaggtcaagaccacctacatggccaagaagcccg
tgcagctgccccggcgcctacaagaccgacatcaagctggacatcacctcccacaacgaggactacaccatcgtggaacag
tacgagcgcgccgagggccgccactccaccggcgccgaattc*tcgaggtggctccacatggtggaggctgg*
                                                                    target sequence
*ggtgaggccgagggctgg*gatccagtgagcaagggcgaggagctgttcaccggggtggtgcccatcctggtcgagctgg
acggcgacgtaaacggccacaagttcagcgtgtccggcgagggcgagggcgatgccacctacggcaagctgaccctgaa
gttcatctgcaccaccggcaagctgcccgtgccctggcccaccctcgtgaccaccctgacctacggcgtgcagtgcttcagc
cgctaccccgaccacatgaagcagcacgacttcttcaagtccgccatgcccgaaggctacgtccaggagcgcaccatcttct
tcaaggacgacggcaactacaagacccgcgccgaggtgaagttcgagggcgacaccctggtgaaccgcatcgagctgaa
gggcatcgacttcaaggaggacggcaacatcctggggcacaagctggagtacaactacaacagccacaacgtctatatcat
ggccgacaagcagaagaacggcatcaaggtgaacttcaagatccgccacaacatcgaggacggcagcgtgcagctcgcc
gaccactaccagcagaacacccccatcggcgacggccccgtgctgctgcccgacaaccactacctgagcacccagtccgc
cctgagcaaagaccccaacgagaagcgcgatcacatggtcctgctggagttcgtgaccgccgcgggatcactctcggcat
ggacgagctgtacaagtaaagcggccgccagtgagcaagggcgaggagctgttcaccggggtggtgcccatcctggtcga
gctggacggcgacgtaaacggccacaagttcagcgtgtccggcgagggcgagggcgatgccacctacggcaagctgacc
ctgaagttcatctgcaccaccggcaagctgcccgtgccctggcccaccctcgtgaccaccctgacctacggcgtgcagtgct
tcagccgctaccccgaccacatgaagcagcacgacttcttcaagtccgccatgcccgaaggctacgtccaggagcgcacc
atcttcttcaaggacgacggcaactacaagacccgcgccgaggtgaagttcgagggcgacaccctggtgaaccgcatcga
gctgaagggcatcgacttcaaggaggacggcaacatcctggggcacaagctggagtacaactacaacagccacaacgtct
atatcatggccgacaagcagaagaacggcatcaaggtgaacttcaagatccgccacaacatcgaggacggcagcgtgcag
ctcgccgaccactaccagcagaacacccccatcggcgacggccccgtgctgctgcccgacaaccactacctgagcaccca
gtccgccctgagcaaagaccccaacgagaagcgcgatcacatggtcctgctggagttcgtgaccgccgccgggatcactct
cggcatggacgagctgtacaagtaa. (SEQ ID NO: 52)

[Figure 17]

B TALEN double frame reporter DNA sequence :
atggcctcctccgaggacgtcatcaaggagttcatgcgcttcaaggtgcgcatggagggctccgtgaacggccacgagttc
gagatcgagggcgagggcgagggccgcccctacgagggcacccagaccgccaagctgaaggtgaccaaggcggccc
cctgcccttcgcctgggacatcctgtcccctcagttccagtacggctccaaggcctacgtgaagcacccggccgacatcccc
gactacttgaagctgtccttccccgagggcttcaagtggggagcgcgtgatgaacttcgaggacggcggcgtggtgaccgtg
acccaggactcctccctgcaggacggcgagttcatctacaaggtgaagctgcgcggcaccaacttccctccgacggcccc
gtaatgcagaagaagaccatgggctgggaggcctccaccgagcggatgtaccccgaggacggcgccctgaagggcgag
atcaagatgaggctgaagctgaaggacggcggccactacgacgccgaggtcaagaccacctacatggccaagaagcccg
tgcagctgccggcgcctacaagaccgacatcaagctggacatcacctcccacaacgaggactacaccatcgtggaacag
tacgagcgcgccgagggccgccactccaccggcgccgaattc*tcgacttacggcgtcaccgcggacggcttcgcgc*
                                                                    target sequence
*tactggccggacaacgccc*ggatccagtgagcaagggcgaggagctgttcaccggggtggtgcccatcctggtcgagctg
gacggcgacgtaaacggccacaagttcagcgtgtccggcgagggcgagggcgatgccacctacggcaagctgaccctga
agttcatctgcaccaccggcaagctgcccgtgccctggcccaccctcgtgaccaccctgacctacggcgtgcagtgcttcag
ccgctaccccgaccacatgaagcagcacgacttcttcaagtccgccatgcccgaaggctacgtccaggagcgcaccatctt
cttcaaggacgacggcaactacaagacccgcgccgaggtgaagttcgagggcgacaccctggtgaaccgcatcgagctga
agggcatcgacttcaaggaggacggcaacatcctggggcacaagctggagtacaactacaacagccacaacgtctatatca
tggccgacaagcagaagaacggcatcaaggtgaacttcaagatccgccacaacatcgaggacggcagcgtgcagctcgc
cgaccactaccagcagaacaccccccatcggcgacggccccgtgctgctgcccgacaaccactacctgagcacccagtccg
ccctgagcaaagaccccaacgagaagcgcgatcacatggtcctgctggagttcgtgaccgccgcgggatcactctcggc
atggacgagctgtacaagtaaagcggccgccagtgagcaagggcgaggagctgttcaccggggtggtgcccatcctggtc
gagctggacggcgacgtaaacggccacaagttcagcgtgtccggcgagggcgagggcgatgccacctacggcaagctga
ccctgaagttcatctgcaccaccggcaagctgcccgtgccctggcccaccctcgtgaccaccctgacctacggcgtgcagt
gcttcagccgctaccccgaccacatgaagcagcacgacttcttcaagtccgccatgcccgaaggctacgtccaggagcgca
ccatcttcttcaaggacgacggcaactacaagacccgcgccgaggtgaagttcgagggcgacaccctggtgaaccgcatc
gagctgaagggcatcgacttcaaggaggacggcaacatcctggggcacaagctggagtacaactacaacagccacaacgt
ctatatcatggccgacaagcagaagaacggcatcaaggtgaacttcaagatccgccacaacatcgaggacggcagcgtgc
agctcgccgaccactaccagcagaacacccccatcggcgacggccccgtgctgctgcccgacaaccactacctgagcacc
cagtccgccctgagcaaagaccccaacgagaagcgcgatcacatggtcctgctggagttcgtgaccgccgccgggatcac
tctcggcatggacgagctgtacaagtaa. (SEQ ID NO: 53)

[Figure 18]
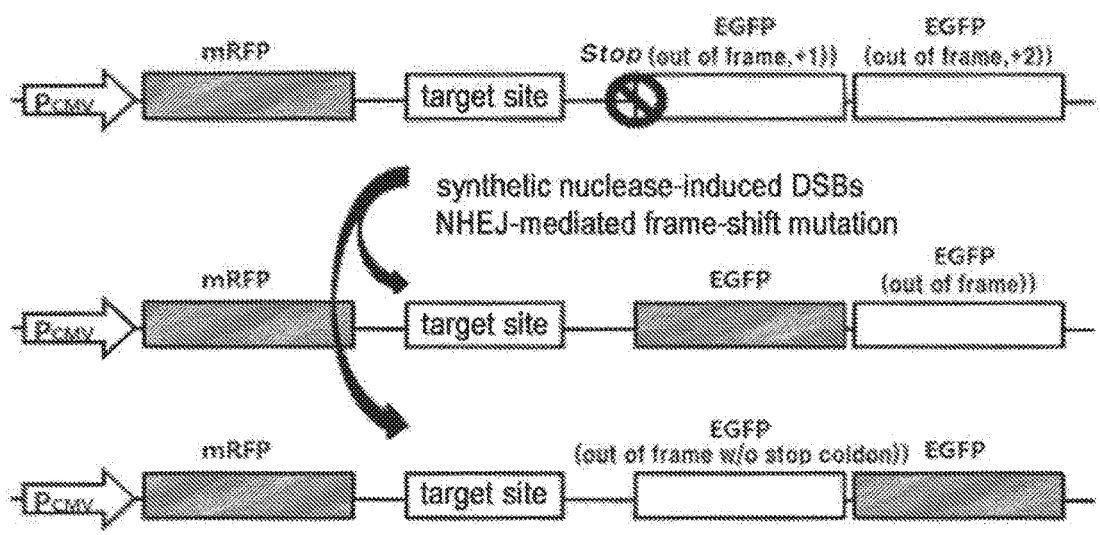

[Figure 19]
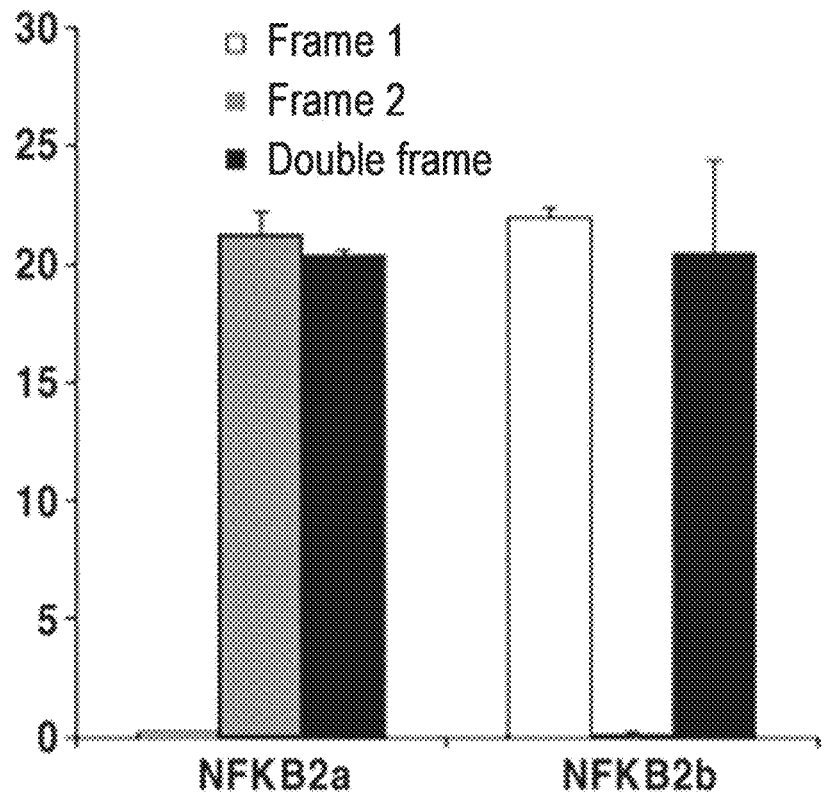
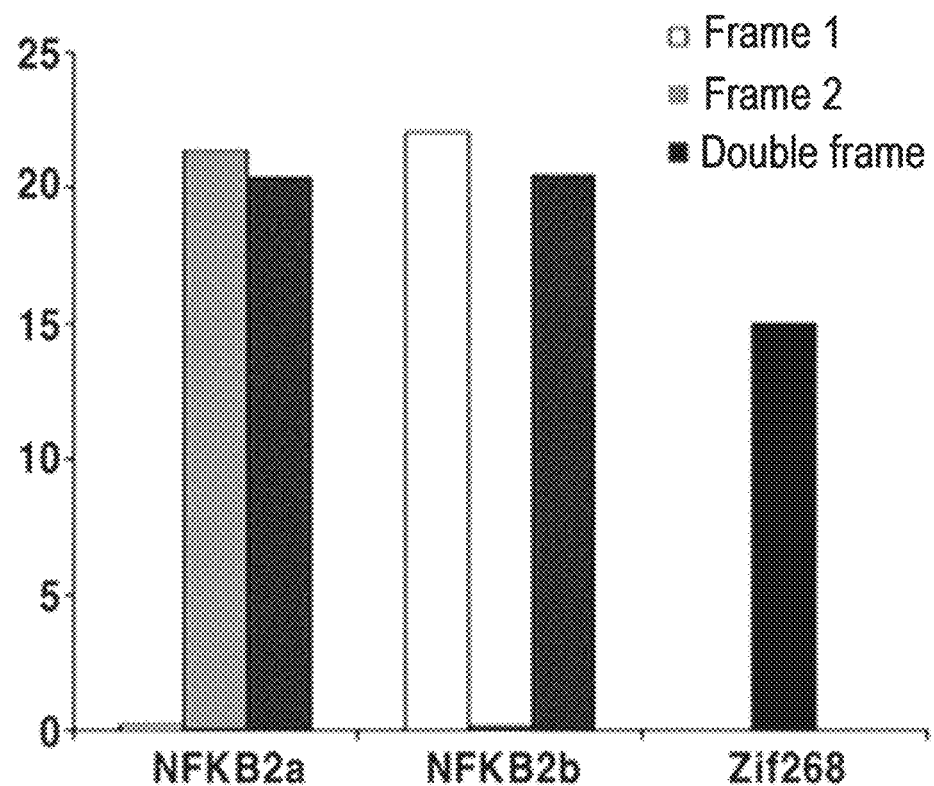

[Figure 20]
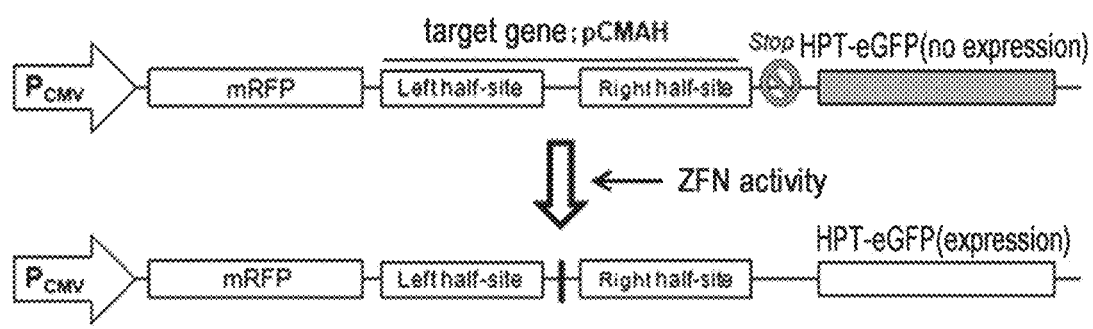

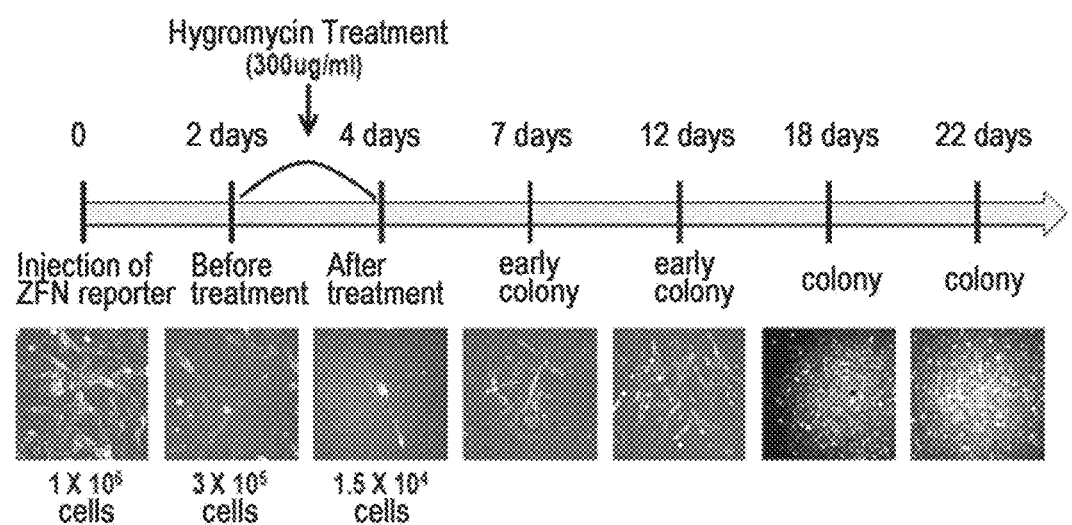
[Figure 21]

[Figure 22]
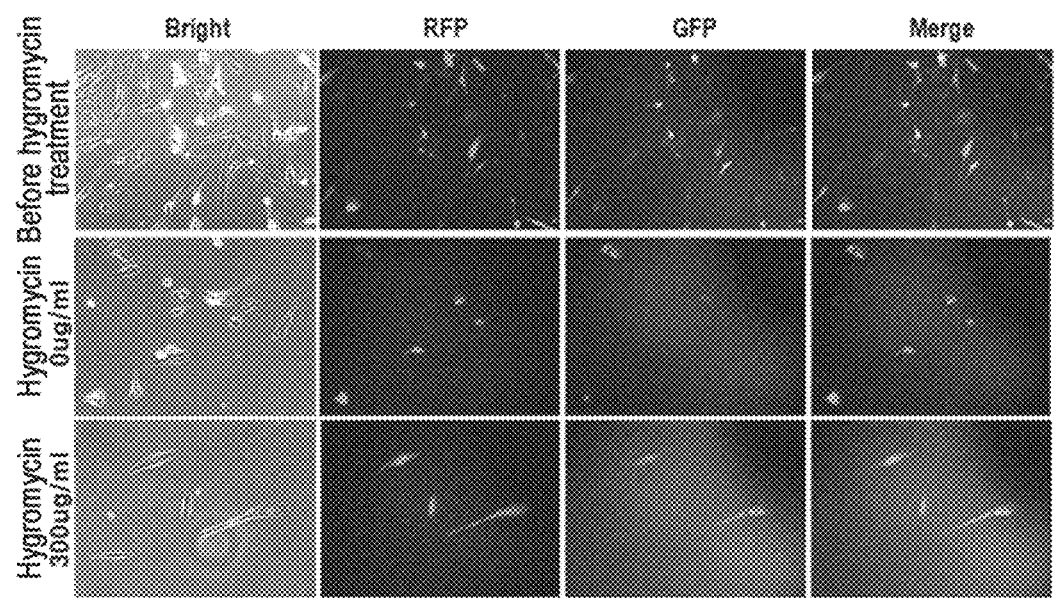
[Figure 23]
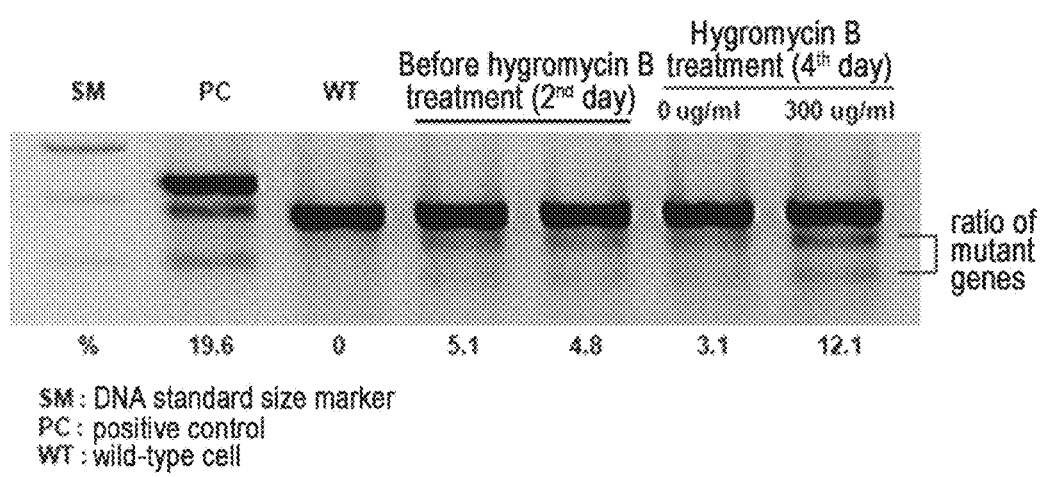
SM : DNA standard size marker
PC : positive control
WT : wild-type cell

[Figure 24]

atggcctcctccgaggacgtcatcaaggagttcatgcgcttcaaggtgcgcatggagggctccgtgaacggccacgagttc
gagatcgagggcgagggcgagggccgcccctacgagggcacccagaccgccaagctgaaggtgaccaagggcggccc
cctgcccttcgcctgggacatcctgtcccctcagttccagtacggctccaaggcctacgtgaagcaccccgccgacatccc
gactacttgaagctgtccttccccgagggcttcaagtggagcgcgtgatgaacttcgaggacggcggcgtggtgaccgtg
acccaggactcctccctgcaggacggcgagttcatctacaaggtgaagctgcgcggcaccaacttcccctccgacggcccc
gtaatgcagaagaagaccatgggctggaggcctccaccgagcggatgtaccccgaggacggcgccctgaagggcgag
atcaagatgaggctgaagctgaaggacggcggccactacgacgccgaggtcaagaccacctacatggccaagaagcccg
tgcagctgcccggcgcctacaagaccgacatcaagctggacatcacctccacaacgaggactacaccatcgtggaacag
tacgagcgcgccgagggccgccactccaccggcgccgaattc<u>tcggtcctgcttttgcgcgaggatggtggt</u>gaaggatcc
                                                           CMAH-ZFN- target sequence
agtgagcaagggcgaggagctgttcaccggggtggtgcccatcctggtcgagctggacggcgacgtaaacggccacaagt
tcagcgtgtccggcgagggcgagggcgatgccacctacggcaagctgaccctgaagttcatctgcaccaccggcaagctg
cccgtgccctggcccaccctcgtgaccaccctgacctacggcgtgcagtgcttcagccgctaccccgaccacatgaagcag
cacgacttcttcaagtccgccatgcccgaaggctacgtccaggagcgcaccatcttcttcaaggacgacggcaactacaag
acccgcgccgaggtgaagttcgagggcgacaccctggtgaaccgcatcgagctgaagggcatcgacttcaaggaggacg
gcaacatcctggggcacaagctggagtacaactacaacagccacaacgtctatatcatggccgacaagcagaagaacggc
atcaaggtgaacttcaagatccgccacaacatcgaggacggcagcgtgcagctcgccgaccactaccagcagaacacccc
catcggcgacggccccgtgctgctgcccgacaaccactacctgagcacccagtccgccctgagcaaagaccccaacgag
aagcgcgatcacatggtcctgctggagttcgtgaccgccgcgggatcactctcggcatggacgagctgtacaag<u>caatgta</u>
<u>ctaactacgctttgttgaaactcgctggcgatgttgaaagtaaccccggtcctgct</u>agcatggcaccctgcatgctgctcctgct
        2A-peptide nucleotide sequence
gttggcggccgccctggccccgactcagacccgcgcgggcccacattcgctgaggtatttccacaccgccgtgtcccggcc
cggcctcgggaagccccggttcatctctgtcggctacgtggacgacacgcagttcgtgcgcttcgacagcgacgcggagaa
tccgaggtatgagccgcgggtgcggtggatggagcaggtggagcccgagtatgggagcggaacacgcagatcgccaag
ggcaatgagcagatttcgagtgaacctgaggaccgcgctgcgctactacaaccagagcgcgggcggctctcacacgttc
caacggatgtacggctgtgaggtggggtcggactggcgcctcctccgcgggtacgagcagtacgcatacgacggctgcga
ttacatcgccctgaacgaagacctgaaaacgtggacggcggccgacatggcggcgctgatcaccaaacacaagtgggagc
aggctggtgatgcagagagagaccgggcctacctggagggcacgtgcgtggagtggctccgcagatacctgcagctcggg
aacgcgacgctgcgcgcacagattccccaaaggcccatgtgacccgtcacagcagacctgaagataaagtcaccctgag
gtgctgggccctgggcttctaccctgctgacatcacctgacctggcagttgaatggggaggagctgacccaggacatgga
gcttgtggagaccaggcctgcaggggatgaaccttccagaagtgggcatctgtggtggtgcctcttgggaaggagcagtat
tacacatgccatgtgtaccatcagggctgcctgagcccctcaccctgagatgggagcctcctccatccactgtctccaacac
ggtaatcatgctgttctggttgtccttggagctgcaatagtcactggagctgtggtggcttttgtgatgaagatgagaaggaga
aacacaggtggaaaaggagggtaa (SEQ ID NO: 54)

[Figure 25]

atggcctcctccgaggacgtcatcaaggagttcatgcgcttcaaggtgcgcatggagggctccgtgaacggccacgagttc
gagatcgagggcgagggcgagggccgcccctacgagggcacccagaccgccaagctgaaggtgaccaagggcggccc
cctgcccttcgcctgggacatcctgtcccctcagttccagtacggctccaaggcctacgtgaagcaccccgccgacatccc
gactactgaagctgtccttccccgagggcttcaagtgggagcgcgtgatgaacttcgaggacggcggcgtggtgaccgtg
acccaggactcctccctgcaggacggcgagttcatctacaaggtgaagctgcgcggcaccaacttcccctccgacggccc
gtaatgcagaagaagaccatgggctgggaggcctccaccgagcggatgtaccccgaggacggcgccctgaagggcgag
atcaagatgaggctgaagctgaaggacggcggccactacgacgccgaggtcaagaccacctacatggccaagaagcccg
tgcagctgcccggcgcctacaagaccgacatcaagctggacatcacctcccacaacgaggactacaccatcgtggaacag
tacgagcgcgccgagggccgccactccaccggcgccgaattc<u>tcggtcctgcttttgcgcgaggatggtgg</u>tgaaggatcct
                                                CMAH-ZPN- target sequence
<u>caatgtactaactacgctttgttgaaactcgctggcgatgttgaaagtaaccccggtcctg</u>ctagcatgaaaaagcctgaactca
    2A-peptide nucleotide sequence
ccgcgacgtctgtcgagaagtttctgatcgaaaagttcgacagcgtctccgacctgatgcagctctcggagggcgaagaatc
tcgtgctttcagcttcgatgtaggagggcgtggatatgtcctgcgggtaaatagctgcgccgatggtttctacaaagatcgttat
gtttatcggcactttgcatcggccgcgctcccgattccggaagtgcttgacattggggagttcagcgagagcctgacctattgc
atctcccgccgtgcacagggtgtcacgttgcaagacctgcctgaaaccgaactgcccgctgttctgcagccggtcgcggag
gccatggatgcgatcgctgcggccgatcttagccagacgagcgggttcggcccattcggaccgcaaggaatcggtcaatac
actacatggcgtgatttcatatgcgcgattgctgatccccatgtgtatcactggcaaactgtgatggacgacaccgtcagtgcg
tccgtcgcgcaggctctcgatgagctgatgctttgggccgaggactgccccgaagtccggcacctcgtgcacgcggatttcg
gctccaacaatgtcctgacggacaatggccgcataacagcggtcattgactggagcgaggcgatgttcggggattcccaata
cgaggtcgccaacatcttcttctggaggccgtggttggctgtatggagcagcagacgcgctacttcgagcggaggcatccg
gagcttgcaggatcgccgcggctccgggcgtatatgctccgcattggtcttgaccaactctatcagagcttggttgacggcaa
tttcgatgatgcagcttgggcgcagggtcgatgcgacgcaatcgtccgatccggagccgggactgtcgggcgtacacaaat
cgcccgcagaagcgcggccgtctggaccgatggctgtgtagaagtactcgccgatagtggaaaccgacgccccagcactc
gtccgagggcaaaggaagtcgactctagcatggtgagcaagggcgaggagctgttcaccggggtggtgcccatcctggtc
gagctggacggcgacgtaaacggccacaagttcagcgtgtccggcgagggcgagggcgatgccacctacggcaagctga
ccctgaagttcatctgcaccaccggcaagctgcccgtgccctggcccaccctcgtgaccaccctgacctacggcgtgcagt
gcttcagccgctaccccgaccacatgaagcagcacgacttcttcaagtccgccatgcccgaaggctacgtccaggagcgca
ccatcttcttcaaggacgacggcaactacaagacccgcgccgaggtgaagttcgagggcgacaccctggtgaaccgcatc
gagctgaagggcatcgacttcaaggaggacggcaacatcctggggcacaagctggagtacaactacaacagccacaacgt
ctatatcatggccgacaagcagaagaacggcatcaaggtgaacttcaagatccgccacaacatcgaggacggcagcgtgc
agctcgccgaccactaccagcagaacacccccatcggcgacggccccgtgctgctgcccgacaaccactacctgagcacc
cagtccgccctgagcaaagaccccaacgagaagcgcgatcacatggtcctgctggagttcgtgaccgccgcgggatcac
tctcggcatggacgagctgtacaagtag (SEQ ID NO: 55)

SEQUENCE LISTING

<160> NUMBER OF SEQ ID NOS: 76

<210> SEQ ID NO 1
<211> LENGTH: 1035
<212> TYPE: DNA
<213> ORGANISM: Artificial Sequence
<220> FEATURE:
<223> OTHER INFORMATION: sharkey RR FokI domain

<400> SEQUENCE: 1

```
atggtgtacc cctacgacgt gcccgactac gccgaattgc ctccaaaaaa gaagagaaag      60
gtagggatcc gaattcccgg ggaaaaaccg taccactgtg actgggacgg ctgtggatgg     120
aaattcgccc gctcagatga actgaccagg cactaccgta aacacaccgg ggaaaaaccg     180
tacaggtgta agtactgcga ccgctccttc agcgactctt cgaacctcca gcggcacgtc     240
cggaacatcc acaccgggga aaaccgtac cactgtgact gggacggctg tggatggaaa     300
ttcgcccgct cagatgaact gaccaggcac taccgtaaac acaccgggga aaaccgtac     360 aaatgcccag aatgtggaaa gagttttagc gatcctggac atcttgtgag acaccagaga     420
acacataccg gtgaaaaaca actagtcaaa agtgaactgg aggagaagaa atctgaactt     480
cgtcataaat tgaaatatgt gcctcatgaa tatattgaat taattgaaat tgccagaaat     540
cccactcagg atagaattct tgaaatgaag gtaatggaat tttttatgaa agtttatgga     600
tatagaggtg agcatttggg tggatcaagg aaaccggacg gagcaattta tactgtcgga     660
tctcctattg attacggtgt gatcgtggat actaaagctt atagcggagg ttataatctg     720
ccaattggcc aagcacgaga aatgcaacga tatgtcgaag aaaatcaaac acgaaacaaa     780
catatcaacc ctaatgaatg gtggaaagtc tatccatctt ctgtaacgga atttaagttt     840
ttatttgtga gtggtcactt taaaggaaac tacaaagctc agcttacacg attaaatcat     900
atcactaatt gtaatggagc tgttcttagt gtagaagagc ttttaattgg tggagaaatg     960
attaaagccg gcacattaac cttagaggaa gtgagacgga aatttaataa cggcgagata    1020
aactttctcg attag                                                    1035
```

<210> SEQ ID NO 2
<211> LENGTH: 344
<212> TYPE: PRT
<213> ORGANISM: Artificial Sequence
<220> FEATURE:
<223> OTHER INFORMATION: sharkey RR FokI domain

<400> SEQUENCE: 2

```
Met Val Tyr Pro Tyr Asp Val Pro Asp Tyr Ala Glu Leu Pro Pro Lys
  1               5                  10                  15

Lys Lys Arg Lys Val Gly Ile Arg Ile Pro Gly Glu Lys Pro Tyr His
             20                  25                  30

Cys Asp Trp Asp Gly Cys Gly Trp Lys Phe Ala Arg Ser Asp Glu Leu
             35                  40                  45

Thr Arg His Tyr Arg Lys His Thr Gly Glu Lys Pro Tyr Arg Cys Lys
         50                  55                  60

Tyr Cys Asp Arg Ser Phe Ser Asp Ser Ser Asn Leu Gln Arg His Val
 65              70                  75                  80

Arg Asn Ile His Thr Gly Glu Lys Pro Tyr His Cys Asp Trp Asp Gly
                 85                  90                  95

Cys Gly Trp Lys Phe Ala Arg Ser Asp Glu Leu Thr Arg His Tyr Arg
             100                 105                 110

Lys His Thr Gly Glu Lys Pro Tyr Lys Cys Pro Glu Cys Gly Lys Ser
         115                 120                 125

Phe Ser Asp Pro Gly His Leu Val Arg His Gln Arg Thr His Thr Gly
130                 135                 140

Glu Lys Gln Leu Val Lys Ser Glu Leu Glu Glu Lys Lys Ser Glu Leu
145                 150                 155                 160

Arg His Lys Leu Lys Tyr Val Pro His Glu Tyr Ile Glu Leu Ile Glu
                 165                 170                 175

Ile Ala Arg Asn Pro Thr Gln Asp Arg Ile Leu Glu Met Lys Val Met
             180                 185                 190

Glu Phe Phe Met Lys Val Tyr Gly Tyr Arg Gly Glu His Leu Gly Gly
             195                 200                 205

Ser Arg Lys Pro Asp Gly Ala Ile Tyr Thr Val Gly Ser Pro Ile Asp
         210                 215                 220

Tyr Gly Val Ile Val Asp Thr Lys Ala Tyr Ser Gly Gly Tyr Asn Leu
225                 230                 235                 240

Pro Ile Gly Gln Ala Arg Glu Met Gln Arg Tyr Val Glu Glu Asn Gln
                 245                 250                 255

Thr Arg Asn Lys His Ile Asn Pro Asn Glu Trp Trp Lys Val Tyr Pro
             260                 265                 270

Ser Ser Val Thr Glu Phe Lys Phe Leu Phe Val Ser Gly His Phe Lys
         275                 280                 285

Gly Asn Tyr Lys Ala Gln Leu Thr Arg Leu Asn His Ile Thr Asn Cys
290                 295                 300

Asn Gly Ala Val Leu Ser Val Glu Glu Leu Leu Ile Gly Gly Glu Met
305                 310                 315                 320

Ile Lys Ala Gly Thr Leu Thr Leu Glu Glu Val Arg Arg Lys Phe Asn
                 325                 330                 335

Asn Gly Glu Ile Asn Phe Leu Asp
             340
```

<210> SEQ ID NO 3
<211> LENGTH: 1020
<212> TYPE: DNA
<213> ORGANISM: Artificial Sequence
<220> FEATURE:
<223> OTHER INFORMATION: sharkey DAS FokI domain

<400> SEQUENCE: 3
atggtgtacc cctacgacgt gcccgactac gccgaattgc ctccaaaaaa gaagagaaag    60

```
gtagggatcc gaattcccgg ggaaaaaccg tataagtgcc ctgattgtgg gaagagtttt      120
agtcagagtt ccagcctcat tcgccaccag cggacacaca ccggggaaaa accgtacaaa      180
tgtgacgaat gtggaaaaaa ctttacccag tcctccaacc ttattgtaca aagagaatt       240 cataccgggg aaaaaccgta caagtgcccc gagtgcggca agagcttcag ccagaacagc      300
accctgaccg agcaccagcg gacccacacc ggggaaaaac cgtatgaatg cgatcactgt      360
gggaaagcct tcagcgtcag ctccaacctg aacgtgcaca aagaatcca caccggtgaa       420 aaacaactag tcaaaagtga actggaggag aagaaatctg aacttcgtca taaattgaaa      480
tatgtgcctc atgaatatat tgaattaatt gaaattgcca gaaatcccac tcaggataga     540
attcttgaaa tgaaggtaat ggattttttt atgaaagttt atggatatag aggtgagcat     600
ttgggtggat caaggaaacc ggacggagca atttatactg tcggatctcc tattgattac     660
ggtgtgatcg tggatactaa agcttatagc ggaggttata atctgccaat tggccaagca     720
gatgccatgc aaagctatgt cgaagaaaat caaacacgaa acaaacatat caaccctaat     780
gaatggtgga aagtctatcc atcttctgta acggaattta gttttttatt tgtgagtggt     840
cactttaaag gaaactacaa agctcagctt acacgattaa atcatatcac taattgtaat     900
ggagctgttc ttagtgtaga agagcttta  attggtggaa aaatgattaa agccggcaca      960
ttaaccttag aggaagtgag acggaaattt aataacggcg agataaactt tctcgattag     1020
```

<210> SEQ ID NO 4
<211> LENGTH: 339
<212> TYPE: PRT
<213> ORGANISM: Artificial Sequence
<220> FEATURE:
<223> OTHER INFORMATION: sharkey DAS FokI domain

<400> SEQUENCE: 4

Met Val Tyr Pro Tyr Asp Val Pro Asp Tyr Ala Glu Leu Pro Pro Lys
1               5                   10                  15

Lys Lys Arg Lys Val Gly Ile Arg Ile Pro Gly Glu Lys Pro Tyr Lys
            20                  25                  30

Cys Pro Asp Cys Gly Lys Ser Phe Ser Gln Ser Ser Ser Leu Ile Arg
        35                  40                  45

His Gln Arg Thr His Thr Gly Glu Lys Pro Tyr Lys Cys Asp Glu Cys
    50                  55                  60

Gly Lys Asn Phe Thr Gln Ser Ser Asn Leu Ile Val His Lys Arg Ile
65                  70                  75                  80

His Thr Gly Glu Lys Pro Tyr Lys Cys Pro Glu Cys Gly Lys Ser Phe
                85                  90                  95

Ser Gln Asn Ser Thr Leu Thr Glu His Gln Arg Thr His Thr Gly Glu
            100                 105                 110

Lys Pro Tyr Glu Cys Asp His Cys Gly Lys Ala Phe Ser Val Ser Ser
        115                 120                 125

Asn Leu Asn Val His Arg Arg Ile His Thr Gly Glu Lys Gln Leu Val
    130                 135                 140

Lys Ser Glu Leu Glu Glu Lys Lys Ser Glu Leu Arg His Lys Leu Lys
145                 150                 155                 160

Tyr Val Pro His Glu Tyr Ile Glu Leu Ile Glu Ile Ala Arg Asn Pro
                165                 170                 175

Thr Gln Asp Arg Ile Leu Glu Met Lys Val Met Glu Phe Phe Met Lys
            180                 185                 190

Val Tyr Gly Tyr Arg Gly Glu His Leu Gly Gly Ser Arg Lys Pro Asp

```
                    195                 200                 205
Gly Ala Ile Tyr Thr Val Gly Ser Pro Ile Asp Tyr Gly Val Ile Val
            210                 215                 220

Asp Thr Lys Ala Tyr Ser Gly Gly Tyr Asn Leu Pro Ile Gly Gln Ala
225                 230                 235                 240

Asp Ala Met Gln Ser Tyr Val Glu Glu Asn Gln Thr Arg Asn Lys His
                245                 250                 255

Ile Asn Pro Asn Glu Trp Trp Lys Val Tyr Pro Ser Ser Val Thr Glu
            260                 265                 270

Phe Lys Phe Leu Phe Val Ser Gly His Phe Lys Gly Asn Tyr Lys Ala
            275                 280                 285

Gln Leu Thr Arg Leu Asn His Ile Thr Asn Cys Asn Gly Ala Val Leu
            290                 295                 300

Ser Val Glu Glu Leu Leu Ile Gly Gly Glu Met Ile Lys Ala Gly Thr
305                 310                 315                 320

Leu Thr Leu Glu Glu Val Arg Arg Lys Phe Asn Asn Gly Glu Ile Asn
                325                 330                 335

Phe Leu Asp

<210> SEQ ID NO 5
<211> LENGTH: 37
<212> TYPE: DNA
<213> ORGANISM: Artificial Sequence
<220> FEATURE:
<223> OTHER INFORMATION: mRFP F-primer

<400> SEQUENCE: 5
gcggctagcc accatggcct cctccgagga cgtcatc                           37

<210> SEQ ID NO 6
<211> LENGTH: 37
<212> TYPE: DNA
<213> ORGANISM: Artificial Sequence
<220> FEATURE:
<223> OTHER INFORMATION: mRFP R-primer

<400> SEQUENCE: 6
gcggctagcg aattcggcgc cggtggagtg gcggccc                           37

<210> SEQ ID NO 7
<211> LENGTH: 31
<212> TYPE: DNA
<213> ORGANISM: Artificial Sequence
<220> FEATURE:
<223> OTHER INFORMATION: eGFP F-primer

<400> SEQUENCE: 7
gcgggatcca gtgagcaagg gcgaggagct g                                 31

<210> SEQ ID NO 8
<211> LENGTH: 22
<212> TYPE: DNA
<213> ORGANISM: Artificial Sequence
<220> FEATURE:
<223> OTHER INFORMATION: eGFP R-primer

<400> SEQUENCE: 8
gtcgcggccg ctttacttgt ac                                           22

<210> SEQ ID NO 9
<211> LENGTH: 34
```

-continued

<212> TYPE: DNA
<213> ORGANISM: Artificial Sequence
<220> FEATURE:
<223> OTHER INFORMATION: 2A-peptide F-primer

<400> SEQUENCE: 9
ggcggatcct caatgtacta actacgcttt gttg                                34

<210> SEQ ID NO 10
<211> LENGTH: 35
<212> TYPE: DNA
<213> ORGANISM: Artificial Sequence
<220> FEATURE:
<223> OTHER INFORMATION: 2A-peptide R-primer

<400> SEQUENCE: 10
gggcgcggcc gcctacttgt acagctcgtc catgc                               35

<210> SEQ ID NO 11
<211> LENGTH: 46
<212> TYPE: DNA
<213> ORGANISM: Artificial Sequence
<220> FEATURE:
<223> OTHER INFORMATION: 2Kk F-primer

<400> SEQUENCE: 11
ggcgctagca tggcaccctg catgctgctc ctgctgttgg ccgcgg                   46

<210> SEQ ID NO 12
<211> LENGTH: 35
<212> TYPE: DNA
<213> ORGANISM: Artificial Sequence
<220> FEATURE:
<223> OTHER INFORMATION: H-2Kk R-primer

<400> SEQUENCE: 12
gccgcggccg cttaccctcc ttttccacct gtgtt                               35

<210> SEQ ID NO 13
<211> LENGTH: 12
<212> TYPE: DNA
<213> ORGANISM: Artificial Sequence
<220> FEATURE:
<223> OTHER INFORMATION: target sequence for ZFN-224_L

<400> SEQUENCE: 13
gatgaggatg ac                                                        12

<210> SEQ ID NO 14
<211> LENGTH: 12
<212> TYPE: DNA
<213> ORGANISM: Artificial Sequence
<220> FEATURE:
<223> OTHER INFORMATION: target sequence for ZFN-224_R

<400> SEQUENCE: 14
aaactgcaaa ag                                                        12

<210> SEQ ID NO 15
<211> LENGTH: 12
<212> TYPE: DNA
<213> ORGANISM: Artificial Sequence
<220> FEATURE:
<223> OTHER INFORMATION: target sequence for Z891_L

<400> SEQUENCE: 15

-continued atagatgatg gg　　　　　　　　　　　　　　　　　　　　　　　12

<210> SEQ ID NO 16
<211> LENGTH: 12
<212> TYPE: DNA
<213> ORGANISM: Artificial Sequence
<220> FEATURE:
<223> OTHER INFORMATION: target sequence for Z891_R

<400> SEQUENCE: 16
gtcggggaga ag　　　　　　　　　　　　　　　　　　　　　　　12

<210> SEQ ID NO 17
<211> LENGTH: 12
<212> TYPE: DNA
<213> ORGANISM: Artificial Sequence
<220> FEATURE:
<223> OTHER INFORMATION: target sequence for TP53_L

<400> SEQUENCE: 17
ggcgcggacg cg　　　　　　　　　　　　　　　　　　　　　　　12

<210> SEQ ID NO 18
<211> LENGTH: 12
<212> TYPE: DNA
<213> ORGANISM: Artificial Sequence
<220> FEATURE:
<223> OTHER INFORMATION: target sequence for TP53_R

<400> SEQUENCE: 18
catctacaag ca　　　　　　　　　　　　　　　　　　　　　　　12

<210> SEQ ID NO 19
<211> LENGTH: 18
<212> TYPE: DNA
<213> ORGANISM: Artificial Sequence
<220> FEATURE:
<223> OTHER INFORMATION: target sequence for TALEN_L

<400> SEQUENCE: 19
tgcatcaacc ccatcatc　　　　　　　　　　　　　　　　　　　　18

<210> SEQ ID NO 20
<211> LENGTH: 20
<212> TYPE: DNA
<213> ORGANISM: Artificial Sequence
<220> FEATURE:
<223> OTHER INFORMATION: target sequence for TALEN_R

<400> SEQUENCE: 20
tagtttctga acttctcccc　　　　　　　　　　　　　　　　　　　20

<210> SEQ ID NO 21
<211> LENGTH: 12
<212> TYPE: DNA
<213> ORGANISM: Artificial Sequence
<220> FEATURE:
<223> OTHER INFORMATION: target sequence for Thumpd3_L

<400> SEQUENCE: 21
cgagcacgcc gc　　　　　　　　　　　　　　　　　　　　　　　12

<210> SEQ ID NO 22
<211> LENGTH: 12
<212> TYPE: DNA
<213> ORGANISM: Artificial Sequence

```
<220> FEATURE:
<223> OTHER INFORMATION: target sequence for Thumpd3_R

<400> SEQUENCE: 22
ggagaccgga ag                                                           12

<210> SEQ ID NO 23
<211> LENGTH: 12
<212> TYPE: DNA
<213> ORGANISM: Artificial Sequence
<220> FEATURE:
<223> OTHER INFORMATION: target sequence for CMAH-ZFN_L

<400> SEQUENCE: 23
aagcaggacc ga                                                           12

<210> SEQ ID NO 24
<211> LENGTH: 12
<212> TYPE: DNA
<213> ORGANISM: Artificial Sequence
<220> FEATURE:
<223> OTHER INFORMATION: target sequence for CMAH-ZFN_R

<400> SEQUENCE: 24
cgaggatggt gg                                                           12

<210> SEQ ID NO 25
<211> LENGTH: 20
<212> TYPE: DNA
<213> ORGANISM: Artificial Sequence
<220> FEATURE:
<223> OTHER INFORMATION: targer sequence for NFKB2a-L

<400> SEQUENCE: 25 tcggggtgg ctcccacatg                                                    20

<210> SEQ ID NO 26
<211> LENGTH: 20
<212> TYPE: DNA
<213> ORGANISM: Artificial Sequence
<220> FEATURE:
<223> OTHER INFORMATION: target sequence for NFKB2a-R

<400> SEQUENCE: 26 tagccccgg ctgcaccccc                                                    20

<210> SEQ ID NO 27
<211> LENGTH: 20
<212> TYPE: DNA
<213> ORGANISM: Artificial Sequence
<220> FEATURE:
<223> OTHER INFORMATION: target sequence for NFKB2b-L

<400> SEQUENCE: 27
tcgactacgg cgtcaccgcg                                                   20

<210> SEQ ID NO 28
<211> LENGTH: 20
<212> TYPE: DNA
<213> ORGANISM: Artificial Sequence
<220> FEATURE:
<223> OTHER INFORMATION: target sequence for NFKB2b-R

<400> SEQUENCE: 28
tggcgctgtc ccgccagcag                                                   20
```

<210> SEQ ID NO 29
<211> LENGTH: 1442
<212> TYPE: DNA
<213> ORGANISM: Artificial Sequence
<220> FEATURE:
<223> OTHER INFORMATION: TP53 reporter

<400> SEQUENCE: 29

| | | | | | |
|---|---|---|---|---|---|
| atggcctcct | ccgaggacgt | catcaaggag | ttcatgcgct | tcaaggtgcg | catggagggc | 60 |
| tccgtgaacg | gccacgagtt | cgagatcgag | ggcgagggcg | agggccgccc | ctacgagggc | 120 |
| acccagaccg | ccaagctgaa | ggtgaccaag | ggcggccccc | tgcccttcgc | ctgggacatc | 180 |
| ctgtcccctc | agttccagta | cggctccaag | gcctacgtga | agcaccccgc | cgacatcccc | 240 |
| gactacttga | agctgtcctt | ccccgagggc | ttcaagtggg | agcgcgtgat | gaacttcgag | 300 |
| gacggcggcg | tggtgaccgt | gacccaggac | tcctccctgc | aggacggcga | gttcatctac | 360 |
| aaggtgaagc | tgcgcggcac | caacttcccc | tccgacggcc | ccgtaatgca | gaagaagacc | 420 |
| atgggctggg | aggcctccac | cgagcggatg | taccccgagg | acggcgccct | gaagggcgag | 480 |
| atcaagatga | ggctgaagct | gaaggacggc | ggccactacg | acgccgaggt | caagaccacc | 540 |
| tacatggcca | gaaagcccgt | gcagctgccc | ggcgcctaca | agaccgacat | caagctggac | 600 |
| atcacctccc | acaacgagga | ctacaccatc | gtggaacagt | acgagcgcgc | cgagggccgc | 660 |
| cactccaccg | gcgccgaatt | cgcgtccgcg | ccatggccat | ctacaagcag | tcacagcagg | 720 |
| atccagtgag | caagggcgag | gagctgttca | ccggggtggt | gcccatcctg | gtcgagctgg | 780 |
| acggcgacgt | aaacggccac | aagttcagcg | tgtccggcga | gggcgagggc | gatgccacct | 840 |
| acggcaagct | gaccctgaag | ttcatctgca | ccaccggcaa | gctgcccgtg | ccctggccca | 900 |
| ccctcgtgac | caccctgacc | tacggcgtgc | agtgcttcag | ccgctacccc | gaccacatga | 960 |
| agcagcacga | cttcttcaag | tccgccatgc | ccgaaggcta | cgtccaggag | cgcaccatct | 1020 |
| tcttcaagga | cgacggcaac | tacaagaccc | gcgccgaggt | gaagttcgag | ggcgacaccc | 1080 |
| tggtgaaccg | catcgagctg | aagggcatcg | acttcaagga | ggacggcaac | atcctggggc | 1140 |
| acaagctgga | gtacaactac | aacagccaca | acgtctatat | catggccgac | aagcagaaga | 1200 |
| acggcatcaa | ggtgaacttc | aagatccgcc | acaacatcga | ggacggcagc | gtgcagctcg | 1260 |
| ccgaccacta | ccagcagaac | acccccatcg | gcgacggccc | cgtgctgctg | cccgacaacc | 1320 |
| actacctgag | cacccagtcc | gccctgagca | aagacccaa | cgagaagcgc | gatcacatgg | 1380 |
| tcctgctgga | gttcgtgacc | gccgccggga | tcactctcgg | catggacgag | ctgtacaagt | 1440 |
| aa | | | | | | 1442 |

<210> SEQ ID NO 30
<211> LENGTH: 21
<212> TYPE: DNA
<213> ORGANISM: Artificial Sequence
<220> FEATURE:
<223> OTHER INFORMATION: CCR5 F-primer

<400> SEQUENCE: 30
gagccaagct ctccatctag t         21

<210> SEQ ID NO 31
<211> LENGTH: 22
<212> TYPE: DNA
<213> ORGANISM: Artificial Sequence
<220> FEATURE:
<223> OTHER INFORMATION: CCR5 R-primer

```
<400> SEQUENCE: 31
ctgtatggaa aatgagagct gc                                        22

<210> SEQ ID NO 32
<211> LENGTH: 21
<212> TYPE: DNA
<213> ORGANISM: Artificial Sequence
<220> FEATURE:
<223> OTHER INFORMATION: CCR5 F-primer

<400> SEQUENCE: 32
gagccaagct ctccatctag t                                         21

<210> SEQ ID NO 33
<211> LENGTH: 22
<212> TYPE: DNA
<213> ORGANISM: Artificial Sequence
<220> FEATURE:
<223> OTHER INFORMATION: CCR5 NF-primer

<400> SEQUENCE: 33
ttaaagatag tcatcttggg gc                                        22

<210> SEQ ID NO 34
<211> LENGTH: 20
<212> TYPE: DNA
<213> ORGANISM: Artificial Sequence
<220> FEATURE:
<223> OTHER INFORMATION: CCR5 R-primer

<400> SEQUENCE: 34
tcacaagccc acagatattt                                           20

<210> SEQ ID NO 35
<211> LENGTH: 25
<212> TYPE: DNA
<213> ORGANISM: Artificial Sequence
<220> FEATURE:
<223> OTHER INFORMATION: TP53 F-primer

<400> SEQUENCE: 35
gcaggaggtg cttacgcatg tttgt                                     25

<210> SEQ ID NO 36
<211> LENGTH: 24
<212> TYPE: DNA
<213> ORGANISM: Artificial Sequence
<220> FEATURE:
<223> OTHER INFORMATION: TP53 R-primer

<400> SEQUENCE: 36
gctgctcacc atcgctatct gagc                                      24

<210> SEQ ID NO 37
<211> LENGTH: 21
<212> TYPE: DNA
<213> ORGANISM: Artificial Sequence
<220> FEATURE:
<223> OTHER INFORMATION: CCR5 F-primer

<400> SEQUENCE: 37
gagccaagct ctccatctag t                                         21

<210> SEQ ID NO 38
```

```
<211> LENGTH: 22
<212> TYPE: DNA
<213> ORGANISM: Artificial Sequence
<220> FEATURE:
<223> OTHER INFORMATION: CCR5 NF-primer

<400> SEQUENCE: 38
ttaaagatag tcatcttggg gc                                          22

<210> SEQ ID NO 39
<211> LENGTH: 20
<212> TYPE: DNA
<213> ORGANISM: Artificial Sequence
<220> FEATURE:
<223> OTHER INFORMATION: CCR5 R-primer

<400> SEQUENCE: 39
tcacaagccc acagatattt                                             20

<210> SEQ ID NO 40
<211> LENGTH: 23
<212> TYPE: DNA
<213> ORGANISM: Artificial Sequence
<220> FEATURE:
<223> OTHER INFORMATION: Thumpd3 F-primer

<400> SEQUENCE: 40
caaccgagca tccgctcgct agg                                         23

<210> SEQ ID NO 41
<211> LENGTH: 24
<212> TYPE: DNA
<213> ORGANISM: Artificial Sequence
<220> FEATURE:
<223> OTHER INFORMATION: Thumpd3 R-primer

<400> SEQUENCE: 41 gaagggctg gagtggtgtt accg                                         24

<210> SEQ ID NO 42
<211> LENGTH: 22
<212> TYPE: DNA
<213> ORGANISM: Artificial Sequence
<220> FEATURE:
<223> OTHER INFORMATION: CCR5 F-primer

<400> SEQUENCE: 42
tgcacagggt ggaacaagat gg                                          22

<210> SEQ ID NO 43
<211> LENGTH: 26
<212> TYPE: DNA
<213> ORGANISM: Artificial Sequence
<220> FEATURE:
<223> OTHER INFORMATION: CCR5 R-primer

<400> SEQUENCE: 43
gagcccagaa ggggacagta agaagg                                      26

<210> SEQ ID NO 44
<211> LENGTH: 25
<212> TYPE: DNA
<213> ORGANISM: Artificial Sequence
<220> FEATURE:
<223> OTHER INFORMATION: CCR5 F-primer

<400> SEQUENCE: 44
```

```
gaataattgc agtagctcta acagg                                              25
```

<210> SEQ ID NO 45
<211> LENGTH: 23
<212> TYPE: DNA
<213> ORGANISM: Artificial Sequence
<220> FEATURE:
<223> OTHER INFORMATION: CCR5 R-primer

<400> SEQUENCE: 45

```
ctcttgctgg aaaatagaac agc                                                23
```

<210> SEQ ID NO 46
<211> LENGTH: 25
<212> TYPE: DNA
<213> ORGANISM: Artificial Sequence
<220> FEATURE:
<223> OTHER INFORMATION: TP53 F-primer

<400> SEQUENCE: 46

```
gcaggaggtg cttacgcatg tttgt                                              25
```

<210> SEQ ID NO 47
<211> LENGTH: 24
<212> TYPE: DNA
<213> ORGANISM: Artificial Sequence
<220> FEATURE:
<223> OTHER INFORMATION: TP53 R-primer

<400> SEQUENCE: 47

```
gctgctcacc atcgctatct gagc                                               24
```

<210> SEQ ID NO 48
<211> LENGTH: 1006
<212> TYPE: PRT
<213> ORGANISM: Artificial Sequence
<220> FEATURE:
<223> OTHER INFORMATION: TALEN A-L amino acid sequence

<400> SEQUENCE: 48

Met Val Tyr Pro Tyr Asp Val Pro Asp Tyr Ala Glu Leu Pro Pro Lys
1               5                   10                  15

Lys Lys Arg Lys Val Gly Ile Arg Ile Gln Asp Leu Arg Thr Leu Gly
            20                  25                  30

Tyr Ser Gln Gln Gln Gln Glu Lys Ile Lys Pro Lys Val Arg Ser Thr
        35                  40                  45

Val Ala Gln His His Glu Ala Leu Val Gly His Gly Phe Thr His Ala
    50                  55                  60

His Ile Val Ala Leu Ser Gln His Pro Ala Ala Leu Gly Thr Val Ala
65                  70                  75                  80

Val Lys Tyr Gln Asp Met Ile Ala Ala Leu Pro Glu Ala Thr His Glu
                85                  90                  95

Ala Ile Val Gly Val Gly Lys Gln Trp Ser Gly Ala Arg Ala Leu Glu
            100                 105                 110

Ala Leu Leu Thr Val Ala Gly Glu Leu Arg Gly Pro Pro Leu Gln Leu
        115                 120                 125

Asp Thr Gly Gln Leu Leu Lys Ile Ala Lys Arg Gly Gly Val Thr Ala
    130                 135                 140

Val Glu Ala Val His Ala Trp Arg Asn Ala Leu Thr Gly Ala Pro Leu
145                 150                 155                 160

```
Asn Leu Thr Pro Glu Gln Val Val Ala Ile Ala Ser His Asp Gly Gly
            165                 170                 175

Lys Gln Ala Leu Glu Thr Val Gln Arg Leu Leu Pro Val Leu Cys Gln
        180                 185                 190

Ala His Gly Leu Thr Pro Ala Gln Val Val Ala Ile Ala Ser Asn Asn
    195                 200                 205

Gly Gly Lys Gln Ala Leu Glu Thr Val Gln Arg Leu Leu Pro Val Leu
210                 215                 220

Cys Gln Asp His Gly Leu Thr Pro Asp Gln Val Val Ala Ile Ala Ser
225                 230                 235                 240

Asn Asn Gly Gly Lys Gln Ala Leu Glu Thr Val Gln Arg Leu Leu Pro
                245                 250                 255

Val Leu Cys Gln Asp His Gly Leu Thr Pro Ala Gln Val Val Ala Ile
            260                 265                 270

Ala Ser Asn Asn Gly Gly Lys Gln Ala Leu Glu Thr Val Gln Arg Leu
        275                 280                 285

Leu Pro Val Leu Cys Gln Ala His Gly Leu Thr Pro Asp Gln Val Val
    290                 295                 300

Ala Ile Ala Ser Asn Asn Gly Gly Lys Gln Ala Leu Glu Thr Val Gln
305                 310                 315                 320

Arg Leu Leu Pro Val Leu Cys Gln Asp His Gly Leu Thr Pro Glu Gln
                325                 330                 335

Val Val Ala Ile Ala Ser Asn Asn Gly Gly Lys Gln Ala Leu Glu Thr
            340                 345                 350

Val Gln Arg Leu Leu Pro Val Leu Cys Gln Ala His Gly Leu Thr Pro
        355                 360                 365

Glu Gln Val Val Ala Ile Ala Ser Asn Gly Gly Gly Lys Gln Ala Leu
    370                 375                 380

Glu Thr Val Gln Arg Leu Leu Pro Val Leu Cys Gln Ala His Gly Leu
385                 390                 395                 400

Thr Pro Ala Gln Val Val Ala Ile Ala Ser Asn Asn Gly Gly Lys Gln
                405                 410                 415

Ala Leu Glu Thr Val Gln Arg Leu Leu Pro Val Leu Cys Gln Asp His
            420                 425                 430

Gly Leu Thr Pro Asp Gln Val Val Ala Ile Ala Ser Asn Asn Gly Gly
        435                 440                 445

Lys Gln Ala Leu Glu Thr Val Gln Arg Leu Leu Pro Val Leu Cys Gln
    450                 455                 460

Asp His Gly Leu Thr Pro Ala Gln Val Val Ala Ile Ala Ser His Asp
465                 470                 475                 480

Gly Gly Lys Gln Ala Leu Glu Thr Val Gln Arg Leu Leu Pro Val Leu
                485                 490                 495

Cys Gln Asp His Gly Leu Thr Pro Ala Gln Val Val Ala Ile Ala Ser
            500                 505                 510

Asn Gly Gly Gly Lys Gln Ala Leu Glu Thr Val Gln Arg Leu Leu Pro
        515                 520                 525

Val Leu Cys Gln Asp His Gly Leu Thr Pro Ala Gln Val Val Ala Ile
    530                 535                 540

Ala Ser His Asp Gly Gly Lys Gln Ala Leu Glu Thr Val Gln Arg Leu
545                 550                 555                 560

Leu Pro Val Leu Cys Gln Ala His Gly Leu Thr Pro Ala Gln Val Val
                565                 570                 575

Ala Ile Ala Ser His Asp Gly Gly Lys Gln Ala Leu Glu Thr Val Gln
```

-continued

```
                580                 585                 590
Arg Leu Leu Pro Val Leu Cys Gln Asp His Gly Leu Thr Pro Asp Gln
            595                 600                 605
Val Val Ala Ile Ala Ser His Asp Gly Gly Lys Gln Ala Leu Glu Thr
            610                 615                 620
Val Gln Arg Leu Leu Pro Val Leu Cys Gln Ala His Gly Leu Thr Pro
625                 630                 635                 640
Asp Gln Val Val Ala Ile Ala Ser Asn Ile Gly Gly Lys Gln Ala Leu
                645                 650                 655
Glu Thr Val Gln Arg Leu Leu Pro Val Leu Cys Gln Ala His Gly Leu
            660                 665                 670
Thr Pro Ala Gln Val Val Ala Ile Ala Ser His Asp Gly Gly Lys Gln
            675                 680                 685
Ala Leu Glu Thr Val Gln Arg Leu Leu Pro Val Leu Cys Gln Asp His
            690                 695                 700
Gly Leu Thr Pro Asp Gln Val Val Ala Ile Ala Ser Asn Ile Gly Gly
705                 710                 715                 720
Lys Gln Ala Leu Glu Thr Val Gln Arg Leu Leu Pro Val Leu Cys Gln
                725                 730                 735
Asp His Gly Leu Thr Pro Ala Gln Val Val Ala Ile Ala Ser Asn Gly
            740                 745                 750
Gly Gly Lys Gln Ala Leu Glu Thr Val Gln Arg Leu Leu Pro Val Leu
            755                 760                 765
Cys Gln Ala His Gly Leu Thr Pro Glu Gln Val Val Ala Ile Ala Ser
            770                 775                 780
Asn Asn Gly Gly Lys Gln Ala Leu Glu Ser Ile Val Ala Gln Leu Ser
785                 790                 795                 800
Arg Pro Asp Pro Ala Leu Ala Ala Leu Leu Val Lys Ser Glu Leu Glu
                805                 810                 815
Glu Lys Lys Ser Glu Leu Arg His Lys Leu Lys Tyr Val Pro His Glu
            820                 825                 830
Tyr Ile Glu Leu Ile Glu Ile Ala Arg Asn Ser Thr Gln Asp Arg Ile
            835                 840                 845
Leu Glu Met Lys Val Met Glu Phe Phe Met Lys Val Tyr Gly Tyr Arg
            850                 855                 860
Gly Lys His Leu Gly Gly Ser Arg Lys Pro Asp Gly Ala Ile Tyr Thr
865                 870                 875                 880
Val Gly Ser Pro Ile Asp Tyr Gly Val Ile Val Asp Thr Lys Ala Tyr
                885                 890                 895
Ser Gly Gly Tyr Asn Leu Pro Ile Gly Gln Ala Asp Glu Met Gln Arg
                900                 905                 910
Tyr Val Glu Glu Asn Gln Thr Arg Asn Lys His Ile Asn Pro Asn Glu
            915                 920                 925
Trp Trp Lys Val Tyr Pro Ser Ser Val Thr Glu Phe Lys Phe Leu Phe
            930                 935                 940
Val Ser Gly His Phe Lys Gly Asn Tyr Lys Ala Gln Leu Thr Arg Leu
945                 950                 955                 960
Asn His Ile Thr Asn Cys Asn Gly Ala Val Leu Ser Val Glu Glu Leu
                965                 970                 975
Leu Ile Gly Gly Glu Met Ile Lys Ala Gly Thr Leu Thr Leu Glu Glu
            980                 985                 990
Val Arg Arg Lys Phe Asn Asn Gly  Glu Ile Asn Phe  Leu  Asp
            995                1000                1005
```

<210> SEQ ID NO 49
<211> LENGTH: 1006
<212> TYPE: PRT
<213> ORGANISM: Artificial Sequence
<220> FEATURE:
<223> OTHER INFORMATION: TALEN A-R amino acid sequence

<400> SEQUENCE: 49

```
Met Val Tyr Pro Tyr Asp Val Pro Asp Tyr Ala Glu Leu Pro Pro Lys
1               5                   10                  15

Lys Lys Arg Lys Val Gly Ile Arg Ile Gln Asp Leu Arg Thr Leu Gly
            20                  25                  30

Tyr Ser Gln Gln Gln Gln Glu Lys Ile Lys Pro Lys Val Arg Ser Thr
        35                  40                  45

Val Ala Gln His His Glu Ala Leu Val Gly His Gly Phe Thr His Ala
    50                  55                  60

His Ile Val Ala Leu Ser Gln His Pro Ala Ala Leu Gly Thr Val Ala
65                  70                  75                  80

Val Lys Tyr Gln Asp Met Ile Ala Ala Leu Pro Glu Ala Thr His Glu
                85                  90                  95

Ala Ile Val Gly Val Gly Lys Gln Trp Ser Gly Ala Arg Ala Leu Glu
            100                 105                 110

Ala Leu Leu Thr Val Ala Gly Glu Leu Arg Gly Pro Pro Leu Gln Leu
        115                 120                 125

Asp Thr Gly Gln Leu Leu Lys Ile Ala Lys Arg Gly Gly Val Thr Ala
    130                 135                 140

Val Glu Ala Val His Ala Trp Arg Asn Ala Leu Thr Gly Ala Pro Leu
145                 150                 155                 160

Asn Leu Thr Pro Ala Gln Val Val Ala Ile Ala Ser Asn Ile Gly Gly
                165                 170                 175

Lys Gln Ala Leu Glu Thr Val Gln Arg Leu Leu Pro Val Leu Cys Gln
            180                 185                 190

Asp His Gly Leu Thr Pro Asp Gln Val Val Ala Ile Ala Ser Asn Asn
        195                 200                 205

Gly Gly Lys Gln Ala Leu Glu Thr Val Gln Arg Leu Leu Pro Val Leu
    210                 215                 220

Cys Gln Asp His Gly Leu Thr Pro Glu Gln Val Val Ala Ile Ala Ser
225                 230                 235                 240

His Asp Gly Gly Lys Gln Ala Leu Glu Thr Val Gln Arg Leu Leu Pro
                245                 250                 255

Val Leu Cys Gln Ala His Gly Leu Thr Pro Ala Gln Val Val Ala Ile
            260                 265                 270

Ala Ser His Asp Gly Gly Lys Gln Ala Leu Glu Thr Val Gln Arg Leu
        275                 280                 285

Leu Pro Val Leu Cys Gln Ala His Gly Leu Thr Pro Asp Gln Val Val
    290                 295                 300

Ala Ile Ala Ser His Asp Gly Gly Lys Gln Ala Leu Glu Thr Val Gln
305                 310                 315                 320

Arg Leu Leu Pro Val Leu Cys Gln Asp His Gly Leu Thr Pro Asp Gln
                325                 330                 335

Val Val Ala Ile Ala Ser His Asp Gly Gly Lys Gln Ala Leu Glu Thr
            340                 345                 350

Val Gln Arg Leu Leu Pro Val Leu Cys Gln Asp His Gly Leu Thr Pro
        355                 360                 365
```

```
Glu Gln Val Val Ala Ile Ala Ser His Asp Gly Gly Lys Gln Ala Leu
    370                 375                 380
Glu Thr Val Gln Arg Leu Leu Pro Val Leu Cys Gln Ala His Gly Leu
385                 390                 395                 400
Thr Pro Ala Gln Val Val Ala Ile Ala Ser Asn Asn Gly Gly Lys Gln
                405                 410                 415
Ala Leu Glu Thr Val Gln Arg Leu Leu Pro Val Leu Cys Gln Asp His
            420                 425                 430
Gly Leu Thr Pro Asp Gln Val Val Ala Ile Ala Ser Asn Asn Gly Gly
            435                 440                 445
Lys Gln Ala Leu Glu Thr Val Gln Arg Leu Leu Pro Val Leu Cys Gln
450                 455                 460
Asp His Gly Leu Thr Pro Ala Gln Val Val Ala Ile Ala Ser His Asp
465                 470                 475                 480
Gly Gly Lys Gln Ala Leu Glu Thr Val Gln Arg Leu Leu Pro Val Leu
                485                 490                 495
Cys Gln Ala His Gly Leu Thr Pro Ala Gln Val Val Ala Ile Ala Ser
            500                 505                 510
Asn Gly Gly Gly Lys Gln Ala Leu Glu Thr Val Gln Arg Leu Leu Pro
        515                 520                 525
Val Leu Cys Gln Asp His Gly Leu Thr Pro Asp Gln Val Val Ala Ile
        530                 535                 540
Ala Ser Asn Asn Gly Gly Lys Gln Ala Leu Glu Thr Val Gln Arg Leu
545                 550                 555                 560
Leu Pro Val Leu Cys Gln Asp His Gly Leu Thr Pro Asp Gln Val Val
                565                 570                 575
Ala Ile Ala Ser His Asp Gly Gly Lys Gln Ala Leu Glu Thr Val Gln
            580                 585                 590
Arg Leu Leu Pro Val Leu Cys Gln Ala His Gly Leu Thr Pro Asp Gln
        595                 600                 605
Val Val Ala Ile Ala Ser Asn Ile Gly Gly Lys Gln Ala Leu Glu Thr
        610                 615                 620
Val Gln Arg Leu Leu Pro Val Leu Cys Gln Ala His Gly Leu Thr Pro
625                 630                 635                 640
Ala Gln Val Val Ala Ile Ala Ser His Asp Gly Gly Lys Gln Ala Leu
                645                 650                 655
Glu Thr Val Gln Arg Leu Leu Pro Val Leu Cys Gln Ala His Gly Leu
            660                 665                 670
Thr Pro Ala Gln Val Val Ala Ile Ala Ser His Asp Gly Gly Lys Gln
        675                 680                 685
Ala Leu Glu Thr Val Gln Arg Leu Leu Pro Val Leu Cys Gln Ala His
        690                 695                 700
Gly Leu Thr Pro Asp Gln Val Val Ala Ile Ala Ser His Asp Gly Gly
705                 710                 715                 720
Lys Gln Ala Leu Glu Thr Val Gln Arg Leu Leu Pro Val Leu Cys Gln
                725                 730                 735
Asp His Gly Leu Thr Pro Asp Gln Val Val Ala Ile Ala Ser His Asp
            740                 745                 750
Gly Gly Lys Gln Ala Leu Glu Thr Val Gln Arg Leu Leu Pro Val Leu
        755                 760                 765
Cys Gln Asp His Gly Leu Thr Pro Glu Gln Val Val Ala Ile Ala Ser
        770                 775                 780
```

His Asp Gly Gly Lys Gln Ala Leu Glu Ser Ile Val Ala Gln Leu Ser
785                 790                 795                 800

Arg Pro Asp Pro Ala Leu Ala Ala Leu Leu Val Lys Ser Glu Leu Glu
            805                 810                 815

Glu Lys Lys Ser Glu Leu Arg His Lys Leu Lys Tyr Val Pro His Glu
            820                 825                 830

Tyr Ile Glu Leu Ile Glu Ile Ala Arg Asn Ser Thr Gln Asp Arg Ile
        835                 840                 845

Leu Glu Met Lys Val Met Glu Phe Phe Met Lys Val Tyr Gly Tyr Arg
    850                 855                 860

Gly Lys His Leu Gly Gly Ser Arg Lys Pro Asp Gly Ala Ile Tyr Thr
865                 870                 875                 880

Val Gly Ser Pro Ile Asp Tyr Gly Val Ile Val Asp Thr Lys Ala Tyr
            885                 890                 895

Ser Gly Gly Tyr Asn Leu Pro Ile Gly Gln Ala Asp Glu Met Gln Arg
        900                 905                 910

Tyr Val Glu Glu Asn Gln Thr Arg Asn Lys His Ile Asn Pro Asn Glu
    915                 920                 925

Trp Trp Lys Val Tyr Pro Ser Ser Val Thr Glu Phe Lys Phe Leu Phe
930                 935                 940

Val Ser Gly His Phe Lys Gly Asn Tyr Lys Ala Gln Leu Thr Arg Leu
945                 950                 955                 960

Asn His Ile Thr Asn Cys Asn Gly Ala Val Leu Ser Val Glu Glu Leu
            965                 970                 975

Leu Ile Gly Gly Glu Met Ile Lys Ala Gly Thr Leu Thr Leu Glu Glu
        980                 985                 990

Val Arg Arg Lys Phe Asn Asn Gly Glu Ile Asn Phe Leu Asp
    995                 1000                1005

<210> SEQ ID NO 50
<211> LENGTH: 1006
<212> TYPE: PRT
<213> ORGANISM: Artificial Sequence
<220> FEATURE:
<223> OTHER INFORMATION: TALEN B-L amino acid sequence

<400> SEQUENCE: 50

Met Val Tyr Pro Tyr Asp Val Pro Asp Tyr Ala Glu Leu Pro Pro Lys
1               5                   10                  15

Lys Lys Arg Lys Val Gly Ile Arg Ile Gln Asp Leu Arg Thr Leu Gly
            20                  25                  30

Tyr Ser Gln Gln Gln Gln Glu Lys Ile Lys Pro Lys Val Arg Ser Thr
        35                  40                  45

Val Ala Gln His His Glu Ala Leu Val Gly His Gly Phe Thr His Ala
    50                  55                  60

His Ile Val Ala Leu Ser Gln His Pro Ala Ala Leu Gly Thr Val Ala
65                  70                  75                  80

Val Lys Tyr Gln Asp Met Ile Ala Ala Leu Pro Glu Ala Thr His Glu
            85                  90                  95

Ala Ile Val Gly Val Gly Lys Gln Trp Ser Gly Ala Arg Ala Leu Glu
        100                 105                 110

Ala Leu Leu Thr Val Ala Gly Glu Leu Arg Gly Pro Pro Leu Gln Leu
    115                 120                 125

Asp Thr Gly Gln Leu Leu Lys Ile Ala Lys Arg Gly Gly Val Thr Ala
    130                 135                 140

-continued

```
Val Glu Ala Val His Ala Trp Arg Asn Ala Leu Thr Gly Ala Pro Leu
145                 150                 155                 160

Asn Leu Thr Pro Glu Gln Val Ala Ile Ala Ser His Asp Gly Gly
            165                 170                 175

Lys Gln Ala Leu Glu Thr Val Gln Arg Leu Leu Pro Val Leu Cys Gln
            180                 185                 190

Ala His Gly Leu Thr Pro Ala Gln Val Val Ala Ile Ala Ser Asn Asn
        195                 200                 205

Gly Gly Lys Gln Ala Leu Glu Thr Val Gln Arg Leu Leu Pro Val Leu
210                 215                 220

Cys Gln Ala His Gly Leu Thr Pro Ala Gln Val Val Ala Ile Ala Ser
225                 230                 235                 240

Asn Ile Gly Gly Lys Gln Ala Leu Glu Thr Val Gln Arg Leu Leu Pro
            245                 250                 255

Val Leu Cys Gln Asp His Gly Leu Thr Pro Asp Gln Val Val Ala Ile
            260                 265                 270

Ala Ser His Asp Gly Gly Lys Gln Ala Leu Glu Thr Val Gln Arg Leu
        275                 280                 285

Leu Pro Val Leu Cys Gln Ala His Gly Leu Thr Pro Asp Gln Val Val
290                 295                 300

Ala Ile Ala Ser Asn Gly Gly Lys Gln Ala Leu Glu Thr Val Gln
305                 310                 315                 320

Arg Leu Leu Pro Val Leu Cys Gln Asp His Gly Leu Thr Pro Ala Gln
            325                 330                 335

Val Val Ala Ile Ala Ser Asn Ile Gly Gly Lys Gln Ala Leu Glu Thr
            340                 345                 350

Val Gln Arg Leu Leu Pro Val Leu Cys Gln Asp His Gly Leu Thr Pro
        355                 360                 365

Glu Gln Val Val Ala Ile Ala Ser His Asp Gly Gly Lys Gln Ala Leu
370                 375                 380

Glu Thr Val Gln Arg Leu Leu Pro Val Leu Cys Gln Ala His Gly Leu
385                 390                 395                 400

Thr Pro Ala Gln Val Val Ala Ile Ala Ser Asn Asn Gly Gly Lys Gln
            405                 410                 415

Ala Leu Glu Thr Val Gln Arg Leu Leu Pro Val Leu Cys Gln Asp His
            420                 425                 430

Gly Leu Thr Pro Asp Gln Val Val Ala Ile Ala Ser Asn Asn Gly Gly
        435                 440                 445

Lys Gln Ala Leu Glu Thr Val Gln Arg Leu Leu Pro Val Leu Cys Gln
450                 455                 460

Asp His Gly Leu Thr Pro Asp Gln Val Val Ala Ile Ala Ser His Asp
465                 470                 475                 480

Gly Gly Lys Gln Ala Leu Glu Thr Val Gln Arg Leu Leu Pro Val Leu
            485                 490                 495

Cys Gln Asp His Gly Leu Thr Pro Asp Gln Val Val Ala Ile Ala Ser
            500                 505                 510

Asn Asn Gly Gly Lys Gln Ala Leu Glu Thr Val Gln Arg Leu Leu Pro
        515                 520                 525

Val Leu Cys Gln Asp His Gly Leu Thr Pro Ala Gln Val Val Ala Ile
530                 535                 540

Ala Ser Asn Gly Gly Gly Lys Gln Ala Leu Glu Thr Val Gln Arg Leu
545                 550                 555                 560

Leu Pro Val Leu Cys Gln Ala His Gly Leu Thr Pro Asp Gln Val Val
```

```
                    565                 570                 575
Ala Ile Ala Ser His Asp Gly Gly Lys Gln Ala Leu Glu Thr Val Gln
                580                 585                 590

Arg Leu Leu Pro Val Leu Cys Gln Ala His Gly Leu Thr Pro Asp Gln
                595                 600                 605

Val Val Ala Ile Ala Ser Asn Ile Gly Gly Lys Gln Ala Leu Glu Thr
                610                 615                 620

Val Gln Arg Leu Leu Pro Val Leu Cys Gln Ala His Gly Leu Thr Pro
625                 630                 635                 640

Ala Gln Val Val Ala Ile Ala Ser His Asp Gly Gly Lys Gln Ala Leu
                    645                 650                 655

Glu Thr Val Gln Arg Leu Leu Pro Val Leu Cys Gln Ala His Gly Leu
                660                 665                 670

Thr Pro Ala Gln Val Val Ala Ile Ala Ser His Asp Gly Gly Lys Gln
                    675                 680                 685

Ala Leu Glu Thr Val Gln Arg Leu Leu Pro Val Leu Cys Gln Ala His
                690                 695                 700

Gly Leu Thr Pro Asp Gln Val Val Ala Ile Ala Ser Asn Asn Gly Gly
705                 710                 715                 720

Lys Gln Ala Leu Glu Thr Val Gln Arg Leu Leu Pro Val Leu Cys Gln
                    725                 730                 735

Asp His Gly Leu Thr Pro Asp Gln Val Val Ala Ile Ala Ser His Asp
                740                 745                 750

Gly Gly Lys Gln Ala Leu Glu Thr Val Gln Arg Leu Leu Pro Val Leu
                    755                 760                 765

Cys Gln Asp His Gly Leu Thr Pro Glu Gln Val Val Ala Ile Ala Ser
                770                 775                 780

Asn Asn Gly Gly Lys Gln Ala Leu Glu Ser Ile Val Ala Gln Leu Ser
785                 790                 795                 800

Arg Pro Asp Pro Ala Leu Ala Ala Leu Leu Val Lys Ser Glu Leu Glu
                    805                 810                 815

Glu Lys Lys Ser Glu Leu Arg His Lys Leu Lys Tyr Val Pro His Glu
                820                 825                 830

Tyr Ile Glu Leu Ile Glu Ile Ala Arg Asn Ser Thr Gln Asp Arg Ile
                835                 840                 845

Leu Glu Met Lys Val Met Glu Phe Phe Met Lys Val Tyr Gly Tyr Arg
                850                 855                 860

Gly Lys His Leu Gly Gly Ser Arg Lys Pro Asp Gly Ala Ile Tyr Thr
865                 870                 875                 880

Val Gly Ser Pro Ile Asp Tyr Gly Val Ile Val Asp Thr Lys Ala Tyr
                    885                 890                 895

Ser Gly Gly Tyr Asn Leu Pro Ile Gly Gln Ala Asp Glu Met Gln Arg
                900                 905                 910

Tyr Val Glu Glu Asn Gln Thr Arg Asn Lys His Ile Asn Pro Asn Glu
                915                 920                 925

Trp Trp Lys Val Tyr Pro Ser Ser Val Thr Glu Phe Lys Phe Leu Phe
                930                 935                 940

Val Ser Gly His Phe Lys Gly Asn Tyr Lys Ala Gln Leu Thr Arg Leu
945                 950                 955                 960

Asn His Ile Thr Asn Cys Asn Gly Ala Val Leu Ser Val Glu Glu Leu
                    965                 970                 975

Leu Ile Gly Gly Glu Met Ile Lys Ala Gly Thr Leu Thr Leu Glu Glu
                980                 985                 990
```

Val Arg Arg Lys Phe Asn Asn Gly Glu Ile Asn Phe Leu Asp
         995                1000                1005

<210> SEQ ID NO 51
<211> LENGTH: 1006
<212> TYPE: PRT
<213> ORGANISM: Artificial Sequence
<220> FEATURE:
<223> OTHER INFORMATION: TALEN B-R amino acid sequence

<400> SEQUENCE: 51

Met Val Tyr Pro Tyr Asp Val Pro Asp Tyr Ala Glu Leu Pro Pro Lys
1               5                   10                  15

Lys Lys Arg Lys Val Gly Ile Arg Ile Gln Asp Leu Arg Thr Leu Gly
            20                  25                  30

Tyr Ser Gln Gln Gln Glu Lys Ile Lys Pro Lys Val Arg Ser Thr
        35                  40                  45

Val Ala Gln His His Glu Ala Leu Val Gly His Gly Phe Thr His Ala
    50                  55                  60

His Ile Val Ala Leu Ser Gln His Pro Ala Ala Leu Gly Thr Val Ala
65                  70                  75                  80

Val Lys Tyr Gln Asp Met Ile Ala Ala Leu Pro Glu Ala Thr His Glu
                85                  90                  95

Ala Ile Val Gly Val Gly Lys Gln Trp Ser Gly Ala Arg Ala Leu Glu
            100                 105                 110

Ala Leu Leu Thr Val Ala Gly Glu Leu Arg Gly Pro Pro Leu Gln Leu
        115                 120                 125

Asp Thr Gly Gln Leu Leu Lys Ile Ala Lys Arg Gly Gly Val Thr Ala
    130                 135                 140

Val Glu Ala Val His Ala Trp Arg Asn Ala Leu Thr Gly Ala Pro Leu
145                 150                 155                 160

Asn Leu Thr Pro Glu Gln Val Val Ala Ile Ala Ser Asn Asn Gly Gly
                165                 170                 175

Lys Gln Ala Leu Glu Thr Val Gln Arg Leu Leu Pro Val Leu Cys Gln
            180                 185                 190

Ala His Gly Leu Thr Pro Ala Gln Val Val Ala Ile Ala Ser Asn Asn
        195                 200                 205

Gly Gly Lys Gln Ala Leu Glu Thr Val Gln Arg Leu Leu Pro Val Leu
    210                 215                 220

Cys Gln Asp His Gly Leu Thr Pro Asp Gln Val Val Ala Ile Ala Ser
225                 230                 235                 240

His Asp Gly Gly Lys Gln Ala Leu Glu Thr Val Gln Arg Leu Leu Pro
                245                 250                 255

Val Leu Cys Gln Asp His Gly Leu Thr Pro Asp Gln Val Val Ala Ile
            260                 265                 270

Ala Ser Asn Asn Gly Gly Lys Gln Ala Leu Glu Thr Val Gln Arg Leu
        275                 280                 285

Leu Pro Val Leu Cys Gln Ala His Gly Leu Thr Pro Ala Gln Val Val
    290                 295                 300

Ala Ile Ala Ser His Asp Gly Gly Lys Gln Ala Leu Glu Thr Val Gln
305                 310                 315                 320

Arg Leu Leu Pro Val Leu Cys Gln Asp His Gly Leu Thr Pro Asp Gln
                325                 330                 335

Val Val Ala Ile Ala Ser Asn Gly Gly Gly Lys Gln Ala Leu Glu Thr
            340                 345                 350

```
Val Gln Arg Leu Leu Pro Val Leu Cys Gln Ala His Gly Leu Thr Pro
        355                 360                 365
Ala Gln Val Val Ala Ile Ala Ser Asn Asn Gly Gly Lys Gln Ala Leu
        370                 375                 380
Glu Thr Val Gln Arg Leu Leu Pro Val Leu Cys Gln Asp His Gly Leu
385                 390                 395                 400
Thr Pro Ala Gln Val Val Ala Ile Ala Ser Asn Gly Gly Gly Lys Gln
                405                 410                 415
Ala Leu Glu Thr Val Gln Arg Leu Leu Pro Val Leu Cys Gln Ala His
            420                 425                 430
Gly Leu Thr Pro Asp Gln Val Val Ala Ile Ala Ser His Asp Gly Gly
        435                 440                 445
Lys Gln Ala Leu Glu Thr Val Gln Arg Leu Leu Pro Val Leu Cys Gln
        450                 455                 460
Asp His Gly Leu Thr Pro Ala Gln Val Val Ala Ile Ala Ser His Asp
465                 470                 475                 480
Gly Gly Lys Gln Ala Leu Glu Thr Val Gln Arg Leu Leu Pro Val Leu
                485                 490                 495
Cys Gln Asp His Gly Leu Thr Pro Asp Gln Val Val Ala Ile Ala Ser
            500                 505                 510
His Asp Gly Gly Lys Gln Ala Leu Glu Thr Val Gln Arg Leu Leu Pro
        515                 520                 525
Val Leu Cys Gln Ala His Gly Leu Thr Pro Glu Gln Val Val Ala Ile
        530                 535                 540
Ala Ser Asn Asn Gly Gly Lys Gln Ala Leu Glu Thr Val Gln Arg Leu
545                 550                 555                 560
Leu Pro Val Leu Cys Gln Ala His Gly Leu Thr Pro Ala Gln Val Val
                565                 570                 575
Ala Ile Ala Ser His Asp Gly Gly Lys Gln Ala Leu Glu Thr Val Gln
            580                 585                 590
Arg Leu Leu Pro Val Leu Cys Gln Asp His Gly Leu Thr Pro Asp Gln
        595                 600                 605
Val Val Ala Ile Ala Ser His Asp Gly Gly Lys Gln Ala Leu Glu Thr
        610                 615                 620
Val Gln Arg Leu Leu Pro Val Leu Cys Gln Ala His Gly Leu Thr Pro
625                 630                 635                 640
Asp Gln Val Val Ala Ile Ala Ser Asn Ile Gly Gly Lys Gln Ala Leu
                645                 650                 655
Glu Thr Val Gln Arg Leu Leu Pro Val Leu Cys Gln Ala His Gly Leu
            660                 665                 670
Thr Pro Ala Gln Val Val Ala Ile Ala Ser Asn Asn Gly Gly Lys Gln
        675                 680                 685
Ala Leu Glu Thr Val Gln Arg Leu Leu Pro Val Leu Cys Gln Ala His
        690                 695                 700
Gly Leu Thr Pro Asp Gln Val Val Ala Ile Ala Ser His Asp Gly Gly
705                 710                 715                 720
Lys Gln Ala Leu Glu Thr Val Gln Arg Leu Leu Pro Val Leu Cys Gln
                725                 730                 735
Asp His Gly Leu Thr Pro Ala Gln Val Val Ala Ile Ala Ser Asn Ile
            740                 745                 750
Gly Gly Lys Gln Ala Leu Glu Thr Val Gln Arg Leu Leu Pro Val Leu
        755                 760                 765
```

```
Cys Gln Ala His Gly Leu Thr Pro Glu Gln Val Val Ala Ile Ala Ser
770                 775                 780

Asn Asn Gly Gly Lys Gln Ala Leu Glu Ser Ile Val Ala Gln Leu Ser
785                 790                 795                 800

Arg Pro Asp Pro Ala Leu Ala Ala Leu Leu Val Lys Ser Glu Leu Glu
                805                 810                 815

Glu Lys Lys Ser Glu Leu Arg His Lys Leu Lys Tyr Val Pro His Glu
                820                 825                 830

Tyr Ile Glu Leu Ile Glu Ile Ala Arg Asn Ser Thr Gln Asp Arg Ile
                835                 840                 845

Leu Glu Met Lys Val Met Glu Phe Phe Met Lys Val Tyr Gly Tyr Arg
850                 855                 860

Gly Lys His Leu Gly Gly Ser Arg Lys Pro Asp Gly Ala Ile Tyr Thr
865                 870                 875                 880

Val Gly Ser Pro Ile Asp Tyr Gly Val Ile Val Asp Thr Lys Ala Tyr
                885                 890                 895

Ser Gly Gly Tyr Asn Leu Pro Ile Gly Gln Ala Asp Glu Met Gln Arg
                900                 905                 910

Tyr Val Glu Glu Asn Gln Thr Arg Asn Lys His Ile Asn Pro Asn Glu
                915                 920                 925

Trp Trp Lys Val Tyr Pro Ser Ser Val Thr Glu Phe Lys Phe Leu Phe
930                 935                 940

Val Ser Gly His Phe Lys Gly Asn Tyr Lys Ala Gln Leu Thr Arg Leu
945                 950                 955                 960

Asn His Ile Thr Asn Cys Asn Gly Ala Val Leu Ser Val Glu Glu Leu
                965                 970                 975

Leu Ile Gly Gly Glu Met Ile Lys Ala Gly Thr Leu Thr Leu Glu Glu
                980                 985                 990

Val Arg Arg Lys Phe Asn Asn Gly  Glu Ile Asn Phe Leu  Asp
                995                 1000                1005

<210> SEQ ID NO 52
<211> LENGTH: 2185
<212> TYPE: DNA
<213> ORGANISM: Artificial Sequence
<220> FEATURE:
<223> OTHER INFORMATION: TALEN double frame reporter DNA sequence

<400> SEQUENCE: 52
atggcctcct ccgaggacgt catcaaggag ttcatgcgct tcaaggtgcg catggagggc      60
tccgtgaacg gccacgagtt cgagatcgag ggcgagggcg agggccgccc ctacgagggc     120
acccagaccg ccaagctgaa ggtgaccaag ggcggccccc tgcccttcgc ctgggacatc     180
ctgtcccctc agttccagta cggctccaag gcctacgtga agcaccccgc cgacatcccc     240
gactacttga agctgtcctt ccccgagggc ttcaagtggg agcgcgtgat gaacttcgag     300
gacggcggcg tggtgaccgt gacccaggac tcctccctgc aggacggcga gttcatctac     360
aaggtgaagc tgcgcggcac caacttcccc tccgacggcc ccgtaatgca gaagaagacc     420
atgggctggg aggcctccac cgagcggatg taccccgagg acggcgccct gaagggcgag     480
atcaagatga ggctgaagct gaaggacggc ggccactacg acgccgaggt caagaccacc     540
tacatggcca agaagcccgt gcagctgccc ggcgcctaca agaccgacat caagctggac     600
atcacctccc acaacgagga ctacaccatc gtggaacagt acgagcgcgc cgagggccgc     660
cactccaccg gcgccgaatt ctcggggggtg gctcccacat gggtggaggc tctgggggtg     720
```

```
cagccggggg ctaggatcca gtgagcaagg gcgaggagct gttcaccggg gtggtgccca      780
tcctggtcga gctggacggc gacgtaaacg gccacaagtt cagcgtgtcc ggcgagggcg      840
agggcgatgc cacctacggc aagctgaccc tgaagttcat ctgcaccacc ggcaagctgc      900
ccgtgccctg ccccaccctc gtgaccaccc tgacctacgg cgtgcagtgc ttcagccgct      960
accccgacca catgaagcag cacgacttct tcaagtccgc catgcccgaa ggctacgtcc     1020
aggagcgcac catcttcttc aaggacgacg gcaactacaa gacccgcgcc gaggtgaagt     1080
tcgagggcga caccctggtg aaccgcatcg agctgaaggg catcgacttc aaggaggacg     1140
gcaacatcct ggggcacaag ctggagtaca actacaacag ccacaacgtc tatatcatgg     1200
ccgacaagca gaagaacggc atcaaggtga acttcaagat ccgccacaac atcgaggacg     1260
gcagcgtgca gctcgccgac cactaccagc agaacacccc catcggcgac ggccccgtgc     1320
tgctgcccga caaccactac ctgagcaccc agtccgccct gagcaaagac cccaacgaga     1380
agcgcgatca catggtcctg ctggagttcg tgaccgccgc cgggatcact ctcggcatgg     1440
acgagctgta caagtaaagc ggccgccagt gagcaagggc gaggagctgt tcaccggggt     1500
ggtgcccatc ctggtcgagc tggacggcga cgtaaacggc cacaagttca gcgtgtccgg     1560
cgagggcgag ggcgatgcca cctacggcaa gctgaccctg aagttcatct gcaccaccgg     1620
caagctgccc gtgccctggc ccaccctcgt gaccaccctg acctacgcg tgcagtgctt     1680 cagccgctac cccgaccaca tgaagcagca cgacttcttc aagtccgcca tgcccgaagg     1740
ctacgtccag gagcgcacca tcttcttcaa ggacgacggc aactacaaga cccgcgccga     1800
ggtgaagttc gagggcgaca ccctggtgaa ccgcatcgag ctgaagggca tcgacttcaa     1860
ggaggacggc aacatcctgg ggcacaagct ggagtacaac tacaacagcc acaacgtcta     1920
tatcatggcc gacaagcaga agaacggcat caaggtgaac ttcaagatcc gccacaacat     1980
cgaggacggc agcgtgcagc tcgccgacca ctaccagcag aacaccccca tcggcgacgg     2040
ccccgtgctg ctgcccgaca accactacct gagcacccag tccgccctga gcaaagaccc     2100
caacgagaag cgcgatcaca tggtcctgct ggagttcgtg accgccgccg ggatcactct     2160
cggcatggac gagctgtaca agtaa                                           2185
```

<210> SEQ ID NO 53
<211> LENGTH: 2185
<212> TYPE: DNA
<213> ORGANISM: Artificial Sequence
<220> FEATURE:
<223> OTHER INFORMATION: TALEN double frame reporter DNA sequence

<400> SEQUENCE: 53

```
atggcctcct ccgaggacgt catcaaggag ttcatgcgct tcaaggtgcg catggagggc       60
tccgtgaacg gccacgagtt cgagatcgag ggcgagggcg agggccgccc ctacgagggc      120
acccagaccg ccaagctgaa ggtgaccaag ggcggccccc tgcccttcgc ctgggacatc      180 ctgtccccctc agttccagta cggctccaag gcctacgtga agcaccccgc cgacatcccc      240
gactacttga agctgtcctt ccccgagggc ttcaagtggg agcgcgtgat gaacttcgag      300
gacggcggcg tggtgaccgt gacccaggac tcctccctgc aggacggcga gttcatctac      360
aaggtgaagc tgcgcggcac caacttcccc tccgacggcc ccgtaatgca gaagaagacc      420
atgggctggg aggcctccac cgagcggatg taccccgagg acggcgccct gaagggcgag      480
atcaagatga ggctgaagct gaaggacggc ggccactacg acgccgaggt caagaccacc      540
tacatggcca agaagcccgt gcagctgccc ggcgcctaca agaccgacat caagctggac      600
```

```
atcacctccc acaacgagga ctacaccatc gtggaacagt acgagcgcgc cgagggccgc    660
cactccaccg gcgccgaatt ctcgactacg gcgtcaccgc ggacgcgcgc gcgctgctgg    720
cgggacagcg ccaggatcca gtgagcaagg gcgaggagct gttcaccggg gtggtgccca    780
tcctggtcga gctggacggc gacgtaaacg gccacaagtt cagcgtgtcc ggcgagggcg    840
agggcgatgc cacctacggc aagctgaccc tgaagttcat ctgcaccacc ggcaagctgc    900
ccgtgccctg gcccaccctc gtgaccaccc tgacctacgg cgtgcagtgc ttcagccgct    960
accccgacca catgaagcag cacgacttct tcaagtccgc catgcccgaa ggctacgtcc   1020
aggagcgcac catcttcttc aaggacgacg gcaactacaa gacccgcgcc gaggtgaagt   1080
tcgagggcga caccctggtg aaccgcatcg agctgaaggg catcgacttc aaggaggacg   1140
gcaacatcct ggggcacaag ctggagtaca actacaacag ccacaacgtc tatatcatgg   1200
ccgacaagca gaagaacggc atcaaggtga acttcaagat ccgccacaac atcgaggacg   1260
gcagcgtgca gctcgccgac cactaccagc agaacacccc catcggcgac ggccccgtgc   1320
tgctgcccga caaccactac ctgagcaccc agtccgccct gagcaaagac cccaacgaga   1380
agcgcgatca catggtcctg ctggagttcg tgaccgccgc cgggatcact ctcggcatgg   1440
acgagctgta caagtaaagc ggccgccagt gagcaagggc gaggagctgt tcaccggggt   1500
ggtgcccatc ctggtcgagc tggacggcga cgtaaacggc cacaagttca gcgtgtccgg   1560
cgagggcgag ggcgatgcca cctacggcaa gctgaccctg aagttcatct gcaccaccgg   1620
caagctgccc gtgccctggc ccaccctcgt gaccaccctg acctacgcg tgcagtgctt   1680 cagccgctac cccgaccaca tgaagcagca cgacttcttc aagtccgcca tgcccgaagg   1740
ctacgtccag gagcgcacca tcttcttcaa ggacgacggc aactacaaga cccgcgccga   1800
ggtgaagttc gagggcgaca ccctggtgaa ccgcatcgag ctgaagggca tcgacttcaa   1860
ggaggacggc aacatcctgg ggcacaagct ggagtacaac tacaacagcc acaacgtcta   1920
tatcatggcc gacaagcaga agaacggcat caaggtgaac ttcaagatcc gccacaacat   1980
cgaggacggc agcgtgcagc tcgccgacca ctaccagcag aacaccccca tcggcgacgg   2040
ccccgtgctg ctgcccgaca accactacct gagcacccag tccgccctga gcaaagaccc   2100
caacgagaag cgcgatcaca tggtcctgct ggagttcgtg accgccgccg ggatcactct   2160
cggcatggac gagctgtaca agtaa                                         2185
```

<210> SEQ ID NO 54
<211> LENGTH: 2524
<212> TYPE: DNA
<213> ORGANISM: Artificial Sequence
<220> FEATURE:
<223> OTHER INFORMATION: mRFP-GFP-H2KK reporter construct

<400> SEQUENCE: 54

```
atggcctcct ccgaggacgt catcaaggag ttcatgcgct tcaaggtgcg catggagggc     60
tccgtgaacg gccacgagtt cgagatcgag ggcgagggcg agggccgccc ctacgagggc    120
acccagaccg ccaagctgaa ggtgaccaag ggcggccccc tgcccttcgc ctgggacatc    180
ctgtcccctc agttccagta cggctccaag gcctacgtga agcaccccgc cgacatcccc    240
gactacttga agctgtcctt ccccgagggc ttcaagtggg agcgcgtgat gaacttcgag    300
gacggcggcg tggtgaccgt gacccaggac tcctccctgc aggacggcga gttcatctac    360
aaggtgaagc tgcgcggcac caacttcccc tccgacggcc ccgtaatgca gaagaagacc    420
```

```
atgggctggg aggcctccac cgagcggatg taccccgagg acggcgccct gaagggcgag    480
atcaagatga ggctgaagct gaaggacggc ggccactacg acgccgaggt caagaccacc    540
tacatggcca agaagcccgt gcagctgccc ggcgcctaca agaccgacat caagctggac    600
atcacctccc acaacgagga ctacaccatc gtggaacagt acgagcgcgc cgagggccgc    660
cactccaccg cgcgccgaat tctcggtcct gcttttgcgcg aggatggtgg tgaaggatcc    720
agtgagcaag ggcgaggagc tgttcaccgg ggtggtgccc atcctggtcg agctggacgg    780
cgacgtaaac ggccacaagt tcagcgtgtc cggcgagggc gagggcgatg ccacctacgg    840
caagctgacc ctgaagttca tctgcaccac cggcaagctg cccgtgccct ggcccaccct    900
cgtgaccacc ctgacctacg gcgtgcagtg cttcagccgc taccccgacc acatgaagca    960
gcacgacttc ttcaagtccg ccatgcccga aggctacgtc caggagcgca ccatcttctt    1020
caaggacgac ggcaactaca agacccgcgc cgaggtgaag ttcgagggcg acaccctggt    1080
gaaccgcatc gagctgaagg gcatcgactt caaggaggac ggcaacatcc tggggcacaa    1140
gctggagtac aactacaaca gccacaacgt ctatatcatg gccgacaagc agaagaacgg    1200
catcaaggtg aacttcaaga tccgccacaa catcgaggac ggcagcgtgc agctcgccga    1260
ccactaccag cagaacaccc ccatcggcga cggccccgtg ctgctgcccg acaaccacta    1320
cctgagcacc cagtccgccc tgagcaaaga ccccaacgag aagcgcgatc acatggtcct    1380
gctggagttc gtgaccgccg ccgggatcac tctcggcatg gacgagctgt acaagcaatg    1440
tactaactac gctttgttga aactcgctgg cgatgttgaa agtaaccccg gtcctgctag    1500
catggcaccc tgcatgctgc tcctgctgtt ggcggccgcc ctggccccga ctcagacccg    1560
cgcgggccca cattcgctga ggtatttcca caccgccgtg tcccggcccg gcctcgggaa    1620
gccccggttc atctctgtcg gctacgtgga cgacacgcag ttcgtgcgct tcgacagcga    1680
cgcggagaat ccgaggtatg agccgcgggt gcggtggatg gagcaggtgg agcccgagta    1740
ttgggagcgg aacacgcaga tcgccaaggg caatgagcag attttccgag tgaacctgag    1800
gaccgcgctg cgctactaca accagagcgc gggcggctct cacacgttcc aacggatgta    1860
cggctgtgag gtggggtcgg actggcgcct cctccgcggg tacagcagt acgcatacga    1920
cggctgcgat tacatcgccc tgaacgaaga cctgaaaacg tggacggcgg ccgacatggc    1980
ggcgctgatc accaaacaca gtgggagca ggctggtgat gcagagagag accgggccta    2040
cctggagggc acgtgcgtgg agtggctccg cagatacctg cagctcggga acgcgacgct    2100
gccgcgcaca gattcccaa aggcccatgt gacccgtcac agcagacctg aagataaagt    2160
caccctgagg tgctgggccc tgggcttcta ccctgctgac atcaccctga cctggcagtt    2220
gaatggggag gagctgaccc aggacatgga gcttgtggag accaggcctg caggggatgg    2280
aaccttccag aagtgggcat ctgtggtggt gcctcttggg aaggagcagt attacacatg    2340
ccatgtgtac catcagggc tgcctgagcc cctcacctg agatgggagc ctcctccatc    2400
cactgtctcc aacacggtaa tcattgctgt tctggttgtc cttggagctg caatagtcac    2460
tggagctgtg gtggctttg tgatgaagat gagaaggaga acacaggtg aaaaggagg    2520
gtaa                                                                 2524
```

<210> SEQ ID NO 55
<211> LENGTH: 2542
<212> TYPE: DNA
<213> ORGANISM: Artificial Sequence
<220> FEATURE:
<223> OTHER INFORMATION: mRFP-HTP-GFP reporter construct

<400> SEQUENCE: 55

```
atggcctcct ccgaggacgt catcaaggag ttcatgcgct tcaaggtgcg catggagggc      60
tccgtgaacg gccacgagtt cgagatcgag ggcgagggcg agggccgccc ctacgagggc     120
acccagaccg ccaagctgaa ggtgaccaag gcggcccccc tgcccttcgc ctgggacatc     180
ctgtcccctc agttccagta cggctccaag gcctacgtga agcaccccgc cgacatcccc     240
gactacttga agctgtcctt ccccgagggc ttcaagtggg agcgcgtgat gaacttcgag     300
gacggcggcg tggtgaccgt gacccaggac tcctccctgc aggacggcga gttcatctac     360
aaggtgaagc tgcgcggcac caacttcccc tccgacggcc ccgtaatgca gaagaagacc     420
atgggctggg aggcctccac cgagcggatg taccccgagg acggcgccct gaagggcgag     480
atcaagatga ggctgaagct gaaggacggc ggccactacg acgccgaggt caagaccacc     540
tacatggcca agaagcccgt gcagctgccc ggcgcctaca agaccgacat caagctggac     600
atcacctccc acaacgagga ctacaccatc gtggaacagt acgagcgcgc cgagggccgc     660
cactccaccg gcgccgaatt ctcggtcctg cttttgcgcg aggatggtgg tgaaggatcc     720
tcaatgtact aactacgctt tgttgaaact cgctggcgat gttgaaagta accccggtcc     780
tgctagcatg aaaaagcctg aactcaccgc gacgtctgtc gagaagtttc tgatcgaaaa     840
gttcgacagc gtctccgacc tgatgcagct ctcggagggc gaagaatctc gtgctttcag     900
cttcgatgta ggagggcgtg gatatgtcct gcgggtaaat agctgcgccg atggtttcta     960
caaagatcgt tatgtttatc ggcactttgc atcggccgcg ctcccgattc cggaagtgct    1020
tgacattggg gagttcagcg agagcctgac ctattgcatc tcccgccgtg cacagggtgt    1080
cacgttgcaa gacctgcctg aaaccgaact gcccgctgtt ctgcagccgg tcgcggaggc    1140
catggatgcg atcgctgcgg ccgatcttag ccagacgagc gggttcggcc cattcggacc    1200
gcaaggaatc ggtcaataca ctacatggcg tgatttcata tgcgcgattg ctgatcccca    1260
tgtgtatcac tggcaaactg tgatggacga caccgtcagt gcgtccgtcg cgcaggctct    1320
cgatgagctg atgctttggg ccgaggactg ccccgaagtc cggcacctcg tgcacgcgga    1380
tttcggctcc aacaatgtcc tgacggacaa tggccgcata acagcggtca ttgactggag    1440
cgaggcgatg ttcggggatt cccaatacga ggtcgccaac atcttcttct ggaggccgtg    1500
gttggcttgt atggagcagc agacgcgcta cttcgagcgg aggcatccgg agcttgcagg    1560
atcgccgcgg ctccgggcgt atatgctccg cattggtctt gaccaactct atcagagctt    1620
ggttgacggc aatttcgatg atgcagcttg gcgcagggt cgatgcgacg caatcgtccg    1680
atccggagcc gggactgtcg ggcgtacaca atcgcccgc agaagcgcgg ccgtctggac    1740
cgatggctgt gtagaagtac tcgccgatag tggaaaccga cgcccagca ctcgtccgag    1800
ggcaaaggaa gtcgactcta gcatggtgag caagggcgag gagctgttca ccggggtggt    1860
gcccatcctg gtcgagctgg acggcgacgt aaacggccac aagttcagcg tgtccggcga    1920
gggcgagggc gatgccacct acggcaagct gaccctgaag ttcatctgca ccaccggcaa    1980
gctgcccgtg ccctggccca ccctcgtgac caccctgacc tacggcgtgc agtgcttcag    2040
ccgctacccc gaccacatga agcagcacga cttcttcaag tccgccatgc ccgaaggcta    2100
cgtccaggag cgcaccatct tcttcaagga cgacggcaac tacaagaccc gcgccgaggt    2160
gaagttcgag ggcgacaccc tggtgaaccg catcgagctg aagggcatcg acttcaagga    2220
ggacggcaac atcctggggc acaagctgga gtacaactac aacagccaca acgtctatat    2280
```

```
catggccgac aagcagaaga acggcatcaa ggtgaacttc aagatccgcc acaacatcga    2340
ggacggcagc gtgcagctcg ccgaccacta ccagcagaac acccccatcg gcgacggccc    2400
cgtgctgctg cccgacaacc actacctgag cacccagtcc gccctgagca agacccccaa    2460
cgagaagcgc gatcacatgg tcctgctgga gttcgtgacc gccgccggga tcactctcgg    2520
catggacgag ctgtacaagt ag                                             2542
```

```
<210> SEQ ID NO 56
<211> LENGTH: 40
<212> TYPE: DNA
<213> ORGANISM: Artificial Sequence
<220> FEATURE:
<223> OTHER INFORMATION: partial sequence of TP53 gene

<400> SEQUENCE: 56
ggcacccgcg tccgcgccat ggccatctac aagcagtcac                          40

<210> SEQ ID NO 57
<211> LENGTH: 45
<212> TYPE: DNA
<213> ORGANISM: Artificial Sequence
<220> FEATURE:
<223> OTHER INFORMATION: partial sequence of TP53 gene mutated by ZFN

<400> SEQUENCE: 57
ggcacccgcg tccgcgccat ggtatggcca tctacaagca gtcac                    45

<210> SEQ ID NO 58
<211> LENGTH: 44
<212> TYPE: DNA
<213> ORGANISM: Artificial Sequence
<220> FEATURE:
<223> OTHER INFORMATION: partial sequence of TP53 gene mutated by ZFN

<400> SEQUENCE: 58
ggcacccgcg tccgcgccat ggatggccat ctacaagcag tcac                     44

<210> SEQ ID NO 59
<211> LENGTH: 42
<212> TYPE: DNA
<213> ORGANISM: Artificial Sequence
<220> FEATURE:
<223> OTHER INFORMATION: partial sequence of TP53 gene mutated by ZFN

<400> SEQUENCE: 59
ggcacccgcg tccgcgccat atggccatct acaagcagtc ac                       42

<210> SEQ ID NO 60
<211> LENGTH: 45
<212> TYPE: DNA
<213> ORGANISM: Artificial Sequence
<220> FEATURE:
<223> OTHER INFORMATION: partial sequence of TP53 gene mutated by ZFN

<400> SEQUENCE: 60
ggcacccgcg tccgcgccca tgatggcca tctacaagca gtcac                     45

<210> SEQ ID NO 61
<211> LENGTH: 44
<212> TYPE: DNA
<213> ORGANISM: Artificial Sequence
<220> FEATURE:
<223> OTHER INFORMATION: partial sequence of TP53 gene mutated by ZFN

<400> SEQUENCE: 61
```
ggcacccgcg tccgcgccat ggatggccat ctacaagcag tcac                44

<210> SEQ ID NO 62
<211> LENGTH: 42
<212> TYPE: DNA
<213> ORGANISM: Artificial Sequence
<220> FEATURE:
<223> OTHER INFORMATION: partial sequence of TP53 gene mutated by ZFN

<400> SEQUENCE: 62
ggcacccgcg tccgcgccat atggccatct acaagcagtc ac                  42

<210> SEQ ID NO 63
<211> LENGTH: 41
<212> TYPE: DNA
<213> ORGANISM: Artificial Sequence
<220> FEATURE:
<223> OTHER INFORMATION: partial sequence of TP53 gene mutated by ZFN

<400> SEQUENCE: 63
ggcacccgcg tccgcgccca tggccatcta caagcagtca c                   41

<210> SEQ ID NO 64
<211> LENGTH: 50
<212> TYPE: DNA
<213> ORGANISM: Artificial Sequence
<220> FEATURE:
<223> OTHER INFORMATION: partial sequence of Thumpd3 gene

<400> SEQUENCE: 64
tcggcttccg gcggcgtgct cgcggtgcgg agaccggaag ggtctgtgct           50

<210> SEQ ID NO 65
<211> LENGTH: 45
<212> TYPE: DNA
<213> ORGANISM: Artificial Sequence
<220> FEATURE:
<223> OTHER INFORMATION: partial sequence of Thumpd3 gene mutated by ZFN

<400> SEQUENCE: 65
tcggcttccg gcggcgtgct cgcggagacc ggaagggtct gtgct                45

<210> SEQ ID NO 66
<211> LENGTH: 44
<212> TYPE: DNA
<213> ORGANISM: Artificial Sequence
<220> FEATURE:
<223> OTHER INFORMATION: partial sequence of Thumpd3 gene mutated by ZFN

<400> SEQUENCE: 66
tcggcttccg gcggcgtgct cgcgagaccg gaagggtctg tgct                 44

<210> SEQ ID NO 67
<211> LENGTH: 45
<212> TYPE: DNA
<213> ORGANISM: Artificial Sequence
<220> FEATURE:
<223> OTHER INFORMATION: partial sequence of Thumpd3 gene mutated by ZFN

<400> SEQUENCE: 67
tcggcttccg gcggcgtgct cgcggagacc ggaagggtct gtgct                45

<210> SEQ ID NO 68
<211> LENGTH: 36
<212> TYPE: DNA

<213> ORGANISM: Artificial Sequence
<220> FEATURE:
<223> OTHER INFORMATION: partial sequence of Thumpd3 gene mutated by ZFN

<400> SEQUENCE: 68
tcggcttccg gcggcgtgct cggaagggtc tgtgct                36

<210> SEQ ID NO 69
<211> LENGTH: 48
<212> TYPE: DNA
<213> ORGANISM: Artificial Sequence
<220> FEATURE:
<223> OTHER INFORMATION: partial sequence of Thumpd3 gene mutated by ZFN

<400> SEQUENCE: 69
tcggcttccg gcggcgtgct cgcggtggag accggaaggg tctgtgct                48

<210> SEQ ID NO 70
<211> LENGTH: 41
<212> TYPE: DNA
<213> ORGANISM: Artificial Sequence
<220> FEATURE:
<223> OTHER INFORMATION: partial sequence of Thumpd3 gene mutated by ZFN

<400> SEQUENCE: 70
tcggcttccg gcggcgtgcg gagaccggaa gggtctgtgc t                41

<210> SEQ ID NO 71
<211> LENGTH: 47
<212> TYPE: DNA
<213> ORGANISM: Artificial Sequence
<220> FEATURE:
<223> OTHER INFORMATION: partial sequence of Thumpd3 gene mutated by ZFN

<400> SEQUENCE: 71
tcggcttccg gcggcgtgct cgtgcggaga ccggaagggt ctgtgct                47

<210> SEQ ID NO 72
<211> LENGTH: 45
<212> TYPE: DNA
<213> ORGANISM: Artificial Sequence
<220> FEATURE:
<223> OTHER INFORMATION: partial sequence of Thumpd3 gene mutated by ZFN

<400> SEQUENCE: 72
tcggcttccg gcggcgtgct cgcggagacc ggaagggtct gtgct                45

<210> SEQ ID NO 73
<211> LENGTH: 47
<212> TYPE: DNA
<213> ORGANISM: Artificial Sequence
<220> FEATURE:
<223> OTHER INFORMATION: partial sequence of Thumpd3 gene mutated by ZFN

<400> SEQUENCE: 73
tcggcttccg gcggcgtgct cgcgcggaga ccggaagggt ctgtgct                47

<210> SEQ ID NO 74
<211> LENGTH: 48
<212> TYPE: DNA
<213> ORGANISM: Artificial Sequence
<220> FEATURE:
<223> OTHER INFORMATION: partial sequence of Thumpd3 gene mutated by ZFN

<400> SEQUENCE: 74
tcggcttccg gcggcgtgct cgctgcggag accggaaggg tctgtgct                48

```
<210> SEQ ID NO 75
<211> LENGTH: 9
<212> TYPE: PRT
<213> ORGANISM: Artificial Sequence
<220> FEATURE:
<223> OTHER INFORMATION: conserved sequence of amino acids found in
      meganuclease family

<400> SEQUENCE: 75

Leu Ala Gly Leu Ile Asp Ala Asp Gly
1               5

<210> SEQ ID NO 76
<211> LENGTH: 6
<212> TYPE: PRT
<213> ORGANISM: Artificial Sequence
<220> FEATURE:
<223> OTHER INFORMATION: conserved sequence of amino acids found in
      meganuclease family

<400> SEQUENCE: 76

Gly Ile Tyr Tyr Ile Gly
1               5
```

METHOD FOR CONCENTRATING CELLS THAT ARE GENETICALLY ALTERED BY NUCLEASES

RELATED APPLICATIONS

This application is a National Phase of PCT Patent Application No. PCT/KR2012/001367 having International filing date of Feb. 22, 2012, which claims the benefit of priority of U.S. Provisional Patent Application Ser. No. 61/445,346 filed on Feb. 22, 2011 and Korean Patent Application No. 10-2011-0093704 filed on Sep. 16, 2011. The contents of the above applications are all incorporated by reference as if fully set forth herein in their entirety.

SEQUENCE LISTING STATEMENT

The ASCII file, entitled 57320SequenceListing.txt, created on Aug. 22, 2013, comprising 65,382 bytes, submitted concurrently with the filing of this application is incorporated herein by reference.

TECHNICAL FIELD

The present invention relates to a reporter construct and method for identifying, selecting, or enriching the cells, wherein an endogenous nucleotide sequence is cleaved by a specific nuclease or modified by the cleavage; a host cell comprising the reporter construct; and a system for monitoring nuclease activity.

BACKGROUND ART

Synthetic nucleases such as meganucleases, zinc-finger nucleases (ZFNs), and TAL-effector nucleases (TALENs) are powerful and versatile tools for genome engineering to induce endogenous gene disruption, targeted gene addition, and chromosomal rearrangements in cells and organisms and thus are broadly useful in research, biotechnology, and medical fields.

The synthetic nucleases recognize a specific target nucleotide sequence and induce site-specific DNA double strand breaks (DSBs) in the genome, whose integrity is restored via endogenous DNA repair systems known as non-homologous end joining (NHEJ) and homologous recombination (HR), resulting in targeted mutagenesis and gene modification. In the absence of homologous donor DNA, DSBs are mainly repaired by NHEJ, a dominant repair system over HR in higher eukaryotic cells and organisms. Gene modification by HR is done by exact replication of the sequence of HR donor DNA, whereas NHEJ causes random gene modification. As NHEJ is intrinsically error-prone, small insertions and deletions (indels) may be generated at the DSB site, which then leads to genetic mutations by inducing frame-shift mutations.

Even though zinc-finger nuclease and TAL-effector nuclease are useful tools for designing a genetic modification in eukaryotic cells and organisms, a use thereof is highly limited. This is because in general, it is highly difficult to distinguish a mutant cell having a genetic mutation induced by a synthetic nuclease and a wild-type cell phenotypically, making it difficult to isolate mutant cells only.

In other words, one of the biggest roadblocks to apply synthetic nucleases in gene therapy and basic research is a lack of systems to enrich or select gene-modified cells. For example, the therapeutic efficacy of ZFNs that induce targeted disruption of the human chemokine receptor 5 (CCR5) gene which encodes a co-receptor of human immunodeficiency virus (HIV) largely depends on the number of CCR5-knockout cells induced by ZFNs. However, only a limited fraction of cells are mutated by the ZFNs and the remaining cells with at least one copy of the intact CCR5 gene will serve as hosts for HIV replication. Furthermore, laborious screening of numerous clones is often required to obtain gene-disrupted cells because only a minor fraction of cells are modified by nucleases. Also, even if CCR5-knockout cells can be selectively proliferated in vivo due to immunity against HIV infection, the enrichment of mutant cells prior to transplanting them will increase the potential therapeutic efficacy thereof.

Furthermore, a gene modifying function of synthetic nuclease allows the generation of gene-modified transformants, which can be applied to a large scale production of useful proteins and the treatment of incurable diseases. However, when producing transformed animals from large animals such as pigs and cows, a direct injection of ZFN mRNA into a fertilized egg at pronucleus stage has very low transformation efficacy due to mosaicism occurred during the generation of fertilized egg. Thus, as a reproduction method, nuclear transplantation, which injects the transformants generated by ZFN into an donor nucleus, is mostly used, and for this method, a large amount of transformants are required. For a large-scale production of transformants, an efficient method is required for selecting the transformants whose genes are modified by ZFN, through introducing a plasmid comprising ZFN DNA into the cell. Therefore, if a method for enriching or isolating the cells, whose target genes are modified by synthetic nuclease, in a high ratio can be established, it would be widely used in various areas where a synthetic nuclease can be applied.

SUMMARY OF THE INVENTION

Technical Problem

The present inventors have found that after a reporter construct comprising a target sequence and reporter gene recognized by a specific nuclease is prepared and introduced into the cells which can express the nuclease and then the cells expressing reporter gene are separated from those not expressing the same, a group of the cells expressing the reporter gene showed a higher proportion of the cells, wherein a specific endogenous nucleotide sequence is cleaved by the nuclease and modified by such cleavage, compared to a group of the cells not expressing the reporter gene; and have developed the present method for enriching the cells wherein the nucleotide sequence is modified by the nuclease, thereby completing the present invention.

Technical Solution

One object of the present invention is to provide a method for identifying or enriching the cells, wherein a specific endogenous nucleotide sequence is cleaved by a specific nuclease or modified by such cleavage.

Another object of the present invention is to provide a reporter construct for identifying, selecting, or enriching the cells, wherein a specific endogenous nucleotide sequence is cleaved by a specific nuclease or modified by such cleavage.

Another object of the present invention is to provide a reporter construct comprising a first reporter gene, a target sequence recognized by the nuclease, a second reporter gene, and a third reporter gene.

Another object of the present invention is to provide a host cell comprising the reporter construct.

Another object of the present invention is to provide a system for monitoring nuclease activity.

Advantageous Effect

The reporter system of the present invention and the method for enriching the gene-modified cells by nuclease by using the reporter system can isolate a cell population where the cells mutated by nuclease exist in a high ratio, and obtain a population of live mutant cells, and thus they can be efficiently used in gene therapy or cell therapy.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIGS. 1a-b show the nucleotide sequence encoding a pair of zinc finger nuclease (ZFN) which targets TP53 gene. DNA-recognizing helix of each domain of ZFN pair is underlined. The previously known ZFN targets exon 7 of TP53 gene, whereas the ZFN used in the present invention targets exon 5 of TP53 gene.

FIG. 2 shows the sequence of TP53 reporter construct. A recognition site for ZFN is underlined.

FIGS. 3a-b are schematic diagram showing a structure of reporter construct and a method for enriching the gene-modified cells by using the reporter construct. FIG. 3(a) shows the structure of reporter construct. The reporter construct consists of mRFP gene, a target sequence for synthetic nuclease, and eGFP gene. FIG. 3(b) is a schematic diagram describing a method for sorting and analyzing the cells via flow cytometry. The cells were transfected with a reporter plasmid and a plasmid encoding a nuclease and after 3 or 4 days, the cells were analyzed by flow cytometry.

FIG. 4(b) is a schematic diagram showing a structure of HR reporter and a method for enriching the gene-modified cells by using the reporter system. A target site for nuclease was inserted into an eGFP gene to generate an inactive recombination acceptor. A truncated, inactive eGFP gene is used as a HR donor. A DSB generated by nuclease is repaired by HR, generating a functional eGFP gene.

FIG. 5 shows the expression pattern of RFP and GFP observed under fluorescent microscope, after co-transfecting HEK293 cells with a reporter plasmid and a plasmid encoding ZFN pair. The measurement of expression was done on the $1^{st}$, $2^{nd}$, and $3^{rd}$ day after co-transfection, and the scale bar is 100 μm.

FIGS. 6a-d show the enrichment of TP53 gene-modified cells using a surrogate reporter. FIG. 6(a) shows the result of flow cytometry analysis on HEK293 after 3 days of the co-transfection of the cells with a TP53-targeting ZFN and reporter. FIG. 6(b) shows the ZFN-driven mutations detected by T7E1 assay. Arrows indicate the positions of DNA bands cleaved by mismatch-sensitive T7E1. The numbers at the bottom of the gel indicate mutation frequencies measured by band intensities. FIG. 6(c) shows the ZFN-driven mutation rates measured by fluorescent PCR. Arrows indicate amplified DNA peaks corresponding to small insertions. Tallest peaks correspond to wild-type amplicons. Mutation rates are calculated by measuring the peak area. FIG. 6(d) shows the DNA sequences of the TP53 gene targeted by ZFN. The ZFN recognition sites are underlined. Dashes indicate deleted bases, and small bold letters indicate the inserted bases. The number of mutations is shown in parenthesis. Mutation frequencies are calculated by dividing the number of mutant clones by a total number of clones (WT: wild-type sequence).

FIGS. 7a-c shows the enrichment of CCR5 gene-modified cells by ZFN-224 by using a surrogate reporter. FIG. 7(a) shows the result of flow cytometry analysis on the transfected cells. FIG. 7(b) shows the results of T7E1 assay on the genomic DNA isolated from the cells sorted by flow cytometry. Arrows indicate the expected positions of DNA bands cleaved by T7E1. FIG. 7(c) shows the result of fluorescent PCR for determining the indel mutation rate in the CCR5 gene. Arrows indicate the amplified DNA peaks corresponding to small insertions.

FIGS. 8a-c shows the enrichment of CCR5 gene-modified cells by Z891 using a surrogate reporter. FIG. 8(a) shows the result of flow cytometry of transfected cells, and FIG. 8(b) shows the result of T7E1 assay on the genomic DNA isolated from the cells sorted by flow cytometry, and FIG. 8(c) shows the result of fPCR.

FIGS. 9a-b show the enrichment of CCR5 gene-modified cells by TALEN, by using a surrogate reporter. FIG. 9(a) shows the result of flow cytometry analysis on transfected HEK293 cells, and FIG. 9(b) shows the result of T7E1 assay on the genomic DNA isolated from the cells sorted by flow cytometry. Arrows indicate the amplicons cleaved by T7E1, and relative band density shows TALEN activity.

FIGS. 10a-b show the enrichment of Thumpd3 gene-modified mouse cells, by using a surrogate reporter. Mouse fibroblast cells derived from pluripotent stem cells were co-transfected with a reporter plasmid and a plasmid encoding ZFN pair which targets Thumpd3 gene, and analyzed. FIG. 10(a) shows the results of flow cytometry analysis on the transfected cells and FIG. 10(b) shows the result of T7E1 assay on the genomic DNA isolated from the cells sorted by flow cytometry. Arrows indicate the amplicons cleaved by T7E1. Relative band density shows ZFN activity.

FIGS. 11a-b shows the result of replication analysis on a single cell and cell population (colony). FIG. 11(a) shows the sequence analysis results. Mouse fibroblast cells derived from pluripotent stem cells were co-transfected with a reporter plasmid and a plasmid encoding ZFN pair which targets Thumpd3 gene. Then the cells were sorted by flow cytometry, and single cells were isolated by using a mouth pipette under microscope and transferred to PCR tube. PCR products of 21 unsorted cells and 10 sorted cells were replicated and analyzed for their sequences. Clone 1a and 1b show the DNA sequences obtained from a single clone with biallelic mutation. FIG. 11 (b) shows the result of replication analysis on cell population.

FIGS. 12a-c show the mutation rates and level of nuclease in the sorted cells. FIG. 12(a) shows the sorting of the cells to RFP$^{dim}$, RFP$^{medium}$, and RFP$^{bright}$ cells, and to RFP$^{31}$GFP$^+$ and RFP$^+$GFP$^+$ cells by flow cytometry. FIG. 12(b) shows the T7E1 assay on the sorted cells. Bands indicated by arrows indicate amplicons cleaved by T7E1, and relative band density indicates ZFN activity. FIG. 12(c) shows the western blotting of HA-tagged ZFN to determine protein level thereof. GAPDH was used as an internal control.

FIG. 13 demonstrates the increased enrichment of the gene-modified cells by repeating the process of co-transfection and cell sorting. When the cells were co-transfected with a reporter plasmid and a plasmid encoding ZFN, and the cell sorting process by flow cytometry was repeated twice, it was observed that the CCR5 gene-modified mutant cells could be enriched at greater extent.

FIGS. 14a-b show a schematic diagram of a method for enriching target gene-modified cells by magnetic-activated cell sorting (MACS). FIG. 14(a) shows the structure of a reporter construct which consists of mRFP gene, a target sequence of synthetic nuclease, 2A-peptide sequence, and mouse MHC class I molecule H-2K$^k$ gene. FIG. 14(b) shows the method for sorting the transfected cells. The cells were co-transfected with a reporter plasmid and a plasmid encoding nuclease, and after 3 or 4 days of transfection, the cells were marked with H-2K$^k$-specific magnetic beads, and sorted in the MACS column by magnetic force.

FIG. 15 shows the results of sorting and enriching the CCR5 gene-modified cells by ZFN-224, by using a reporter and MACS. The cells were co-transfected with a reporter plasmid and a plasmid encoding ZFN, and the cells selected by magnetic-beads in MACS were sorted twice. Then the sorted cells were analyzed by T7E1 assay.

FIG. 16 shows the DNA sequence of A TALEN double frame reporter construct. The underlined and bold part indicates a target sequence recognized by nuclease.

FIG. 17 shows the DNA sequence of B TALEN double frame reporter construct. The underlined and bold part indicates a target sequence recognized by nuclease.

FIG. 18 shows a structure of double frame NHEJ reporter construct and a schematic diagram of how the reporter works.

FIG. 19 shows the measurement of whether prime changes can be detected in two cases where a double frame NHEJ reporter construct and a single frame reporter construct are used.

FIG. 20 shows a structure of reporter construct for hygromycin selection and a schematic diagram of how the reporter construct works.

FIG. 21 shows a schematic diagram for the process of generating transformant cell line by using a hygromycin reporter selection method.

FIG. 22 shows expression level of RFP and GFP in the cell populations prior to hydromycin treatment, without hygromycin treatment, and with hygromycin treatment.

FIG. 23 shows the T7E1 assay result for determining the proportion of transformants in the cells selected by hygromycin treatment.

FIG. 24 shows the nucleotide sequence of a reporter construct comprising mRFP-GFP-H2KK. The reporter construct was designed in a way that a target sequence for CMAH-ZFN is positioned downstream of mRFP gene, and the eGFP gene, 2A peptide, and H2KK gene are positioned out of frame. Also, mRFP-eGFP fusion protein and H2KK protein are positioned such that they can be expressed separately by 2A-peptide (for the sequence of a target sequence of CMAH-ZFN and the sequence of 2A-peptide, refer to figure label).

FIG. 25 shows the nucleotide sequence of a reporter construct comprising mRFP-HTP-GFP. The reporter construct was designed in a way that a target sequence for CMAH-ZFN is positioned downstream of mRFP gene, and the 2A peptide, HTP gene, and eGFP gene are positioned out of frame. Also, mRFP protein and HTP-eGFP protein are positioned such that they can be expressed separately by 2A-peptide (for the sequence of a target sequence of CMAH-ZFN and the sequence of 2A-peptide, refer to figure label).

DESCRIPTION OF SPECIFIC EMBODIMENTS OF THE INVENTION

Figure 4:
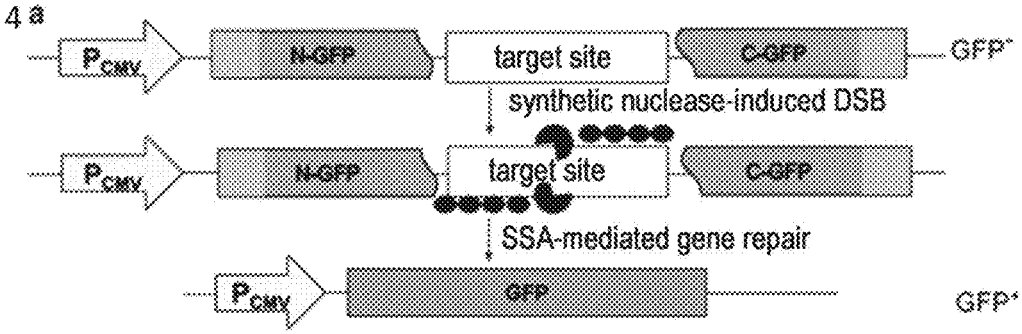
FIGS. 4a-b: 4(a) is a schematic diagram showing a structure of SSA reporter and a method for enriching the gene-modified cells by using the reporter system. A target site for nuclease was inserted in between N-GFP and C-GFP, and the bold part indicates a partially duplicated sequence.
Figure 4:
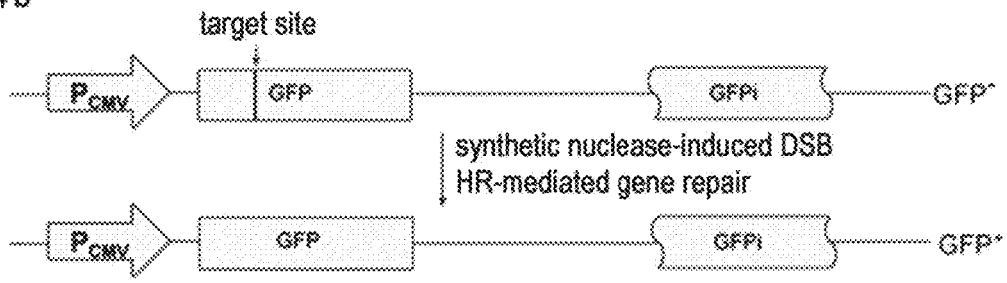

One aspect of the present invention relates to a method for identifying or enriching the cells, wherein a specific endogenous nucleotide sequence is cleaved by a specific nuclease or modified by such cleavage, wherein the method comprises a first step of preparing a reporter construct comprising a target sequence recognized by the nuclease and a reporter gene, wherein the expression of the reporter gene in the reporter construct is determined by the binding of the nuclease to the target sequence and cleaving the reporter construct; a second step of introducing the reporter construct to candidate cells, wherein a portion or all of the candidate cells express the nuclease before or after incorporating the reporter construct; and a third step of sorting the candidate cells obtained from step 2 into a group of cells expressing the reporter gene or a group of cells not expressing the reporter gene.

The second aspect of the present invention relates to a reporter construct for identifying, selecting, or enriching the cells, wherein a specific endogenous nucleotide sequence is cleaved by a specific nuclease or modified by such cleavage, comprising a first reporter gene, a target sequence recognized by the nuclease, and a second reporter gene, wherein the expression of the second reporter gene is determined by the binding of the nuclease to the target sequence and cleaving the reporter construct.

Third aspect of the present invention relates to a reporter construct comprising a first reporter gene, a target sequence recognized by the nuclease, a second reporter gene, and a third reporter gene, wherein the first reporter gene is expressed regardless of the binding of the nuclease to the target sequence and cleavage of reporter construct, and the expression of the second reporter gene or the third reporter gene, or expression of both are determined by the binding of the nuclease expressed in the cell to the target sequence and cleaving the reporter construct.

The fourth aspect of the present invention relates to a host cell comprising the reporter construct.

The fifth aspect of the present invention relates to a system for monitoring the nuclease activity, comprising the reporter construct; host cell; and nuclease-expressing construct, wherein the reporter construct, the nuclease-expressing construct, or both are introduced into the host cell or are prepared aside from the cell.

Hereinafter, the present invention is described in more detail.

A nuclease, which can cleave a phosphodiester bond between nucleotides of endogenous gene in the cells and organisms, can be useful in designing genetic modification. However, since there is no system developed for isolating and enriching only the cells whose genes are modified by nuclease, a use of nuclease has been limited.

In this regard, as one aspect the present invention provides a method for identifying or enriching the cells, wherein a specific endogenous nucleotide sequence is cleaved by a specific nuclease or modified by such cleavage.

The specific endogenous nucleotide sequence may be an intrinsic nucleotide sequence present in the genome. The specific nuclease can cleave the specific nucleotide sequence by binding to an intrinsic target sequence present in the genome.

Also, in the method for identifying or enriching the mutant cells having the nucleotide sequence modified, the type of mutation includes not only a local mutation, but also chromosomal rearrangements such as deletion, insertion, inversion, duplication, and translocation, but is not limited thereto.

To be specific, the method comprises a first step of preparing a reporter construct comprising a target sequence recognized by the nuclease and a reporter gene, wherein the expression of the reporter gene in the reporter construct is determined by the binding of the nuclease to the target sequence and cleaving the reporter construct; a second step of introducing the reporter construct to candidate cells, wherein a portion or all of the candidate cells express the nuclease before or after incorporating the reporter construct; and a third step of sorting the candidate cells obtained from step 2 into a group of cells expressing the reporter gene or a group of cells not expressing the reporter gene.

The method of the present invention is characterized in that it uses a reporter construct.

The reporter construct can be designed such that it comprises a target sequence recognized by nuclease and a reporter gene, and that the expression of the reporter gene is determined by the binding of the nuclease to the target sequence and cleaving the reporter construct.

As one embodiment of the present invention, the reporter construct can be designed in a way that a target sequence recognized by the nuclease is inserted in the middle or upstream of a reporter gene, and that the expression of the reporter gene is determined by the binding of the nuclease to the target sequence and cleaving the reporter construct. As an example, the reporter construct may be designed such that if the nuclease binds to the target sequence but does not cleave the reporter construct, then the reporter gene is not expressed; however, if the nuclease cleaves the reporter construct by binding to the target sequence, then the cleaved DNA is repaired by a homologous recombination (HR), a single strand annealing (SSA) system, or NHEJ present in the cell or organism, thereby inducing the expression of reporter gene.

The reporter construct of the present invention can be designed such that when a specific target sequence is cleaved by nuclease, the reporter gene can be expressed by HR or SSA system.

The reporter construct according to one embodiment of the present invention has a target sequence recognized by specific nuclease inserted in the middle of GFP, so that the C-terminal of GFP is out of frame with the N-terminal of GFP. If the nuclease cleaves the reporter construct by binding to the target sequence, this induces double strand break (DSB), however DSB of the gene can be repaired by SSA system, thereby allowing the expression of GFP.

The reporter construct of the present invention can be designed such that when a specific target sequence is cleaved by nuclease, small insertion/deletion occurs by NHEJ system, thereby inducing a frame-shift mutation in the reporter construct.

The reporter construct by HR or SSR system may express a reporter protein when nuclease acts on it, regardless of frame-shift; however, it has a problem of spontaneous mutation occurring without nuclease. That is, without the nuclease activity, about 1 to 5% of the cells can express a reporter gene, and thus only the cells whose genes are modified by nuclease cannot be correctly selected.

However, the reporter construct according to one embodiment of the present invention is a reporter construct that can be used with NHEJ system, and only less than 1% or below 0.1% of the cells express a reporter protein without nuclease. Therefore, using the present reporter construct, the gene-modified cells by nuclease can be correctly selected and enriched.

As one specific embodiment of the reporter construct of the present invention, the reporter construct may be designed such that it comprises a first reporter gene, a target sequence recognized by the nuclease, and a second reporter gene successively, wherein the expression of the second reporter gene is determined by the binding of the nuclease expressed in the cell to the target sequence and cleaving the reporter construct. Also, a stop codon may be inserted upstream of the second reporter gene. To be more specific, one may use a reporter construct, wherein the target sequence recognized by the nuclease is inserted in between the first reporter gene and the second reporter gene, and the second reporter gene is out of frame with the first reporter gene. In this case, if the nuclease does not bind to the target sequence and cleave the construct, only the first reporter gene is expressed. On the other hand, if the nuclease binds to the target sequence and cleaves the reporter construct, the cleaved DNA may have small insertion/deletion mutations (i.e., indel mutations) by nonhomologous end joining (NHEJ) system, thereby inducing a frame-shift mutation, which may allow the first reporter gene and the second reporter gene to be in frame. That is, with this frame-shift, both of the first reporter gene and the second reporter gene can be expressed.

As another embodiment of the reporter construct, the reporter construct may be designed such that it comprises a first reporter gene, a target sequence recognized by the nuclease, a second reporter gene, and a third reporter gene successively, wherein the first reporter gene is expressed regardless of the binding of nuclease to the target sequence and the cleavage of reporter construct, whereas the second reporter gene, the third reporter gene, or both are expressed depending on the binding of the nuclease expressed in the cell to the target sequence and the cleavage of the reporter construct.

It is preferable that the reporter construct is designed in a way that the second reporter gene and the third reporter gene is connected with the first reporter gene out of frame, so that they can be expressed only when the nuclease binds to a specific target sequence and cleaves the reporter construct, inducing frame-shift mutation.

In the reporter construct, the second reporter gene and the third reporter gene may be connected out of frame. In this case, if a nuclease target sequence inserted in between the first reporter gene and the second reporter gene is cleaved by a nuclease, then this induces a frame-shift in amino acid codon and the second reporter gene or the third reporter gene may be expressed. Through this method, one can select the mutant cell having two types of frame-shifts generated by nuclease cleaving the target site at once. That is, one can select the mutant cells having frame-shift mutation caused by shift of one and two amino acids by nuclease activity. Also, by introducing more than 1 or 2 reporter constructs into the cell, the cells having a frame-shift mutation caused by shift of 3 units of amino acid sequences can be selected.

In one example of the present invention, when a reporter construct comprises only a first reporter gene and a second reporter gene out of amino acid codon frame, only those cells having one type of frame-shift mutation could be selected. On the other hand, when a reporter construct comprises a first reporter gene along with a second reporter gene and a third reporter gene out of amino acid codon frame, the cells having two types of frame-shift mutations could be selected.

Also, in the reporter construct, the second reporter gene and the third reporter gene may be connected in frame.

In the reporter construct, the second reporter gene and the third reporter gene may be the same type or different types of reporter genes.

If the second reporter gene and the third reporter gene are in frame and the same type of reporter gene, the expression level of reporter gene induced by the cleavage of a target sequence by nuclease increases, and thus the gene-modified cells by nuclease can be selected more correctly or enriched.

If the second reporter gene and the third reporter gene are in frame and are different types of reporter genes, then the expression of second reporter gene can be used for MACS and drug selection, and also for confirming the enrichment of mutant cells.

In one example of the present invention, as one embodiment of the reporter construct, the reporter construct comprising a first reporter gene encoding RFP, which is expressed regardless of the nuclease activity; a target sequence recognized by the nuclease; and a second reporter gene encoding antibiotic resistance gene (HPT) and a third reporter gene encoding GFP, which are positioned out of frame with the first reporter gene, was prepared. The reporter construct expressed GFP, but not the HPT-GFP fusion protein in the absence of ZFN. When the ZFN and reporter were co-transfected into the cell and the ZFN correctly cleaved the target sequence within the reporter, then small insertion/deletion occurred randomly by NHEJ, making the HPT gene and RFP gene in frame in some reporters and HPT enzyme could be expressed. Cells comprising the reporters with such mutation would be resistant to hygromycin B, and thus these cells having their genes modified by nuclease can be easily selected by using antibiotics. Also, as HPT gene is linked to GFP gene, the activity of ZFN can be easily determined by monitoring fluorescence. That is, after performing MACS and drug selection, the proper enrichment of mutant cells can be confirmed indirectly by monitoring the expression of fluorescent proteins.

Therefore, the expression of reporter gene can reflect the activity of nuclease which binds to the endogenous target sequence thereof present in the genome and cleaves a specific nucleotide sequence.

Also, the method of the present invention comprises the step of introducing the reporter construct to a candidate cell, and the step of sorting the cells into the cells expressing the reporter gene and those not expressing the reporter gene.

When the reporter construct is introduced into a candidate cell, a portion or all of the candidate cells can express the nuclease before or after insertion of the reporter construct. Also, the nuclease expressed in the second step of the method may be the nuclease that is directly inserted into the cell. The nuclease may be the one expressed from an exogenous nuclease gene or endogenous nuclease gene in the candidate cell.

Also, the nuclease may be introduced into the cell from external sources through transformation, electroporation, or virus delivery, or it may be expressed in the cell by inserting the corresponding gene into the genome.

Furthermore, one or two or more reporter constructs may be inserted into the cell.

The type of sorting method is not limited, as long as it can separate the cells expressing the reporter gene from the cells not expressing the same. In one embodiment of the present invention, the cells can be sorted by fluorescence-activated cell sorting (FACS) or magnetic-activated cell sorting (MACS). As another embodiment, the cells whose endogenous gene is mutated can be enriched by using an antibiotic resistance gene as a reporter and by selecting the cells survived after antibiotic treatment.

When a reporter construct comprising a first reporter gene, a target sequence recognized by a specific nuclease, and a second reporter gene successively is used, the cells can be divided into a group of cells expressing both of the first reporter gene and the second reporter gene, a group of cells expressing the first reporter gene only, and a group of cells expressing neither of the reporter genes.

Meanwhile, when a reporter construct comprising a first reporter gene, a target sequence recognized by a specific nuclease, a second reporter gene, and a third reporter gene successively is used, the cells can be divided into a group of cells expressing all of the first reporter gene, the second reporter gene, and the third reporter gene, a group of cells expressing the first reporter gene only, a group of cells expressing the first and second reporter genes only, and a group of cells expressing the first and third reporter genes only.

In one example of the present invention, it was observed that a proportion of the cells, wherein a specific nucleotide sequence is cleaved by a specific nuclease or modified by such cleavage, was significantly increased in the cell population expressing the reporter genes (i.e., the cell population expressing both of the first reporter gene and the second reporter gene, when a reporter construct comprising two reporter genes is used), compared to the cell population which does not express reporter gene.

Also, in the method of the present invention, the steps 2 and 3 can be repeated twice or more. In one example of the present invention, it was found that when the steps 2 and 3 were repeated twice, the number of gene-modified cells was significantly increased in the cell population, compared to when the two steps were performed once.

Therefore, by using the method of the present invention, one can identify, select, or enrich the cells, wherein a specific nucleotide sequence thereof is cleaved by a specific nuclease, or modified by such cleavage, in a high ratio.

In addition, the scope of the present invention includes a method for identifying the activity of certain nuclease, by performing the steps 1 to 3. If a nuclease is expressed in a candidate cell which is inserted with the reporter construct, and cleaves a target sequence within the reporter gene, then the reporter gene can be expressed. Therefore, by monitoring the expression of reporter gene, one can determine whether a nuclease has the activity of cleaving a specific nucleotide sequence.

As another aspect, the present invention provides a reporter construct for identifying, selecting, or enriching the cells, wherein a specific nucleotide sequence is cleaved by a specific nuclease, or modified by such cleavage.

The construct comprises a first reporter gene, a target sequence recognized by the nuclease, and a second reporter gene, wherein the expression of the second reporter gene is determined by the binding of the nuclease to the target sequence and cleaving the reporter construct.

The construct may comprise a first reporter gene, a target sequence recognized by the nuclease and a second reporter gene successively.

If a specific nuclease cleaves a specific nucleotide sequence in the reporter construct, then the cleaved DNA can be repaired by homologous recombination (HR) or nonhomologous end joining (NHEJ) system which has high chance of causing frame-shift mutation, thereby allowing the expression of both the first reporter gene and the second reporter gene.

Also, the construct can be designed to comprise a first reporter gene, a target sequence recognized by the nuclease, a second reporter gene, and a third reporter gene, wherein the first reporter gene is expressed regardless of the binding of the nuclease to the target sequence and cleaving the reporter construct, and the expressions of the second reporter gene, the third reporter gene, or both are determined by the binding of the nuclease expressed in the cells to the target sequence and cleaving the reporter construct.

The construct may comprise a first reporter gene, a target sequence recognized by the nuclease, a second reporter gene, and a third reporter gene successively.

It is preferable that the second reporter gene and the third reporter gene are connected with the first reporter gene out of frame, while the second reporter gene and the third reporter gene may be connected out of frame, or in frame with each other.

The expression of reporter gene reflects the nuclease activity which can bind to a target sequence thereof and cleaves a specific nucleotide sequence. The reporter construct can be used for identifying, selecting, or enriching the cells, wherein a specific nucleotide sequence in the cell is cleaved by an active nuclease or modified by such cleavage.

The reporter construct may be a vector, and preferably a plasmid.

As another aspect, the present invention provides a host cell that comprises one or more than two or more of the reporter construct of the present invention which is for identifying, selecting, or enriching the cells, wherein a specific nucleotide sequence in the cell is cleaved by a specific nuclease or modified by such cleavage.

The host cell may be used to reflect the activity of a specific nuclease which binds to a target sequence and cleaves a specific nucleotide sequence.

As another aspect, the present invention provides a system for monitoring the nuclease activity, comprising one or two or more reporter constructs of the present invention for identifying, selecting, or enriching the cells, wherein a specific nucleotide sequence is cleaved by a specific nuclease or modified by such cleavage; a host cell; and a construct expressing the nuclease.

In the system, the reporter construct, the construct expressing the nuclease, or both may be already inserted in the host cell or prepared aside from the cell. Also, the nuclease may be the one expressed from exogenous nuclease gene or endogenous nuclease gene of the host cell. The nuclease may be directly introduced from outside into the cell through transformation, electroporation, and virus delivery, or expressed from a corresponding gene inserted in the genome of the cell.

Also, the nuclease and reporter construct may be introduced concurrently or successively.

Definitions

As used herein, the term "cleavage" refers to the breakage of the covalent backbone of a DNA molecule. Cleavage may be induced by various methods, including enzymatic or chemical hydrolysis of a phosphodiester bond, but is not limited thereto. Both single-strand cleavage and double-strand cleavage are possible, in which double-strand cleavage may occur as a result of cleaving two separate single strands.

As used herein, the term "binding" refers to a sequence-specific, or non-covalent interaction between macromolecules (e.g., between a protein and a nucleic acid). Not all components involved in binding interaction need be sequence-specific (e.g., contacts with phosphate residues in a DNA backbone), as long as the interaction as a whole is sequence-specific. Such interactions generally have a dissociation constant ($K_d$) of $10^{-6}M^{-1}$ or lower.

As used herein, "target site" or "target sequence" refers to a nucleotide sequence that defines a portion of nucleotide sequence to which a binding molecule will bind, provided a sufficient condition for binding exists. These terms can be used interchangeably with "recognition site" or "recognition sequence".

As used herein, the term "gene" refers to a molecular unit of heredity that can be transferred from a parent to offspring, including DNA, RNA, or protein encoded therefrom.

As used herein, "episome" refers to a replicating nucleic acid, nucleoprotein complex or other structure comprising a nucleic acid that is not part of the chromosomal karyotype of a cell. Examples of episomes include plasmids and certain viral genomes.

As used herein, "exogenous" molecule refers to a molecule that is not normally present in the cell, but may be introduced into the cell through more than one genetic, biochemical, or other methods. Being "normally present in the cell" is determined by a certain developmental stage of the cell and environmental conditions. For instance, a molecule that is present only during embryonic development of muscle is an exogenous molecule with respect to an adult muscle cell. An exogenous molecule may be a small molecule generated by a combinational chemistry process, or a macromolecule such as a protein, nucleic acid, carbohydrates, lipids, glycoproteins, lipoproteins, polysaccharides, any modified derivatives thereof, or any complex comprising one or more of the above molecules.

In contrast, "endogenous" molecule refers to a molecule that is normally present in a particular cell at a certain developmental stage under specific environmental conditions. For example, an endogenous nucleic acid includes the genome of a mitochondrion, chlorophyll, or other organelle, or naturally-occurring episomal nucleic acid. In addition, endogenous molecules may include proteins such as transcription factors and enzymes.

As used herein, the term "vector" refers to a nucleic acid molecule that can deliver other nucleic acids connected thereto. Examples of such vector include plasmid, cosmid, bacteriophage, and viral vector, but are not limited thereto. As one type of vector, "plasmid" refers to a circular double-stranded DNA loop wherein additional DNA fragment can be linked.

The vector of the present invention may induce the expression of a gene encoding a target protein, which is operably linked thereto, and such vector is called "expression vector". A proper expression vector may be prepared in various forms, comprising not only the expression regulatory elements such as a promoter, operator, start codon, stop codon, polyadenylated signal, and enhancer, but also the secretion signal sequence depending on the purpose of use. In general, when using a recombinant DNA technique, the expression vector is in the form of plasmid. In the present invention, "plasmid" and "vector" both refer to a plasmid and they can be used interchangeably, and a plasmid is the most commonly used form of a vector.

The terms "operative linkage" and "operably linked" (or "operatively linked") are used interchangeably with reference to a juxtaposition of two or more components (such as sequence elements), in which the components are arranged such that both components function normally and that at least one of the components can mediate a function exerted by at least one of the other components.

The term "recombinant" refers to the state where a cell, nucleic acid, protein, or a vector has been modified by the introduction of heterologous nucleic acid or protein or by the alteration of native nucleic acid or protein, or to the state where the cell of interest is derived from the modified cell.

The term "zinc finger nuclease" refers to a fusion protein comprising a zinc finger domain and a nucleotide cleavage domain, and it may include all the known or commercially available zinc finger nucleases. In the present invention, "zinc finger nuclease" and "ZFN" can be used interchangeably.

The term "reporter gene" refers to a gene expressing a protein which can be easily detected by a general analytic method in the art. The type of reporter gene is not limited, as long as the expression level of the gene and the position thereof in the cell, animal, or plant can be easily detected.

Reporter Construct

A method for identifying or enriching the cells, wherein a specific endogenous nucleotide sequence is cleaved by a specific nuclease or modified by such cleavage; and a system for monitoring the nuclease activity of the present invention is characterized in that it uses a reporter construct, comprising a target sequence recognized by a specific nuclease and a reporter gene.

The reporter construct of the present invention may be designed such that the expression of the reporter gene is determined by the binding of a specific nuclease to the target sequence and cleaving the reporter construct. For example, the reporter construct may comprise a reporter gene that is out of frame and thus cannot be expressed.

In one embodiment of the present invention, the reporter construct may be designed in a way that the target sequence recognized by the nuclease is inserted in the middle or in front of reporter gene and that the expression of the reporter gene is determined by the binding of nuclease expressed in the cell to the target sequence and cleaving the reporter construct.

Alternatively, the reporter construct may be designed in a way that it comprises a first reporter gene, a target sequence recognized by the nuclease, and a second reporter gene successively and that the expression of the second reporter gene is determined by the binding of the nuclease expressed in the cell to the target sequence and cleaving the reporter construct. Also, a stop codon may be inserted upstream of the second reporter gene.

Alternatively, the reporter construct may be designed in a way that it comprises a first reporter gene, a target sequence recognized by the nuclease, a second reporter gene, and a third reporter gene successively, and that the first reporter gene is expressed regardless of the binding of the nuclease to the target sequence and cleaving the reporter construct, while the expression of the second reporter gene and the third reporter gene, or both is determined by the binding of the nuclease expressed in the cell to the target sequence and cleaving the reporter construct.

The second reporter gene and the third reporter gene may be linked to the first reporter gene out of frame, while the second reporter gene and the third reporter gene are linked out of frame or in frame with each other.

One or more target sequences for nucleases to be screened can be inserted into the reporter construct by currently available cloning systems such as PCR or TOPO® (TOPO®PCR cloning system, Life Technologies, Grand Island, NY) and/or GATEWAY® (GATEWAY® Cloning System, Life Technologies, Grand Island, NY) cloning system and any other suitable method.

In the reporter construct, the 5' region of the reporter gene may be operably linked to a constitutional or inducible promoter.

The reporter gene comprised in the reporter construct may be a gene that encodes a colour-forming protein. The colour-forming protein may be a fluorescent protein or luminous protein, but is not limited thereto. The fluorescent protein may be the one selected from the group consisting of green fluorescent protein (GFP), red fluorescent protein (RFP), yellow fluorescent protein (YFP), cyan fluorescent protein (CFP), and orange fluorescent protein (OFP), but is not limited thereto.

The green fluorescent protein may be an enhanced green fluorescent protein (eGFP) or emerald GFP. The yellow fluorescent protein may be the one selected from the group consisting of Venus, mCitrine, YPet, and eYFP. The cyan fluorescent protein may be the one selected from the group consisting of CyPet, mCFPm, and Cerulean. The orange fluorescent protein may be mOrange or mKO. The red fluorescent protein may be the one selected from the group consisting of monomeric red fluorescent protein (mRFP), mCherry, tdTomato, mStrawberry, J-red, and DsRed. Also, the luminous protein may be the one selected from the group consisting of firefly luciferase, *Renilla* luciferase, and *Gaussia* luciferase. However, the luminous protein of the present invention is not limited thereto.

Also, the reporter gene of the present invention may be the gene encoding any one of the proteins selected from the group consisting of β-galactosidase, β-lactamase, TEV-protease, and dihydrofolate reductase.

In addition, the reporter gene of the present invention may be a selection marker or surface marker gene.

Furthermore, the reporter gene of the present invention may be an antibiotic resistance gene.

The reporter construct of the present invention comprises a reporter gene that is out of frame and thus cannot be expressed.

In one embodiment of the present invention, a target sequence recognized by a specific nuclease is inserted in the middle of GFP such that the C-terminal site of GFP is out of frame with the N-terminal site of GFP. When the nuclease binds to the target sequence and cleaves the reporter construct, this induces double strand break (DSB), and the DSB of gene may be repaired by a single strand annealing system, thereby allowing the expression of GFP.

In addition, in one embodiment of the present invention, a reporter construct, which comprises a first reporter gene encoding red fluorescent protein, a target sequence recognized by a specific nuclease, and a second reporter gene encoding green fluorescent protein successively, was used. When the nuclease binds to the target sequence and cleaves the reporter construct inducing DSB, then the DSB is repaired by NHEJ which is prone to frame-shift mutation, thereby increasing the possibility that both of red fluorescent protein and green fluorescent protein are expressed.

When a gene encoding fluorescent protein is used as the reporter gene, it is preferable that the first reporter gene and the second reporter gene express different fluorescent proteins so that the expression of reporter gene can be easily distinguished.

Furthermore, in another embodiment of the present invention, a reporter construct, which comprises a first reporter gene encoding fluorescent protein, a target sequence recognized by a specific nuclease, a gene encoding 2A-peptide, and a MHC class I molecule H-2K$^k$ gene which is a surface marker of the cell, was used. When the nuclease binds to the target sequence and cleaves the reporter construct, inducing DSB, then the DSB is repaired by NHEJ which is prone to frame-shift mutation, thereby allowing the expression of a fluorescent protein along with 2A-peptide and H-2K$^k$.

In another embodiment of the present invention, a reporter construct, which comprises a first reporter gene encoding a red fluorescent protein, a target sequence recognized by a specific nuclease, a second reporter gene which is out of frame with the first reporter gene and encodes green fluorescent protein, and a third reporter gene, was used. The reporter construct is designed in a way that if the nuclease binds to the target sequence, cleaves the reporter construct, and induces DSB, then the DSB is repaired by NHEJ which is prone to frame-shift mutations, thereby allowing the expression of the second fluorescent protein or the third fluorescent protein.

In another embodiment, a reporter construct comprising a first reporter gene encoding a red fluorescent protein (RFP), which is expressed regardless of nuclease activity; a target sequence recognized by the nuclease; and a second reporter gene encoding an antibiotic resistance gene (HPT) and a third reporter gene encoding a green fluorescent protein (GFP), which are linked to the first reporter gene out of frame, was prepared. In case when ZFN and a reporter are introduced together into the cell, if the ZFN properly acts on the target nucleotide sequence within the reporter, HPT gene becomes in frame with RFP gene in some of the reporters, thereby allowing the expression of HPT enzyme. Cells comprising the reporter with such mutation would be resistant to hygromycin B, and thus by treating the cells with antibiotics, one can easily select the cells whose genes are modified by nuclease.

The expression of the reporter gene can be determined by using various detecting systems that are commercially available.

For example, if a fluorescent protein-encoding gene is used as a reporter gene, the cells expressing the reporter gene or the cells not expressing the reporter gene can be detected and sorted by using fluorescence-activated cell sorting (FACS) system. FACS is a technology for cell sorting by employing flow cytometry. FACS rapidly detects the particles or cells in a liquid state when they pass a sensing point, and measures the different characteristics of each cell concurrently (size of the cell, internal composition of the cell, and functions of the cell), and depending on the cases, it can select and sort specific cells. In one example of the present invention, the cells expressing fluorescent proteins were sorted by flow cytometry, and a cell population with a high ratio of the cells whose nucleotide sequence is modified by nuclease could be isolated.

Also, if a gene encoding an antigen, which is expressed on the cell surface, is used as a second reporter gene, the cells expressing the second reporter gene or the cells not expressing the second reporter gene can be detected and sorted by using a magnetic-activated cell sorting (MACS). MACS is a technology for cell sorting by employing magnetic nanoparticles coated with the antibody against a specific antigen of cell surface. In one embodiment of the present invention, a construct comprising mRFP gene as a reporter construct, a target sequence recognized by a specific nuclease, 2A-peptide sequence, and mouse MHC class I molecule H-2K$^k$ gene successively is used; cells are labeled with H-2K$^k$-specific magnetic beads and separated by magnetism through running on the MACS column; and the cell population with a high ratio of the cells having a specific nucleotide sequence modified by the nuclease is isolated. In particular, MACS method does not utilize a laser for cell sorting, and does not cause cell damage during cell sorting process, and thus the mutant cells with modified target gene can be separated and enriched more efficiently.

Nuclease

The method, system, and reporter construct described in the present invention can be applied to a broad scope of nucleases without limitation. Preferably, the nuclease is a target-specific nuclease, and the target-specific nuclease may refer to a nuclease that can recognize and cleave a specific site of DNA on genome. The type of nuclease may include the nuclease having a recognition domain recognizing a specific target sequence on the genome, fused with a cleavage domain. Examples of the nuclease include a meganuclease; a fusion protein of a transcription activator-like (TAL) effector domain derived from phytopathogenic gene, which recognizes a specific target sequence on the genome, and a cleavage domain; or a zinc-finger nuclease, without limitation.

In one embodiment of the present invention, the nuclease may be a meganuclease. A naturally-occurring meganuclease recognizes cleavage sites of 15 to 40 base pairs, which are commonly grouped into four families: LAGLIDADG (SEQ ID NO: 75) family, GIY-YIG (SEQ ID NO: 76) family, His-Cyst box family, and HNH family. Examples of the meganuclease include I-SceI, I-CeuI, PI-PspI, PI-Sce, I-SceIV, I-CsmI, I-PanI, I-SceII, I-PpoI, I-SceIII, I-CreI, I-TevI, I-TevII, and I-TevIII.

Target sequences recognized by these meganucleases are known in the art.

In general, DNA-binding domains from naturally-occurring meganucleases, primarily from the LAGLIDADG (SEQ ID NO: 75)family, have been used to promote site-specific genome modification in plants, yeast, Drosophila, mammalian cells and mice, but this approach has been limited to the modification of either homologous genes that conserve the meganuclease recognition sequence or to pre-engineered genomes into which a recognition sequence has been introduced (Monet et al. (1999) Biochem. Biophysics. Res. Common. 255: 88-93).

Accordingly, attempts have been made to engineer meganucleases that exhibit novel binding specificity at medically or biotechnologically relevant sites. In addition, naturally-occurring or engineered DNA-binding domains from meganucleases have been operably linked with a cleavage domain from a heterologous nuclease (e.g., FokI).

In another embodiment of the present invention, the nuclease may be a zinc-finger nuclease (ZFN). ZFNs comprise a zinc finger protein that has been engineered to bind to a target site in a gene of choice and cleavage domain or a cleavage half-domain. One may refer to, for example, Beerli et al. (2002) Nature Biotechnol. 20:135-141; Pabo et al. (2001) Ann. Rev. Biochem. 70:313-340; Isalan et al, (2001) Nature Biotechnol. 19: 656-660; Segal et al. (2001) Curr. Opin. Biotechnol. 12:632-637; and Choo et al. (2000)

Curr. Opin. Struct. Biol. 10:411-416. An engineered zinc finger binding domain can have a novel binding specificity, compared to a naturally-occurring zinc finger protein. Engineering methods include, but are not limited to, rational designing and various types of selections. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence.

Selection of target sites, and method for designing and constructing the fusion proteins (and polynucleotides encoding the same) are known to those skilled in the art, and described in detail in U.S. Patent Application Nos. 2005/0064474 and 2006/0188987. Also, as disclosed in the cited references and other references, zinc finger domain and/or multi-finger zinc finger proteins may be linked together by using any suitable linker sequences, such as linkers of 5 or more amino acids in length. Example showing a linker sequence of 6 or more amino acids in length is disclosed in U.S. Pat. Nos. 6,479,626; 6,903,185; and 7,153,949. The proteins described herein may include any combination of suitable linkers in between each zinc finger of the protein.

In addition, nucleases such as ZFN and/or meganuclease comprise a nuclease (cleavage domain, cleavage half-domain). As described above, the cleavage domain may be heterologous to the DNA-binding domain, for example, a zinc finger DNA-binding domain and a cleavage domain from a nuclease or a meganuclease DNA-binding domain and cleavage domain from a different nuclease. Heterologous cleavage domains can be obtained from any endonuclease or exonuclease. Examples of the endonucleases, from which a cleavage domain can be derived, include restriction endonucleases and meganuclease, but are not limited thereto.

Similarly, a cleavage half-domain can be derived from any nuclease or portion thereof that needs to be dimerized to have a cleavage activity, as set forth above. In general, two fusion proteins are required for inducing cleavage, if the fusion protein comprises cleave half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragment thereof). In addition, the target sites for two fusion proteins are preferably positioned such that the binding of two fusion proteins to their respective target sites places the cleavage half-domains in a spatial orientation that allows the cleavage half-domains to form a functional cleavage domain, for instance, by dimerization. Therefore, in one embodiment, the adjacent sides of the target sites are separated by 5 to 8 nucleotides or by 15 to 18 nucleotides. However, any integral number of nucleotides or nucleotide pairs can intervene between two target sites (e.g., 2 to 50 nucleotide pairs or more). In general, the site of cleavage lies between the target sites.

Restriction endonucleases (restriction enzymes) are present in many types of species, and are capable of sequence-specific binding to DNA (at a recognition site) and cleaving DNA at or near the binding site. Certain types of restriction enzymes (e.g., Type IIS) cleave DNA at the sites removed from the recognition site and have separable binding and cleaving domains. For example, the Type IIS enzyme FokI catalyzes double-stranded cleavage of DNA, at 9 nucleotides from its recognition site on one strand and 13 nucleotides from its recognition site on the other. Thus, in one embodiment, fusion proteins comprise the cleavage domain (or cleavage half-domain) from at least one Type IIS restriction enzyme and one or more zinc finger binding domains, which may or may not be engineered.

Also, in one embodiment of the present invention, one of the nucleases disclosed in Table 3 can be used, but is not limited thereto.

The nuclease used in the present invention may be already expressed prior to the insertion of report construct into the cell, or may be expressed after insertion of the same. Also, the nuclease may be expressed from the endogenous nuclease gene in the cell, or expressed from the exogenous nuclease gene. To express the nuclease from exogenous gene, a nuclease-expressing construct can be introduced into the cell, and the time of insertion may be either before or after the insertion of reporter construct, or the nuclease may be inserted simultaneously with the reporter construct.

Nuclease expression constructs used in the present invention can be easily designed by using the known methods in the art. For instance, the expression of the nuclease may be under control of an inducible promoter such as the galactokinase promoter which is activated (de-repressed) in the presence of raffinose and/or galactose and repressed in presence of glucose. In particular, when a carbon source is continuously changed (for example, from glucose to raffinose, and to galactose), the galactokinase promoter is induced, thereby expressing nuclease(s). As other examples of inducible promoter, CUP1, MET1 5, PHO 5, and tet-regulated promoter may be used, but are not limited thereto.

Host Cells

Any host cell which can reconstitute a functional reporter when a target sequence is cleaved by nuclease(s) may be used in the practice of the present invention. The cell type may be a cell line or natural (e.g., isolated) cell, for example, primary cells. Cell lines may be obtained, for instance, from the American Type Culture Collection (ATCC) or generated by methods known in the art. Likewise, the cells may be isolated by using the methods known in the art. Example of cell type includes the cells that have developed or may develop a disease, such as cancerous cells, transformed cells, pathogenically infected cells, fully differentiated cells, partially differentiated cells, and immortalized cells, but is not limited thereto. Also, prokaryotes (e.g., bacteria) or eukaryotes (e.g., yeast, plant, fungal, piscine and mammalian cells such as feline, canine, murine, bovine, porcine and human cells) may be used, while eukaryotes are being preferred. Suitable mammalian cell line includes Chinese hamster ovary (CHO) cells, HEP-G2 cells, BaF-3 cells, Schneider cells, monkey kidney cells expressing SV40 T-antigen (COS cells), HEK cells, CV-1 cells, HuTu80 cells, NTERA2 cells, NB4 cells, HL-60 cells and HeLa cells, 293 cells (Graham et al. (1977) J. Gen. Virol. 36:59), and myeloma cells like SP2 or NS0 (see, e.g., Galfre and Milstein (1981) Meth. Enzymol. 73(B):3 46). Other eukaryotes include, for example, insert (e.g., sp. *frugiperda*), fungal cells as well as yeast cells (e.g., *S. cerevisiae, S. pombe, P. pastoris, K. lactis, H. polymorpha*), and plant cells (Fleer R. (1992) Current Opinion in Biotechnology 3:486 496).

In addition, the host cell may be the cultured cells (in tube), graft and primary cell culture (in tube and in vitro), or in vivo cells.

Also, the host cell of the present invention may be induced pluripotent stem cells.

That is, by using the method and reporter system of the present invention, the induced pluripotent stem cells, wherein a specific nucleotide sequence recognized by nuclease is modified, may be prepared and used in cell therapy optimized for a patient.

In addition, the cells of the present invention may be the cells from certain tissue of animals. By using the method and reporter system of the present invention, transformant cells, wherein a specific nucleotide sequence recognized by a nuclease is modified, may be produced in a large scale.

Enrichment of the Cells Having the Genes Modified by Nuclease

In the present invention, by using a reporter construct, wherein the expression of reporter gene is determined by the binding of a specific nuclease to a specific target sequence and cleaving the reporter construct, the cells, in which the nucleotide sequence is cleaved by the nuclease or modified by such cleavage, can be identified or enriched.

The modified nucleotide sequence in the cell to be identified or enriched may be an endogenous nucleotide sequence present on the genome.

Also, in the method for identifying or enriching the mutant cells, wherein the nucleotide sequence is modified by the nuclease, the mutation includes not only a local mutation, but also other types of mutation such as chromosomal rearrangements including deletion, insertion, inversion, duplication, and translocation, but is not limited thereto.

In one embodiment of the present invention, a reporter construct comprising a target sequence recognized by a specific nuclease, and a reporter gene is prepared, and introduced into a candidate cell. Before or after inserting the reporter construct into the cell, a portion or all of the cells may express the nuclease.

In order to express the nuclease from a reporter construct or exogenous nuclease gene in the cell, the reporter construct or nuclease expression construct may be inserted into the cell. A method of insertion may be the ones known in the art. For instance, exogenous DNA can be inserted into the cell by transfection or transduction. Transfection may be performed by using various methods known in the art including calcium phosphate-DNA coprecipitation, DEAE-dextran-mediated transfection, polybrene-mediated transfection, electroporation, microinjection, liposome fusion, and lipofectamine and protoplast fusion.

After inserting the reporter construct into the cell, the cell sorting is performed after the binding of nuclease to a target sequence of the reporter construct, cleaving the reporter construct, and repairing of DSB induced therefrom by cellular repair system.

The cell sorting separates the cells expressing a reporter gene and the cells not expressing the same. A group of cells expressing reporter gene has a high ratio of the cells, wherein a specific endogenous nucleotide sequence on the genome of the cell is cleaved by a specific nuclease or modified by such cleavage. Therefore, by applying the present invention, the cells in which an endogenous nucleotide sequence on the genome is modified by a nuclease can be enriched.

In one embodiment of the present invention, a reporter vector comprising a polynucleotide encoding a monomeric red fluorescent protein (mRFP), a recognition site of the ZFN, and a polynucleotide encoding enhanced green fluorescent protein (eGFP) successively was transfected into a human embryonic kidney cell, as a plasmid encoding a ZFN pair which targets P53 gene and a reporter vector. Then the RFP$^+$GFP$^+$ cell population was sorted by flow cytometry, and the mutation rate therein was measured. As a result, it was observed that a mutation rate in the RFP$^+$GFP$^+$ cell population was about 20 times higher than that in the RFP$^-$GFP$^-$ cell population and the RFP$^+$GFP$^-$ cell population. In short, the method of the present invention can increase the ratio of the cells whose genes are modified by nuclease, that is, it can significantly enrich the mutant cells induced by nuclease, given same number of cells in the group.

As another embodiment, a plasmid encoding a ZFN pair which targets CCR5 gene and the reporter vector were transfected into the cells, and the RFP$^+$GFP$^+$ cell population was sorted by flow cytometry. After measuring a mutation rate in the cell populations, it was found that the mutation rate in the RFP$^+$GFP$^+$ cell population was about 11 times higher than that in the RFP$^-$GFP$^-$ cell population and RFP$^+$GFP$^-$ cell population, and as a result of fPCR analysis, the mutation rate in the RFP$^+$GFP$^+$ cell population was about 38 times higher than the other two groups.

Furthermore, as similar to the zinc finger nuclease, when a TALE nuclease was applied, the mutation rate was significantly high in the cell population sorted by flow cytometry, wherein both fluorescent proteins were expressed.

In addition, the reporter system of the present invention and the method for enriching the cells, whose genes are modified by nuclease, using the same have the following advantages.

First, the reporter system of the present invention can reflect the nuclease activity without affecting their activity, and thus it can be used in combination with other methods which can increase the nuclease activity.

Second, the present reporter system is non-invasive, and thus in order to further enrich the mutant cell population, the plasmid insertion into the cell and cell sorting can be performed repeatedly. Biallelic gene-knockout cells can be obtained by repeating these processes. Furthermore, the gene-modified cells isolated by flow cytometry or under fluorescence microscope are the live cells, and thus they are suitable to be used for somatic-cell nuclear transfer or preparation of induced pluripotent stem cells.

Third, the present reporter construct is transferred in the form of episome plasmid which disappears along with nuclease plasmid after 1 or 2 weeks through cell division in the culture, and thus the whole genome excluding nuclease target sequence remains intact without DNA damages.

EXAMPLES

Hereinafter, the present invention is described in more detail with reference to Examples. However, these Examples are for illustrative purposes only, and the invention is not intended to be limited by these Examples.

Experimental Methods

Preparation of Plasmids Encoding ZFNs and TALENs

A plasmid encoding the zinc-finger nuclease (ZFN) used in the present invention was prepared by the method described in previous study by Kim et al., (2009). *Genome Res.* 19(7), 1279. A plasmid encoding a ZFN pair which targets TP53 comprises a polynucleotide of sharkey RR FokI domain (TP53-L) represented by SEQ ID No. 1 and a polynucleotide of sharkey DAS FokI domain (TP53-R) represented by SEQ ID No. 3. The DNA-recognizing helices of a polynucleotide of sharkey RR FokI domain (TP53-L) represented by SEQ ID No. 1 and polynucleotide of sharkey DAS FokI domain (TP53-R) represented by SEQ ID No. 3 are underlined in the sequences disclosed in FIG. 1. ZFN used in the present invention targets the internal region of exon 5. Also, in the present invention, a nuclease domain of ZFN took a form of obligate heterodimer (KK/EL(Miller et al., 2007) or sharkey DAS/RR(Guo et al., 2010)).

A plasmid encoding TAL effectors (TALEs) which targets human CCR5 gene was prepared by the method similar to the one described in Kim et al., (2009). Genome Res. 19(7), 1279.

In addition, the plasmids encoding the TAL-effector nucleases (TALENs) comprising the amino acid sequences represented by SEQ ID Nos. 48 and 49, and the TALEN comprising the amino acid sequences represented by SEQ ID Nos. 50 and 51 were prepared by the known methods in the art.

Preparation of pRGS Vector

First, mRFP gene was amplified from pcDNA3-mRFP by using the primers having a sequence represented by SEQ ID Nos. 5 and 6 as shown in Table 1, and the amplified product was cloned into the NheI site of pEGFP-N1 (Clontech). Also, eGFP gene was amplified by using the primers having a sequence represented by SEQ ID Nos. 7 and 8, and cloned into the BamHI and NotI sites of the plasmid, thereby generating a plasmid, pRGS.

TABLE 1

| | | |
|---|---|---|
| mRFP | F | 5'-GCGGCTAGCCACCATGGCCTCCTCCGAGGACGTCATC-3' (SEQ ID No. 5) |
| mRFP | R | 5'-GCGGCTAGCGAATTCGGCGCCGGTGGAGTGGCGGCCC-3' (SEQ ID No. 6) |
| eGFP | F | 5'-GCGGGATCCAGTGAGCAAGGGCGAGGAGCTG-3' (SEQ ID No. 7) |
| eGFP | R | 5'-GTCGCGGCCGCTTTACTTGTAC-3' (SEQ ID No. 8) |

To prepare another reporter plasmid, mRFP gene was amplified from pcDNA3-mRFP by using the primers having a sequence of SEQ ID Nos. 5 and 6, and the amplified gene product was cloned into the site between NheI and EcoRI sites in pEGFP-N1 (Clontech). The 2A-peptide and eGFP genes were amplified from the E2A-inserted pEGFP-N1 by using the primers having a sequence of SEQ ID Nos. 9 and 10, and cloned into the site between BamHI and NotI sites. Then, the NheI site of the plasmid was removed by silencing mutation, and a new NheI site was inserted downstream of 2A-petide gene. Meanwhile, mouse MHC class I molecule H-2K$^k$ gene was amplified from pMACSK$^k$.II (miltenyi biotech) by using the primers having a sequence of SEQ ID Nos. 10 and 11, and cloned into the plasmid at the site between NheI and NotI sites to replace eGFP gene. A target nucleotide sequence recognized by ZFN was prepared by annealing the synthetic oligonucleotides (Bioneer, Daejon, South Korea) in vitro and cloning the annealed sequence into the plasmid at the site between EcoRI and BamHI sites.

TABLE 2

| | | |
|---|---|---|
| 2A-peptide | | 5'-GGCGGATCCTCAATGTACTAACTACGCTTTGTTG-3' (SEQ ID No. 9) |
| 2A-peptide | | 5'-GGGCGCGGCCGCCTACTTGTACAGCTCGTCCATGC-3' (SEQ ID No. 10) |
| H-2K$^k$ | | 5'-GGCGCTAGCATGGCACCCTGCATGCTGCTCCTGCTGTTGGCCGCGG-3' (SEQ ID No. 11) |
| H-2K$^k$ | | 5'-GCCGCGGCCGCTTACCCTCCTTTTCCACCTGTGTT-3' (SEQ ID No. 12) |

Preparation of Reporter Constructs

Oligonucleotides comprising the target sequence of nuclease were synthesized in vitro (Bioneer, Daejon, South Korea) and annealed. The sequences of target sites are shown in Table 3.

TABLE 3

| Synthetic nucleases (Programmable nuclease) | Target sequence | SEQ ID No. |
|---|---|---|
| ZFN-224_L | 5'-GATGAGGATGAC-3' | 13 |
| ZFN-224_R | 5'-AAACTGCAAAAG-3' | 14 |
| Z891_L | 5'-ATAGATGATGGG-3' | 15 |
| Z891_R | 5'-GTCGGGGAGAAG-3' | 16 |
| TP53_L | 5'-GGCGCGGACGCG-3' | 17 |
| TP53_R | 5'-CATCTACAAGCA-3' | 18 |
| TALEN_L | 5'-TGCATCAACCCCATCATC-3' | 19 |
| TALEN_R | 5'-TAGTTTCTGAACTTCTCCCC-3' | 20 |
| Thumpd3_L | 5'-CGAGCACGCCGC-3' | 21 |
| Thumpd3_R | 5'-GGAGACCGGAAG-3' | 22 |
| CMAH-ZFN_L | 5'-AAGCAGGACCGA-3' | 23 |
| CMAH-ZFN_R | 5'-CGAGGATGGTGG-3' | 24 |
| NFKB2a-L | 5'-TCGGGGGTGGCTCCCACATG-3' | 25 |
| NFKB2a-R | 5'-TAGCCCCCGGCTGCACCCCC-3' | 26 |
| NFKB2b-L | 5'-TCGACTACGGCGTCACCGCG-3' | 27 |
| NFKB2b-R | 5'-TGGCGCTGTCCCGCCAGCAG-3' | 28 |

The annealed oligonucleotides were inserted into the vector (pRGS) which was restriction digested with EcoR1 and BamH1. Among the reporter constructs, the sequence of the reporter construct comprising a target sequence for TP53 is represented by SEQ ID No. 29 and disclosed in FIG. 2. In particular, a target sequence for ZFN is underlined in the sequence shown in FIG. 2.

Furthermore, the sequence of a double frame reporter construct comprising a target sequence for TALEN is disclosed in FIG. 16 (SEQ ID No. 52) and FIG. 17 (SEQ ID No. 53), while the sequence of a double frame reporter construct comprising a target sequence for CMAH-ZFN is disclosed in FIG. 24 (SEQ ID No. 54) and FIG. 25 (SEQ ID No. 55).

Cell Culture

Human embryonic kidney 293T (HEK 293T) cells were cultured in Dulbecco's modified Eagle medium (DMEM, Welgene) supplemented with 100 units/ml penicillin, 100 g/ml streptomycin, and 10% fetal bovine serum (FBS). Mouse induced pluripotent stem cell (iPS) established by Andras Nagy and Knut Woltje was obtained from Andras Nagy (Mount Sinai Hospital, Toronto, Canada), and cultured on the gelatinated culture dish without feeder cell, containing Glasgow modified Eagle medium (Sigma) supplemented with 10% FBS, 0.1 mM non-essential amino acid (Invitrogen), 1 mM sodium pyruvate, 0.1 mM 2-mercaptoethanol, 2000 U/mL leukemia inhibitory factor (LIF), 100 units/ml penicillin, and 100 g/ml streptomycin. In order to obtain mouse iPS cell-derived fibroblast, the cells were cultured for 3 weeks without LIF.

Transfection

HEK293 cells were transfected by using FUGENE™ 6 or FUGENE ™ HD (Roche), and mouse iPS cell-derived fibroblast was transfected by using Magnetofection (Chemicell). In the experiments associated with ZFN, a plasmid encoding ZFN: a plasmid encoding other ZFN: a reporter were mixed in a ratio of 1:1:2 by weight, and in the experiment associated with TENs, the ratio was adjusted to 1:1:1 by weight. Except for the experiment associated with TENs, the flow cytometry was performed on the transfected cells after 3 days of transfection.

Cells transfected with TEN were cultured at 30° C. (low temperature shock) for 3 days and at 37° C. for a day, before conducting flow cytometry.

T7E1 Assay

T7E1 assay was performed by the method known in the art. as described previously. In short, genomic DNA was isolated by using DNEASY™ Blood & Tissue Kit (Qiagen, Valencia Calif.) according to the manufacturer's instructions.

The DNA region comprising a recognition site of synthetic nuclease was PCR-amplified using the primers shown in Table 4.

TABLE 4

| CCR5 (ZFN-224) | F | 5'-GAGCCAAGCTCTCCATCTAGT-3' (SEQ ID No. 30) |
| | R | 5'-CTGTATGGAAAATGAGAGCTGC-3' (SEQ ID No. 31) |
| CCR5 (Z891) | F | 5'-GAGCCAAGCTCTCCATCTAGT-3' (SEQ ID No. 32) |
| | NF | 5'-TTAAAGATAGTCATCTTGGGGC-3' (SEQ ID No. 33) |
| | R | 5'-TCACAAGCCCACAGATATTT-3' (SEQ ID No. 34) |
| TP53 | F | 5'-GCAGGAGGTGCTTACGCATGTTTGT-3' (SEQ ID No. 35) |
| | R | 5'-GCTGCTCACCATCGCTATCTGAGC-3' (SEQ ID No. 36) |
| CCR5 (TALEN) | F | 5'-GAGCCAAGCTCTCCATCTAGT-3' (SEQ ID No. 37) |
| | NF | 5'-TTAAAGATAGTCATCTTGGGGC-3' (SEQ ID No. 38) |
| | R | 5'-TCACAAGCCCACAGATATTT-3' (SEQ ID No. 39) |
| Thumpd3 | F | 5'-CAACCGAGCATCCGCTCGCTAGG-3' (SEQ ID No. 40) |
| | R | 5'-GAAGGGGCTGGAGTGGTGTTACCG-3' (SEQ ID No. 41) |

The amplicons obtained by the PCR were denatured by heating and annealed to form a heteroduplex DNA. The heteroduplex DNA was treated with 5 units of T7 endonuclease I (New England Biolabs) for 15 minutes at 37° C. and analyzed by running through agarose gel electrophoresis.

Performing Fluorescent PCR (fPCR)

Genomic DNA (100ng per reaction) was amplified by PCR using PHUSION® High-Fidelity Polymerase (Fynnzymes, Oy, Thermo-Fisher Scientific, Waltham Mass.) and 5'-FAM-labelled primer. The sequence of primers used is shown in Table 5.

TABLE 5

| CCR5 (ZFN-224) | F | 5'-TGCACAGGGTGGAACAAGATGG-3' (SEQ ID No. 42) |
| | R | 5'-FAM-GAGCCCAGAAGGGGACAGTAAGA AGG-3' (SEQ ID No. 43) |

TABLE 5 -continued

| CCR5 (Z891) | F | 5'-FAM-GAATAATTGCAGTAGCTCTAACA GG-3' (SEQ ID No. 44) |
| | R | 5'-CTCTTGCTGGAAAATAGAACAGC-3' (SEQ ID No. 45) |
| TP53 | F | 5'-GCAGGAGGTGCTTACGCATGTTTGT-3' (SEQ ID No. 46) |
| | R | 5'-FAM-GCTGCTCACCATCGCTATCTGAGC-3' (SEQ ID No. 47) |

The amplified PCR product was analyzed by ABI 3730×1 DNA analyzer. The position and size of peak represent the length and relative amount of PCR products respectively.

Replication Analysis for Single Cell and Cell Colony

Before and after performing the cell sorting, single cells were separated by mouth pipette under microscope, and transferred to a PCR tube. Then, PCR products were replicated and analyzed for sequence analysis. To obtain replication population of the cell, the sorted cells and unsorted cells were dispersed on a Petri dish at a density of 1,000 cells/100 mm dish, and after 2 weeks, the cell colonies were isolated.

Flow Cytometry

Adherent cells were trypsinized and resuspended in 2% FBS in PBS. Single cell suspensions were analyzed and sorted by using FACS ARIA™ II (BD Biosciences, San Jose, Calif.) or FACSV™ ANTAGE SE cell sorters (BD Biosciences, San Jose, Calif.). To obtain the cells involving nuclease-induced mutation, the cells having a strong GFP signal were isolated. Untransfected cells and cells transfected with only reporters were used as controls.

Magnetic-Activated Cell Sorting (MACS)

HEK293 cells were co-transfected with 2ug of reporter plasmids and 2ug of plasmids encoding ZFN-224 (targeting CCR5 gene). After 3 days of transfection, the cells were labeled and separated magnetically by using MACS® ELECT $K^k$ cell separation reagents (Miltenyi Biotech), and then a genomic DNA was isolated (first sorting). To increase the purity of magnetically labeled fraction, the cells were purified by running them through a second column (second sorting).

HEK293 cells were co-transfected with 2 ug of reporter plasmids and 2 ug of plasmids encoding ZFN-224 (targeting CCR5 gene). After 3 days of transfection, the cells were labeled and separated magnetically by using MACSelect $K^k$ (miltenyi Biotech), and then a genomic DNA was isolated (first sorting). To increase the purity of magnetically labeled fraction, the cells were purified by running them through a second column (second sorting).

Example 1

Preparation of Reporter Construct and Sorting of the Cells Whose Genes are Modified by Synthetic Nuclease, by Using the Same A target sequence for a synthetic nuclease was inserted in between the DNA sequences encoding monomeric red fluorescent protein (mRFP) and enhanced green fluorescent protein (eGFP) in the reporter plasmid encoding mRFP and eGFP, such that eGFP sequence would be out of frame with mRFP sequence. A stop codon was inserted upstream of eGFP sequence (see FIG. 3(a)).

After transfecting HEK293 cells with the reporter plasmid, the transfected cells were sorted by flow cytometry. As a result, it was observed that mRFP was expressed by CMV promoter, but a functional eGFP was not expressed since it was out of frame with the promoter when the synthetic nuclease was not active. If DSB is generated at a target sequence by synthetic nuclease, the damage of DNA can be repaired by NHEJ, however this causes a frame-shift mutation. Such mutation allows eGFP to be in frame with mRFP, thereby inducing the expression of a functional mRFP-eGFP fusion protein. By applying this principle, cells whose genes are modified by synthetic nuclease could be isolated and enriched (see FIG. 3(b)).

In addition, a target sequence of nuclease could be inserted within the coding region of surrogate gene such as eGFP gene. In this case, a nuclease target sequence could be inserted such that the C-terminal site of eGFP would be out of frame with the N-terminal of eGFP.

As a result, the surrogate gene lost the activity thereof, and the cells transfected with the surrogate gene were shown as GFP-. On the other hand, when the synthetic nuclease bound to a target sequence and cleaved DNA, this induced DSB, which was then repaired by NHEJ that often causes frame-shift mutation, and thus some of the cells were shown as GFP+.

Also, in the present invention, a different type of surrogate gene, for instance, a single strand annealing system was used. In this system, the reporter construct was inactive, partially replicated, and encoded a mutant reporter gene (FIG. 4a). A target sequence was inserted in the middle of replicated region. If a site-specific nuclease binds to a target sequence and cleaves DNA, then the DNA is repaired by SSA mechanism (various HR), thereby generating a functional reporter gene. Likewise, a reporter system which can be repaired by HR may be used. This system involves an inactive reporter gene, and the gene was designed as a homologous DNA donor which can encode a nuclease target sequence and an inactive reporter whose ends are cleaved (FIG. 4b). Once a synthetic nuclease binds to a target sequence and cleaves DNA, causing DSB, the DSB can be repaired by HR, thereby allowing the reporter gene to be active.

Example 2

Enrichment and Sorting of the Cells Whose Genes are Modified by TP53 Gene-Targeting ZFN A plasmid encoding a ZFN pair which targets a human TP53 gene and a reporter plasmid comprising a nuclease target sequence were co-transfected into HEK293 cells. As a control, HEK293 cells were transfected with a reporter plasmid or a ZFN plasmid alone.

After 24 hours of transfection, a majority of the cells appeared as RFP+, while GFP+ cells were rarely detected. However, the number of GFP+ cells gradually increased after 3 days, and the GFP+ cells were all RFP+ (FIG. 5). After 72 hours of transfection, a flow cytometry was performed. As a result, it was observed that about 16% of the cells were RFP+GFP-, and about 5% of the cells were RFP+GFP+ (FIG. 6a).

The RFP+GFP+ cell population was sorted by flow cytometry. In order to examine the mutation rate induced by nuclease, genomic DNA was isolated and analyzed.

As a result of performing a T7 endonuclease I (T7E1) assay on the genomic DNA, it was found that the mutation frequency of TP53 gene in the RFP+GFP+ cell population was 37%, which was 13 times higher than that of the unsorted cells (FIG. 6b). The unsorted cells, i.e., RFP-GFP- cells, RFP+GFP- cells, and the cells transfected with a ZFN plasmid alone showed a mutation frequency of about 2.8% to 4.8%. Based on these results, it is evident that by using the present reporter system, a significantly increased number of gene-modified cells can be enriched.

Also, fluorescent polymerase chain reaction (fPCR) was performed to quantify the indel mutations induced by ZFN. As a result, it was found that the amount of cells having indel mutation in the sorted RFP+GFP+ cell population was about 29 times higher compared to the unsorted cells (RFP-GFP- cells or RFP+GFP- cells) (FIG. 6c). This result corresponds with the result of T7E1 assay shown above. Subsequently, the PCR products were obtained and the DNA sequence adjacent to a target sequence was analyzed. As a result, it was observed that a mutation frequency was 20% in the RFP+GFP+ cell population, and 1% in the unsorted cells. This indicates that the mutation frequency can be increased about 20 times by cell sorting (FIG. 6d).

Overall, in the present example, it was confirmed that the surrogate reporter of the present invention allows a significant enrichment of the target gene-modified cells, and it is a reliable system for monitoring ZFN activity in the live cells.

Example 3

Enrichment and Sorting of the Cells Whose Genes are Modified by ZFN that Targets CCR5 Gene In order to examine whether the reporter system of the present invention can be applied to enrich the cells whose genes are modified by other ZFNs, ZFN-224 and Z891 which target different sequences in the human CCR5 gene were used.

After 72 hours of transfecting the cells with ZFN-224 and performing flow cytometry, it was observed that 23% of the cells appeared as RFP+GFP+ (FIG. 7a). Also, as a result of T7E1 assay, the sorted RFP+GFP+ cell population showed a mutation rate of 69%, and the unsorted cells, i.e., RFP-GFP- and RFP+GFP- cells showed a mutation rate of 12 to 16%. That is, the sorted RFP+GFP+ cells had about 5.8 times higher mutation rate than the unsorted cells (FIG. 7b).

In addition, as a result of fPCR analysis, it was confirmed that the sorted RFP+GFP+ cell population showed about 17 times higher amount of mutant cell enriched compared to the unsorted cells, i.e., RFP-GFP- cells, or RFP+GFP- cells (FIG. 7c).

Furthermore, it was examined whether the RFP+GFP+ cell population had higher number of mutant cells induced by Z891, compared to the unsorted cells. As a result of T7E1 assay, it was found that the sorted RFP+GFP+ cells showed about 11 times higher mutation rate than the unsorted cells, i.e., RFP-GFP- cells and RFP+GFP- (FIG. 8b). Also, as a result of fPCR analysis, it was confirmed that the sorted RFP+GFP+ cells showed about 38 times increased mutation rate that the unsorted cells (FIG. 8c).

Example 4

Sorting of the Cells Having a Gene Mutation Induced by TALENs

In the present example, it was examined whether the reporter system of the present invention can be applied to TALENs. For this purpose, a reporter plasmid and a plasmid encoding a TALEN pair which targets CCR5 gene were co-transfected into HEK293 cells. The cells were cultured at 37° C. for a day, and at 30° C. for another 3 days. The cultured cells were analyzed by flow cytometry. As a result, the activity of TALEN could not be examined in the unsorted cells, however in the RFP⁺GFP⁺ cells, a gene mutation could be clearly observed. That is, the enrichment of mutant cells in the sorted cell population was 8.6 times greater than that in the unsorted cells (FIG. 9).

Example 5

Enrichment and Sorting of the Mouse Cells Wherein Thumpd3 Gene is Modified

In this example, it was examined whether the reporter system of the present invention can be applied to other cell lines derived from different species. For this purpose, a plasmid encoding a ZFN pair which targets a mouse gene Thumpd3, and a reporter of the present invention were co-transfected into the mouse fibroblast derived from induced pluripotent stem cells.

In the unsorted cells, ZFN activity could be rarely observed, whereas in the RFP⁺GFP⁺ cells, about half of the cells (46%) had Thumpd3 alleles mutated. That is, the number of gene-modified cells enriched in the cell population was increased by 92 times or more (FIG. 10).

Example 6

Replication Analysis of Single Cells and Cell Groups (Colony)

Single cells and replicated cell groups were analyzed before and after sorting the cells by flow cytometry. Before sorting the cells, among 21 single mouse fibroblasts, none of the cells had ZFN-induced mutation in the Thumpd3 region (FIG. 11). On the other hand, 9 of 10 RFP⁺GFP⁺ single cells had mutation, and 4 of those had biallelic mutations. In addition, after cell sorting, two independent replica of the Thumpd3-modified fibroblast could be separated. Overall, the replication analysis results support that the reporter system of the present invention could efficiently enrich the gene-modified cells which have monoallelic gene and biallelic gene mutations.

Example 7

Comparison of the Mutation Rates Between the Sorted Cells and Unsorted Cells

Based on the above results, it was found that two factors contribute to the result of mutant cell enrichment by the reporter system of the present invention. One is the effect of co-transfection, and the other is the effect of surrogate reporter. The effects of these two factors can be determined by comparing the mutation rate (or indel mutation rate (%)) in the RH⁺GFP⁻ cells (effect of co-transfection) with the mutation rate in the RH⁺GFP⁺ cells (both of the effects of co-transfection and surrogate reporter). The present inventors have found that compared to the unsorted cells, the RH⁺GFP⁻ cells had slightly increased mutation rate (Table 6). On the other hand, a mutation rate in the RH⁺GFP⁺ cells was significantly increased, and this indicates that surrogate gene affects the result of mutant cell enrichment the most.

TABLE 6

| Target gene | Mutation rate (%) | | | Fold enrichment | |
|---|---|---|---|---|---|
| | Unsorted | Sorted (RFP⁺ GFP⁻) | Sorted (RFP⁺ GFP⁺) | Sorted (RFP⁺ GFP⁻) | Sorted (RFP⁺ GFP⁺) |
| TP53 | 2.8 | 4.8 | 37 | 1.7 | 13 |
| CCR5 (ZFN-224) | 12 | 16 | 69 | 1.3 | 5.8 |
| CCR5 (Z891) | 0.8 | 3.0 | 8.7 | 3.8 | 11 |
| CCR5 (TALEN) | 0.5 | 1.5 | 4.3 | 3.0 | 8.6 |
| Thumpd3 | 0.5 | 2.4 | 46 | 4.8 | 92 |

To identify a potential mechanism behind the enrichment of mutant cells by a reporter, the present inventors sorted the cells to a group of RFP$^{dim}$, RFP$^{medium}$, and RFP$^{bright}$ cells, and RFP⁻GFP⁺ and RFP⁺GFP⁺ cells, and measured the mutation rate and level of nuclease. In the sorted cells, 'dim' indicates a dark fluorescent colour, 'medium' indicates a moderate brightness of fluorescent colour, and 'bright' indicates a bright fluorescent colour. Through T7E1 assay, it was identified that the level of enrichment of genome-modified cells was in the following order: RFP$^{bright}$ (10% mutation), RFP$^{medium}$ (6.3% mutation), and RFP$^{dim}$ (1.2% mutation) (FIG. 12). Based on these results, it was found that high transfection efficiency leads to a high mutation frequency. However, the enrichment level of the gene-modified cells in the RFP$^{bright}$ cell population (7.7 times higher compared to the unsorted cells) was not as high as the enrichment level in RFP⁺GFP⁺ cell population (44% of the cells were mutated, which was 34 times higher compared to the unsorted cells). This indicates that the reporter system of the present invention is more efficient than other simple sorting method which is based on transfection efficiency.

Furthermore, based on the western blotting, it was observed that the level of nuclease coincided with the mutation frequency, and this indicates that a high mutation rate in RFP⁺GFP⁺ cells was partially induced by high nuclease concentration.

Also, it was examined whether the transfection and cell sorting can be performed repeatedly by using the reporter system of the present invention, for further enriching the mutant cell population. A reporter plasmid and a plasmid encoding Z891 were co-transfected into HEK2993 cells, and after 3 days of transfection, RFP⁺GFP⁺ cells were sorted by flow cytometry (first sorting), which was then analyzed by T7E1 assay. The sorted cells were cultured for 24 hours, co-transfected with a reporter plasmid and a Z891 plasmid, and sorted by flow cytometry again. The sorted RFP⁺GFP⁺ cells were then analyzed by T7E1 assay (second sorting). As a result, twice repeated processes of co-transfection and cell sorting increased the enrichment of mutant cells by 60 times. This indicates that a cell population comprising close to 50% of the CCR5 alleles-modified cells could be separated by repeating the process of co-transfection and cell sorting (FIG. 13).

Example 8

Enrichment of Target Gene-Modified Cells Through Magnetic-Activated Cell Sorting (MACS)

As a method for sorting and enriching the target gene-modified cells, a magnetic-activated cell sorting (MACS) was used instead of flow cytometry, which sorts the cells that are activated by fluorescence.

A reporter system was designed to comprise a mRFP gene, a target sequence for synthetic nuclease, 2A-peptide sequence, and mouse MHC class I molecule H-2K$^k$ gene (FIG. 14a). In the reporter system, mRFP is expressed by CMV promoter, but H-2K$^k$ gene is not expressed when the synthetic nuclease is not active since the gene is located out of frame. If DSB is generated in a target sequence by a synthetic nuclease, the DNA damage can be repaired by NHEJ, but this causes frame-shift mutation. Such mutation makes the 2A-peptide and H-2K$^k$ gene to be in frame with mRFP, thereby inducing the expression of a functional H-2K$^k$ protein. After 3 or 4 days of co-transfecting a reporter plasmid and a plasmid encoding nuclease into the cells, the cells can be labeled with H-2K$^k$-specific magnetic beads and separated by magnetic force on the MACS column (FIG. 14b).

Based on the above experimental design, HEK293 cells were co-transfected with 2 ug of reporter plasmid and 2 ug of ZFN-224-endocing plasmid (which targets CCR5 gene). The reporter plasmid consists of mRFP gene, a target sequence of ZFN-224, 2A-peptide sequence, and mouse MHC class I molecule H-2K$^k$ gene. After 3 days of transfection, the cells were magnetically labeled and separated by using MACSelect K$^k$ (miltenyi Biotech), and then genomic DNA was separated therefrom (first sorting). In order to increase the purity of magnetically-labeled fraction, the cells were separated by running through the second column (second sorting). The genomic DNA was isolated from the magnetic bead-adsorbed cells and analyzed by T7E1 assay. As a result, the unsorted cells by MACS showed 18% mutation rate, whereas the cells from first sorting showed 67% mutation rate, and the cells from second sorting showed 77% mutation rate (FIG. 15). That is, the cells sorted by MACS showed about 4.5 times higher mutation rate compared to the unsorted cells. As MACS method does not use laser for cell sorting, the cells are not damaged by sorting process, and thus the target gene-modified mutant cells could be sorted and enriched more efficiently.

Example 9

Enrichment and Sorting of the Gene-Modified Cells by Using a Double Frame NHEJ Reporter Construct A double frame NHEJ reporter construct was used to enrich the gene-modified cells, wherein a specific endogenous nucleotide sequence is cleaved by nuclease and modified by such cleavage, at higher efficiency.

To be specific, a CMV promoter was used for the intracellular expression, and a double frame NHEJ reporter construct was prepared by successively locating a mRFP reporter gene (first reporter gene), which is a control reporter gene to determine the gene insertion efficiency; a target sequence recognized by nuclease; and two copies of eGFP reporter genes (second and third reporter gene), which is located out of amino acid codon frame with the red fluorescent protein encoded by the mRFP reporter gene and thus cannot be expressed.

A detailed constitution of the reporter construct is shown in the first diagram of FIG. 18.

When the reporter construct was transfected into the cell, if the reporter construct was successfully introduced into the cell, the mRFP was expressed regardless of the activity of synthetic nuclease. On the other hand, when the synthetic nuclease was inactive, the second reporter gene and the third reporter gene were located out of frame, and thus they were not expressed. When DSB was generated in the target sequence by the synthetic nuclease, the DNA damage was repaired by NHEJ, but this caused frame-shift mutation. Such mutation made the second reporter gene or third reporter gene to be in frame with the first reporter gene, thereby inducing the expression of a functional mRFP-eGFP fusion protein (FIG. 18).

To be specific, each of a first reporter construct comprising a first reporter gene (mRFP) and a second reporter gene (eGFP) which is located out of amino acid codon frame with the first reporter gene; a second reporter construct comprising a first reporter gene (mRFP) and a second reporter gene (eGFP) which is located out of amino acid codon frame with the first reporter gene but in a different frame from the first reporter construct; and a third reporter construct comprising a first reporter gene (mRFP) and a second reporter gene (eGFP) and third reporter gene (eGFP), which are out of amino acid codon frame with the first reporter gene and are in a different frame with each other, was inserted into the cell separately, and a nuclease was also introduced into the cell. The cells expressing both of mRFP and eGFP were sorted by flow cytometry and the presence of frame-shift mutations therein was determined. As a result, when the first reporter construct or the second reporter construct was used, only the cells having one case of codon frame-shift by nuclease could be identified. On the other hand, when the third reporter construct was used, the cells having two cases of frame-shift mutations could be selected and enriched (FIG. 19).

In the present example, the first reporter gene was located out of amino acid codon frame with the second reporter gene and the third reporter gene, and through which the cells involving all the cases of NHEJ-mediated frame-shift mutation, which is caused by target site cleavage by synthetic nuclease, could be sorted, and the gene-modified cells by synthetic nuclease could be enriched.

That is, when the reporter construct comprises only a first reporter gene and a second reporter gene located out of frame therewith, the cells having only one type of frame-shift mutation could be identified, however by using the reporter construct of the present invention, the cells having two types of frame-shift mutations could be selected.

Example 10

Enrichment and Sorting of the Gene-Modified Cells by Using Hygromycin Reporter Construct A reporter construct employed a CMV promoter for intracellular expression, and comprised a RFP gene for determining the gene insertion efficiency, a target gene recognized by ZFN, and a hygromycin phosphotransferase (HPT-eGFP) gene, which was designed to be expressed when ZFN is properly functioning (FIG. 20).

The 36 ug of ZFN pairs, which can knockout a porcine CMAH gene, and 9 ug of the reporter constructs for hygromycin selection were introduced into the porcine ear tissue cells through electroporation. Then $1\times10^6$ cells were dispersed onto a 100 mm plate and cultured. On the second day of ZFN and reporter construct insertion, the number of cells was $3\times10^5$ per plate. Then the cells were treated with 300 ug/ml of hygromycin B for 48 hours, and on the fourth day, the culture medium was replaced by a fresh medium without hygromycin B. At this time, the number of cells survived after hygromycin treatment was $1.5\times10^4$. On the seventh day, initial colonies were formed, and on the 18$^{th}$ day, a complete colony was formed. Then on the 22$^{nd}$ day, the developed colonies were transferred to a new 96-well culture plate and the transformant cell line whose genes are modified by nuclease was prepared (FIG. 21).

The expression levels of RFP and GFP in the cells were compared among the groups that were before the treatment of hygromycin B on the 2$^{nd}$ day of inserting ZFN and reporter; and groups that were treated or untreated with hygromycin B on the 4$^{th}$ day of treatment. The proportion of RFP- and GFP-expres sing cells was higher in the hygromycin B-treated group than in the untreated group or the group before the treatment (see Table 7 and FIG. 22).

TABLE 7

| Hygromycin B-treated group | Number of fluorescent protein-expressing cell | | |
|---|---|---|---|
| | RFP/Total (%) | GFP/Total (%) | GFP/RFP (%) |
| Before treatment (on 2$^{nd}$ day) | 120/339 (35.4) | 69/339 (20.0) | 69/120 (57.5) |

TABLE 7-continued

| Hygromycin B-treated group | Number of fluorescent protein-expressing cell | | |
|---|---|---|---|
| | RFP/Total (%) | GFP/Total (%) | GFP/RFP (%) |
| 0 ug/ml treatment (on 4$^{th}$ day) | 58/165 (35.2) | 26/165 (15.8) | 26/58 (44.8) |
| 300 ug/ml treatment (on 4$^{th}$ day) | 47/48 (97.9) | 38/48 (79.2) | 38/47 (80.9) |

Also, starting on the second day of inserting ZFN and reporter into the cell, the cells were treated with 300 ug/ml hygromycin B for 2 days, and then the selected cells were analyzed by T7E1 assay to determine the ratio of gene-modified cells. Compared to the untreated control group (3.1%), there was a higher ratio of transformed cells in the treated group (12.1%) (FIG. 23).

The invention claimed is:

1. A non-homologous end joining (NHEJ) reporter construct for identifying, selecting, or enriching cells that have been modified by NHEJ at a target sequence in the genome of the cells, the construct comprising in 5' to 3' order:
   a) a promoter,
   b) a first reporter gene operably linked to the promoter,
   c) the target sequence, wherein the target sequence is recognized by a nuclease specific for the target sequence, and
   d) a second reporter gene,
   wherein the second reporter gene is out of frame with the first reporter gene, such that in the absence of the nuclease only the first reporter gene is expressed and wherein in the presence of the nuclease, the target sequence is cleaved and NHEJ repair results in a frame shift mutation that renders the first reporter gene in frame with the second reporter gene such that both the first reporter gene and the second reporter gene are expressed from the promoter.

2. The NHEJ reporter construct according to claim 1, wherein the first or second reporter gene encodes a protein that is selected from the group consisting of beta-galactosidase, β-lactamase, TEV-protease, dihydrofolate reductase, luciferase, Renilla luciferase, Gaussia luciferase, selection marker, surface marker, fluorescent protein, and antibiotic resistance protein.

3. An isolated host cell, comprising one or more than two of the NHEJ reporter construct of claim 1.

4. An isolated system for monitoring nuclease activity, comprising one or two or more of the NHEJ reporter construct of claim 1; a host cell; a nuclease-expressing construct, wherein the NHEJ reporter construct, the nuclease-expressing construct, or both are already introduced into the host cell or prepared aside from the cell.

5. A method for identifying or enriching cells, wherein a specific endogenous nucleotide sequence is cleaved by a specific nuclease or modified by such cleavage, comprising
   a first step of preparing a reporter construct of claim 1;
   a second step of inserting the reporter construct of claim 1 into a candidate cell, wherein a portion or all of the candidate cells express the nuclease before or after inserting the reporter construct; and
   a third step of sorting candidate cells obtained from said second step into cells expressing the reporter gene or cells not expressing the reporter gene.

6. The method according to claim 5, wherein the specific endogenous nucleotide sequence is an intrinsic nucleotide sequence present in the genome.

7. The method according to claim 5, wherein the nuclease expressed in the second step is expressed in the cell temporarily, or is expressed from a gene encoding the nuclease inserted in the genome of the cell.

8. The method according to claim 5, wherein the third step of sorting the cell is performed by fluorescence-activated cell sorting (FACS) or magnetic-activated cell sorting (MACS).

9. The method according to claim 5, wherein the second step and the third step are repeated twice or more.

10. The method according to claim 5, wherein the nuclease activity is examined through the third step of sorting the cells, which sorts the cells expressing the reporter gene and the cells not expressing the reporter gene.

11. A non-homologous end joining (NHEJ) reporter construct for identifying, selecting or enriching cells that have been modified by NHEJ at a target sequence in a genome of the cells, the construct comprising in 5' to 3' order:
   a) a promoter,
   b) a first reporter gene operably linked to the promoter,
   c) the target sequence, wherein the target sequence is recognized by a nuclease specific for the target sequence,
   d) a second reporter gene, and
   e) a third reporter gene,
   wherein the second reporter gene is out of frame with the first reporter gene and the third reporter gene is out of frame with the first reporter gene, such that in the absence of the nuclease, only the first reporter gene is expressed and wherein in the presence of the nuclease, the target sequence is cleaved and NHEJ repair results in a frame shift mutation that renders the first reporter gene in frame with the second reporter gene and/or the third reporter gene such that the second reporter gene and/or the third reporter gene are expressed with the first reporter gene.

12. The NHEJ reporter construct according to claim 11, wherein the second reporter gene and the third reporter gene are linked out of frame to each other.

13. The NHEJ reporter construct according to claim 11, wherein the second reporter gene and the third reporter gene are linked in frame to each other.

14. The NHEJ reporter construct according to claim 13, wherein the second reporter gene and the third reporter gene are different types of reporter genes.

15. The NHEJ reporter construct according to claim 11, wherein the first, the second or the third reporter gene encodes a protein that is selected from the group consisting of beta-galactosidase, β-lactamase, TEV-protease, dihydrofolate reductase, luciferase, Renilla luciferase, Gaussia luciferase, selection marker, surface marker, fluorescent protein, and antibiotic resistance protein.

16. An isolated host cell, comprising one or more than two of the NHEJ reporter construct of claim 11.

17. An isolated system for monitoring nuclease activity, comprising one or two or more of the NHEJ reporter construct of claim 11; a host cell; a nuclease-expressing construct, wherein the reporter construct, the nuclease-expressing construct, or both are already introduced in the host cell or prepared aside from the cell.

* * * * *

UNITED STATES PATENT AND TRADEMARK OFFICE
CERTIFICATE OF CORRECTION

PATENT NO. : 9,809,839 B2
APPLICATION NO. : 14/000920
DATED : November 7, 2017
INVENTOR(S) : Jin Soo Kim et al.

It is certified that error appears in the above-identified patent and that said Letters Patent is hereby corrected as shown below:

On the Title Page

Left column, item (75), Inventors, "Seok Joong Kim" should read --Seokjoong Kim--.

Signed and Sealed this
Twenty-fourth Day of July, 2018

Andrei Iancu
*Director of the United States Patent and Trademark Office*